(12) United States Patent
Mezo et al.

(10) Patent No.: US 7,820,162 B2
(45) Date of Patent: Oct. 26, 2010

(54) METHODS FOR CHEMICALLY SYNTHESIZING IMMUNOGLOBULIN CHIMERIC PROTEINS

(75) Inventors: Adam R. Mezo, Waltham, MA (US); Robert T. Peters, West Roxbury, MA (US)

(73) Assignee: Syntonix Pharmaceuticals, Inc., Waltham, MA (US)

( * ) Notice: Subject to any disclaimer, the term of this patent is extended or adjusted under 35 U.S.C. 154(b) by 13 days.

(21) Appl. No.: 12/100,183

(22) Filed: Apr. 9, 2008

(65) Prior Publication Data

US 2008/0249288 A1 Oct. 9, 2008

Related U.S. Application Data

(62) Division of application No. 10/842,054, filed on May 6, 2004, now Pat. No. 7,381,408.

(60) Provisional application No. 60/469,600, filed on May 6, 2003, provisional application No. 60/487,964, filed on Jul. 17, 2003, provisional application No. 60/539,207, filed on Jan. 26, 2004.

(51) Int. Cl.
C07K 14/00 (2006.01)
(52) U.S. Cl. .................... 424/133.1; 530/333; 530/334; 530/338; 530/350; 530/408
(58) Field of Classification Search ............. 424/133.1; 530/333, 334, 338, 350, 408
See application file for complete search history.

(56) References Cited

U.S. PATENT DOCUMENTS

| | | | |
|---|---|---|---|
| 3,941,763 A | 3/1976 | Sarantakis | |
| 4,695,623 A | 9/1987 | Stabinsky | |
| 4,784,950 A | 11/1988 | Hagen et al. | |
| 4,831,119 A | 5/1989 | Nordfang et al. | |
| 4,897,471 A | 1/1990 | Stabinsky | |
| 5,077,204 A | 12/1991 | Brake et al. | |
| 5,093,246 A | 3/1992 | Cech et al. | |
| 5,116,964 A | 5/1992 | Capon et al. | |
| 5,162,220 A | 11/1992 | Oshima et al. | |
| 5,175,096 A | 12/1992 | Höök et al. | |
| 5,189,015 A | 2/1993 | Höök et al. | |
| 5,234,830 A | 8/1993 | Oshima et al. | |
| 5,258,498 A | 11/1993 | Huston et al. | |
| 5,428,130 A | 6/1995 | Capon et al. | |
| 5,464,933 A | 11/1995 | Bolognesi et al. | |
| 5,480,981 A | 1/1996 | Goodwin et al. | |
| 5,482,858 A | 1/1996 | Huston et al. | |
| 5,579,277 A | 11/1996 | Kelly et al. | |
| 5,585,089 A | 12/1996 | Queen et al. | |
| 5,591,573 A | 1/1997 | Whalen et al. | |
| 5,605,689 A | 2/1997 | Ammann | |
| 5,624,821 A | 4/1997 | Winter et al. | |
| 5,648,240 A | 7/1997 | Hook et al. | |
| 5,723,125 A | 3/1998 | Chang et al. | |
| 5,739,277 A | 4/1998 | Presta et al. | |
| 5,807,706 A | 9/1998 | Carter et al. | |
| 5,808,029 A | 9/1998 | Brockhaus et al. | |
| 5,869,046 A | 2/1999 | Presta et al. | |
| 5,885,821 A | 3/1999 | Magota et al. | |
| 5,910,573 A | 6/1999 | Plückthun et al. | |
| 6,013,263 A | 1/2000 | Barney et al. | |
| 6,015,881 A | 1/2000 | Kang et al. | |
| 6,017,536 A | 1/2000 | Barney et al. | |
| 6,030,613 A | 2/2000 | Blumberg et al. | |
| 6,060,065 A | 5/2000 | Barney et al. | |
| 6,060,613 A | 5/2000 | Hattori et al. | |
| 6,068,973 A | 5/2000 | Barney et al. | |
| 6,086,875 A | 7/2000 | Blumberg et al. | |
| 6,093,799 A | 7/2000 | Li et al. | |
| 6,184,344 B1 | 2/2001 | Kent et al. | |
| 6,228,983 B1 | 5/2001 | Barney et al. | |
| 6,281,331 B1 | 8/2001 | Kang et al. | |
| 6,310,180 B1 | 10/2001 | Tam | |
| 6,310,183 B1 | 10/2001 | Johannessen et al. | |
| 6,323,323 B1 | 11/2001 | Sledziewski et al. | |
| 6,326,468 B1 | 12/2001 | Canne et al. | |
| 6,329,176 B1 | 12/2001 | Wöldike et al. | |
| 6,469,136 B1 | 10/2002 | Bray et al. | |
| 6,475,491 B1 | 11/2002 | Johnson et al. | |
| 6,485,726 B1 | 11/2002 | Blumberg et al. | |
| 6,518,013 B1 | 2/2003 | Barney et al. | |
| 6,660,843 B1 | 12/2003 | Feige et al. | |
| 7,084,109 B2 | 8/2006 | Dennis et al. | |

(Continued)

FOREIGN PATENT DOCUMENTS

EP 0 325 262 B1 7/1989

(Continued)

OTHER PUBLICATIONS

Armour, K.L., et al., "Recombinant human IgG molecules lacking Fcγ receptor I binding and monocyte triggering activities," *Eur. J. Immunol.* 29:2613-2624, Wiley (1999).

(Continued)

*Primary Examiner*—Chih-Min Kam
(74) *Attorney, Agent, or Firm*—Sterne, Kessler, Goldstein & Fox P.L.L.C.

(57) ABSTRACT

The invention provides methods of chemically synthesizing chimeric proteins comprising at least a portion of an immunoglobulin constant region and a biologically active molecule.

16 Claims, 7 Drawing Sheets

U.S. PATENT DOCUMENTS

| | | |
|---|---|---|
| 7,348,004 B2 | 3/2008 | Peters et al. |
| 7,381,408 B2 | 6/2008 | Mezo et al. |
| 7,385,032 B2 | 6/2008 | Tschopp et al. |
| 7,404,956 B2 | 7/2008 | Peters et al. |
| 2002/0081664 A1 | 6/2002 | Lo et al. |
| 2002/0106374 A1 | 8/2002 | Olson et al. |
| 2003/0119727 A1 | 6/2003 | Dennis et al. |
| 2003/0180287 A1 | 9/2003 | Gambotz et al. |
| 2003/0235536 A1 | 12/2003 | Blumberg et al. |
| 2004/0077022 A1 | 4/2004 | Feige et al. |
| 2004/0110929 A1 | 6/2004 | Bjorn et al. |
| 2005/0027109 A1 | 2/2005 | Mezo et al. |
| 2005/0037941 A1 | 2/2005 | Munoz et al. |
| 2005/0037947 A1 | 2/2005 | Bitonti et al. |
| 2005/0147618 A1 | 7/2005 | Riviera et al. |
| 2005/0281829 A1 | 12/2005 | Hehir et al. |
| 2007/0172928 A1 | 7/2007 | Peters et al. |

FOREIGN PATENT DOCUMENTS

| | | |
|---|---|---|
| EP | 0 464 533 A1 | 1/1992 |
| EP | 0 589 577 B1 | 2/1997 |
| FR | 2 641 468 A | 7/1990 |
| WO | WO 88/09810 A1 | 12/1988 |
| WO | WO 89/10134 A1 | 2/1989 |
| WO | WO 90/11364 A1 | 10/1990 |
| WO | WO 92/10209 A1 | 6/1992 |
| WO | WO 93/11162 A1 | 6/1993 |
| WO | WO 96/22024 | 7/1996 |
| WO | WO 00/06605 | 2/2000 |
| WO | WO 00/18881 A2 | 4/2000 |
| WO | WO 01/02439 A1 | 1/2001 |
| WO | WO 01/02440 A1 | 1/2001 |
| WO | WO 01/03737 A1 | 1/2001 |
| WO | WO 01/36637 A1 | 5/2001 |
| WO | WO 01/58935 A2 | 8/2001 |
| WO | WO 01/83526 A2 | 11/2001 |
| WO | WO 01/91780 A1 | 12/2001 |
| WO | WO 02/18417 A1 | 3/2002 |
| WO | WO 02/46208 A2 | 6/2002 |
| WO | WO 02/089828 A2 | 11/2002 |
| WO | WO 03/077834 A2 | 9/2003 |
| WO | WO 2004/003176 A2 | 1/2004 |
| WO | WO 2004/006962 A2 | 1/2004 |
| WO | WO 2004/101740 A2 | 11/2004 |
| WO | WO 2005/001025 A2 | 1/2005 |
| WO | WO 2005/051289 A2 | 6/2005 |

OTHER PUBLICATIONS

Aruffo, A., et al., "CD44 is the principal cell surface receptor for hyaluronate," *Cell* 61:1303-1313, Cell Press (1990).

Ashkenazi, A., et al., "Protection against endotoxic shock by a tumor necrosis factor receptor immunoadhesin," *Proc. Natl. Acad. Sci. U.S. A.* 88:10535-10539, National Academy of Science (1991).

Bahlmann, F.H., et al., "Erythropoietin: is it more than correcting anaemia?," *Nephrol. Dial. Transplant.* 19:20-22, Oxford University Press (2004).

Barré-Sinoussi, F., et al., "Isolation of a T-lymphotropic retrovirus from a patient at risk for acquired immune deficiency syndrome (AIDS)," *Science* 220:868-871, Association for the Advancement of Science (1983).

Baru M. et al., "Liposome-encapsulated DNA mediated gene transfer and synthesis of human factor IX in mice," *Gene* 161: 143-150, Elsevier Science B. V. (1995).

Bennett, B.D., et al., "Extracellular Domain-IgG Fusion Proteins for Three Human Natriuretic Peptide Receptors," *J. Biol. Chem.* 266:23060-230607, American Society for Biochemistry and Molecular Biology (1991).

Brennan, M., et al., "Preparation of Bispecific Antibodies by Chemical Recombination of Monoclonal Immunoglobulin $G_1$ Fragments," *Science* 229:81-83, Association for the Advancement of Science (1985).

Botti, P., et al., "Cyclic Peptides from Linear Unprotected Peptide Precursors through Thiazolidine Formation," *J. Am. Chem. Soc.* 118:10018-10024, American Chemical Society (1996).

Broze, G.J., Jr. and Majerus, P.W., et al., "Purification and Properties of Human Coagulation Factor VII," *J. Biol. Chem.* 255:1242-1247, American Society for Biochemistry and Molecular Biology (1980).

Burmeister, W.P., et al., "Crystal structure at 2.2 Å resolution of the MHC-related neonatal Fc receptor," *Nature* 371:323-324, Nature Publishing Group (1994).

Byrn, R.A., et al., "Biological properties of a CD4 immunoadhesin," *Nature* 344:667-670, Nature Publishing Group (1990).

Capon, D.J., et al., "Designing CD4 immunoadhesins for AIDS therapy," *Nature* 337:525-531, Nature Publishing Group (1989).

Carter, D.C. and Ho, J.X., "Structure of Serum Albumin," *Adv. Prot. Chem.* 45:153-203, Academic Press (1994).

Chalupny, N.J., et al., "T-cell activation molecule 4-1BB binds to extracellular matrix proteins," *Proc. Natl. Acad. Sci. U.S.A.* 89:10360-10364, National Academy of Science (1992).

Chan, D.C. and Kim, P.S., "HIV Entry and Its inhibition," *Cell* 93:681-684, Cell Press (1998).

Clerc, F.F., et al., "Primary structure control of recombinant proteins using high-performance liquid chromatography, mass spectrometry and microsequencing," *J. Chromatogr. B Biomed. Appl.* 662:245-259, Elsevier (1994).

Cohen, A.J. and Kessler, C.M., "Acquired Inhibitors," *Baillieres Clin. Hematol.* 9:331-354, Bailliere Tindall (1996).

Dagleish, A.G., et al., "The CD4 (T4) antigen is an essential component of the receptor for the AIDS retrovirus," *Nature* 312:763-767, Nature Publishing Group (1984).

Dargaud Y. and Negrier C., "Heamophilia therapies," Expert Opinions on Biological Therapy, 7(5): 651-663, Ashley Publications Ltd. (2007).

Davis, L.E., et al., "Preparation and characterization of antibodies with specificity for the amino-terminal tetrapeptide sequence of the platelet-derived connective tissue activating peptide-III," *Biochem. Int.* 10:395-404, Academic Press (1985).

Dawson, P.E. and Kent, S.B.H., "Synthesis of native Proteins by Chemical Ligation," *Annu. Rev. Biochem.* 69:923-960, Annual Reviews (2000).

De Clercq, E., et al., "New anti-HIV agents and targets," *Med. Res. Rev.* 22:531-565, Wiley (2002).

Dugaiczyk, A., et al., "Nucleotide sequence and the encoded amino acids of human serum albumin mRNA," *Proc. Natl. Acad. Sci. U.S.A.* 79:71-75, National Academy of Science (1982).

Erickson, B.W. and Merrifield, R.B., "Solid-Phase Peptide Synthesis," in *The Proteins*, 3$^{rd}$ ed., Neurath, H. and Hill, R.L., eds., Springer, New York, N.Y., pp. 255-527 (1976).

Finn, F.M. and Hofmann, K., "The synthesis of peptides by solution methods with emphasis on peptide hormones," in *The Proteins*, 3$^{rd}$ ed., Neurath, H. and Hill, R.L., eds., Springer, New York, N.Y., pp. 105-237 (1976).

Fischer, K., et al., "The effects of postponing prophylactic treatment on long-term outcome in patients with severe hemophilia," *Blood* 99:2337-2341, American Society for Hematology (2002).

Friend, P.J., et al., "Phase 1 study of an engineered aglycosylated humanized CD3 antibody in renal transplant rejection," *Transplantation* 68:1632-1637, Lippincott Williams & Wilkins (1999).

Frostell-Karlsson, Å., et al., "Biosensor Analysis of the Interaction between Immobilized Human Serum Albumin and Drug Compounds for Prediction of Human Serum Albumin Binding Levels," *J. Med. Chem.* 43:1986-1992, American Chemical Society (2000).

Gallo, R.C., et al., "Frequent Detection and Isolation of cytopathic Retroviruses (HTLV-III) from Patents with AIDS and at Risk for AIDS," *Science* 224:500-503, Association for the Advancement of Science (1984).

Gascoigne, N.R., et al., "Secretion of a chimeric T-cell receptor-immunoglobulin protein," *Proc. Natl. Acad. Sci. U.S.A.* 84:2936-2940, The National Academy of Science (1987).

Geoghegan, K.F. and Stroh, J.G., "Side-directed conjugation of nonpeptide groups to peptides and proteins via periodate oxidation of a 2-amino alcohol. Application to modification at N-terminal serine," *Bioconjugate Chem.* 3:138-146, American Chemical Society (1992).

Ghetie, V. and Ward, E.S., "Multiple Roles for the Major Histocompatability Complex Class I-Related Receptor FcRn," *Annu. Rev. Immunol.* 18:739-766, Annual Reviews (2000).

Glennie, M.J. and Stevenson, G.T., "Univalent antibodies kill tumor cells in-vitro and in-vivo," *Nature* 295:712-714, Nature Publishing Group (1982).

Hage, D.S. and Tweed, S.A., "Recent advances in chromatographic and electrophoretic methods for the study of drug-protein interactions," *J. Chromatography* 699:499-525, Elsevier (1997).

Hagen, F.S., et al., "Characterization of a cDNA coding for human factor VII," *Proc. Natl. Acad. Sci. U.S.A.* 83:2412-2416, National Academy of Science (1986).

Hammarkjöld, H. and Rekosh, D., "The molecular biology of the human immunodeficiency virus," *Biochim. Biophys. Acta* 989:269-280, Elsevier (1989).

Israel, E.J., et al., "Expression of the neonatal Fc receptor, FcRn, on human intestinal epithelial cells," *Immunology* 92:69-74, Blackwell Sciences (1997).

Jelesarov, I. and Bosshard, H.R., "Thermodynamic Characterization of the Coupled Folding and Association of Heterodimeric Coiled Coils (Leucine Zippers)," *J. Mol. Biol.* 263:344-358, Academic Press (1996).

Johannessen, M., et al., "Comparison of the factor VII:C clot analysis and a modified activated factor VII analysis for monitoring factor VII activity in patients treated with recombinant activated factor VII (NovoSeven®)," *Blood Coagul. Fibrinolysis* 11:S159- S164, Lippincott Williams and Wilkins (2000).

Jones, P.T., et al., "Replacing the complementarity-determining regions in a human antibody with those form a mouse," *Nature* 321:522-525, Nature Publishing Group (1986).

Kang, A.S., et al., "Linkage of recognition and replication functions by assembling combinatorial antibody Fab libraries along phage surfaces," *Proc. Natl. Acad. Sci. U.S.A.* 88:4363-4366, National Academy of Science (1991).

Kasper, C.K., "Hereditary plasma clothing factor disorders and their management," *Haemophilia* 6:13-27, Blackwell Science (2000).

Ketas, T.J., et al., "Human Immunodeficiency Virus Type 1 Attachment, Coreceptor, and Fusion Inhibitors Are Active against both Direct and *trans* Infection of Primary Cells," *J. Virol.* 77:2762-2767, American Society for Microbiology (2003).

Kilby, J.M., et al., "Potent suppression of HIV-1 replication in humans by T-20, a peptide inhibitor of gp41-mediated virus entry," *Nat. Med.* 4:1302-1307, Nature Publishing Group (1998).

Kobayashi, N., et al., "FcRn-mediated transcytosis of immunoglobulin G in human renal proximal tubular epithelial cells," *Am J. Physiol.* 282:F358-F365, American Physiological Society (2002).

Kostelny, S.A., et al., "Formation of a bispecific antibody by the use of leucine zippers," *J. Immunol.* 148:1547-1553, American Association of Immunologists (1992).

Kürschner, C., et al., "Construction, Purification, and Characterization of New Interferon γ (IFNγ) Inhibitor Proteins," *J. Biol. Chem.* 267:9354-9360, American Society for Biochemistry and Molecular Biology (1992).

Landolfi N. F., "A Chimeric IL-1/Ig Molecule Possesses the Functional Activity of Both Proteins," *J. Immunol.* 146: 915-919, American Association of Immunologists (1991).

Lemaitre, M., et al., "Specific antiviral activity of a poly(L-lysine)-conjugated oligodeoxyribonucleotide sequence complementary to vesicular stomatitis virus N protein mRNA initiation site," *Proc. Natl. Acad. Sci. U.S.A.* 84:648-652, National Academy of Science (1987).

Lesslauer, W., et al., "Recombinant soluble tumor necrosis factor receptor proteins protect mice from lipopolysaccharide-induced lethality," *Eur. J. Immunol.* 21:2883-2886, Wiley (1991).

Letsinger, R.L., et al., "Cholesteryl-conjugated oligonucleotides: synthesis, properties, and activity as inhibitors of replication of human immunodeficiency virus in cell culture," *Proc. Natl. Acad. Sci. U.S.A.* 86:6553-6536, National Academy of Science (1989).

Li, Y.X. et al., "Expression of TPO Mimetic Peptide Chimetic Proteins with Human IgG1 Fc Fragments and Their Biological Characters," *Sheng Wu Gong Cheng Xue Bao*, 18(4): 424-30, Ke xue chu ban she (1985).

Linsley, P.S., et al., "Binding of the B cell activation antigen B7 to CD28 costimulates T cell proliferation and interleukin 2 mRNA accumulation," *J. Exp. Med.* 173:721-730, Rockefeller University Press (1991).

Linsley, P.S., et al., "CTLA4 Is a Second Receptor for the B Cell Activation Antigen B7," *J. Exp. Med.* 174:561-569, Rockefeller University Press (1991).

Louis, J.M., et al., "Design and Properties of $N_{CCG}$-gp41, a Chimeric gp41 Molecule with Nanomolar HIV Fusion Inhibitory Activity," *J. Biol. Chem.* 276:29485-298489, American Society for Biochemistry and Molecular Biology (2001).

Maddon, P.J., et al., "The T4 Gene Encodes the AIDS Virus Receptor and Is Expressed in the Immune system and the Brain," *Cell* 47:333-348, Cell Press (1986).

Maeda, Y., et al., "Effective renaturation of denatured and reduced immunoglobulin G in vitro without assistance of chaperone," *Protein Eng.* 9:95-100, Oxford University Press (1996).

Marks, J.D., et al., "By-passing immunization: Building high affinity antibodies by chain shuffling," *Biotechnology* 10:779-783, Nature Publishing Group (1992).

Masui, H., et al., "Cytotoxicity against Human Tumor Cells Mediated by the Conjugate of Anti-Epidermal Growth Factor Receptor Monoclonal Antibody to Recombinant Ricin A Chain," *Cancer Res.* 49:3482-3488, American Association for Cancer Research (1989).

McCafferty, J., et al., "Phage antibodies: filamentous phage displaying antibody variable domains," *Nature* 348:552-554, Nature Publishing Group (1990).

McPherson, H., et al., "Synthesis of an RNA-peptide conjugate by orthogonal ligation," *Synlett.* S1:978-980, Georg Thieme Verlag (1999).

Merrifield, R.B., "Solid Phase Peptide Synthesis. I. The Synthesis of a Tetrapeptide," *J. Am. Chem. Soc.* 85:2149-2154, American Chemical Society (1963).

Merrifield, R.B., "Solid-phase peptide synthesis," in *The Chemistry of Polypeptides*, Katsoyannis, P.G., ed., Plenum Publishing Corporation, New York, N.Y., pp. 335-361 (1973).

Muir, T.W., et al., "Expressed protein ligation: A general method for protein engineering," *Proc. Natl. Acad. Sci. U.S.A.* 95:6705-6710, National Academy of Science (1998).

Nilsson, I.M., "The management of Hemophilia Patients with Inhibitors," *Trans. Med. Rev.* 6:285-293, Elsevier (1992).

Nussbaum, O., et al., "Fusogenic Mechanisms of Enveloped-Virus Glycoproteins Analyzed by a Novel Recombinant Vaccinia Virus-Based Assay Quantitating Cell fusion-Dependent Reporter Gene Activation," *J. Virol.* 68:5411-5422, American Society for Microbiology (1994).

Oravcova, J., et al., "Drug-protein binding studies new trends in analytical and experimental methodology," *J. Chromatography* 677:1-28, Elsevier (1996).

Pedersen, A.H., et al., "Autoactivation of Human Recombinant Coagulation Factor VII," *Biochemistry* 28:9331-9336, American Chemical Society (1989).

Peppel, K., et al., "A Tumor Necrosis Factor (TNF) Receptor-IgG Heavy Chain Chimeric Protein as a Bivalent Antagonist of TNF Activity," *J. Exp. Med.* 174:1483-1489, Rockefeller University Press (1991).

Petrini, P., "What factors should influence the dosage and interval of prophylactic treatment in patients with severe haemophilia A and B?," *Hemophilia* 7:99-102, Wiley (2001).

Pontikaki I. et al., "Side effects of anti-TNF α therapy in juvenile idiopathic arthritis," *Reumatismo*, 58(1): 31-38, Longanesi (2006).

Rahimipour, S., et al., "Design, synthesis, and evaluation of a long-acting, potent analogue of gonadotropin-releasing hormone," *J. Med. Chem.* 44:3645-3652, American Chemical Society (2001).

Ridgway, J. and Gorman, C., "Expression and Activity of IgE Receptor Alpha Chain-IgG Chimeric Molecules," *J. Cell. Biol.* 115, Abstract No. 1448, Rockefeller University Press (1991).

Root, M.J., et al., "Protein Design of an HIV-1 Entry Inhibitor," *Science* 291:884-888, Association for the Advancement of Science (2001).

Rossi, J.J., "Making ribozymes work in cells," *Curr. Biol.* 4:469-471, Elsevier (1994).

Routledge, E.G., et al., "The effect of aglycosylation on the immunogenicity of a humanized therapeutic CD3 monolconal antibody," *Transplantation* 60:847-853, Lippincott Williams & Wilkins (1995).

Sarin, P.S., et al., "Inhibiton of acquired immunodeficiency syndrome virus by oligodeoxynucleoside methylphosphonates," *Proc. Natl. Acad. Sci. U.S.A.* 85:7448-7451, National Academy of Science (1988).

Sarver, N., et al., "Ribozymes as potential anti-HIV-1 therapeutic agents," *Science* 247:1222-1225, Association for the Advancement of Science (1990).

Seelig, G.F., et al., "Synthetic mimics of juxtaposed amino- and carboxyl-terminal peptide domains of human gamma interferon block ligand binding to human gamma interferon receptor," *J. Biol. Chem.* 1:358-363, American Society for Biochemistry and Molecular Biology (1994).

Severinov, K. and Muir, T.W., "Expressed Protein Ligation, a Novel Method for Studying Protein-Protein Interaction in Transcription," *J. Biol. Chem.* 273:16205-16209, American Society for Biochemistry and Molecular Biology (1998).

Shields, R.L., et al., "High Resolution Mapping of the Binding Site on Human IgG1 for FcγRI, FcγRII, FcγRIII, and FcRn and Design of IgG1 Variants with Improved Binding to the FcγR," *J. Biol. Chem.* 276:6591-6604, American Society for Biochemistry and Molecular Biology (2001).

Solulink Biosciences Bioconjugation, Immbolization & Detection Reagents, Kits and Services Catalog (p. 4), 2005, retrieved Dec. 22, 2005, from http://www.solulink_catalog.pdf.

Stamenkovic, I., et al., "The B Lymphocyte Adhesion Molecule CD22 Interacts with Leukocyte Common Antigen CD45RO on T Cells and α2-6 Sialyltransferase, CD75, on B Cells," *Cell* 66:1133-1144, Cell Press (1991).

Stein, C.A., et al., "Physiocochemical properties of phosphorothioate oligodeoxynucleotides," *Nucl. Acids. Res.* 16:3209-3221, Oxford University Press (1988).

Stetsenko, D.A. and Gait, M.J., "Efficient Conjugation of Peptides to Oligonucleotdies by 'Native Ligation'," *J. Organic Chemistry* 65:4900-4908, American Chemical Society (2000).

Stevenson, G.T., et al., "Chimeric Univalent Antibodies for Treating Lymphoid Malignancies," *Med. Oncol. Tumor Pharm.* 1:275-278, Humana Press (1984).

Stevenson, G.T., et al., "Conjugation of Human Fc γ in Closed-Hinge or Open-Hinge Configuration to Fab'γ and Analogous Ligands," *J. Immunol.* 158: 2242-2250, American Association of Immunologists (1997).

Story, C.M., et al., "A major histocompatibility complex class I-like fc receptor cloned from human placenta: possible role in transfer of immunoglobulin G from mother to fetus," *J. Exp. Med.* 180:2377-2381, Rockefeller University Press (1994).

Swaminathan, S. and Khanna, N., "Affinity Purification of Recombinant Interferon-α on a Mimetic Ligand Adsorbent," *Prot. Expr. Purif.* 15:236-242, Elsevier (1999).

Traunecker, A., et al., "Highly efficient neutralization of HIV with recombinant CD4-immunoglobulin molecules," *Nature* 339:68-70, Nature Publishing Group (1989).

Ueda, T., et al., "Favourable interaction between heavy and light chains arrests the undesirable oligomerization of heavy chains in the refolding of denatured and reduced immunoglobulin G," *Cell Mol. Life Sci.* 53:929-934, Birkhäuser Basel (1997).

Van der Krol, A.R., et al., "Modulation of eukaryotic gene expression by complementary RNA or DNA sequences," *Bio Techniques* 6:958-976, Informa Healthcare USA (1988).

Van der Meer, P., et al., "Eruthropoietin in cardiovascular diseases," *Eur. J. Heart Fail.* 25: 285-291, Oxford Journals (2004).

Van der Meer, P., et al., "Erythropoietin improves left ventricular function and coronary flow in an experimental model of ischemia-reperfusion injury," *Eur. J. Heart Fail.* 6:853-859, Oxford Journals (2004).

Waldmann, T.A., "Albumin Catabolism," in *Albumin Structure, Function and Uses*, Rosenoer, V.M., et al., eds., Pergamon Press, Princeton, NJ, pp. 255-273 (1977).

Ward, E.S. and Ghetie, V., "The effector functions of immunoglobulins: implications for therapy," *Ther. Immunol.* 2:77-94, Blackwell Scientific Publications (1995).

Waterhouse, P., et al., "Combinatorial infection and in vivo recombination: a strategy for making large phage antibody repertoires," *Nucl. Acids. Res.* 21:2265-2266, Oxford University Press (1993).

Watson, S.R., et al., "A Homing Receptor-IgG Chimera as a Probe for Adhesive Ligands of Lymph Node High Endothelial Venules," *J. Cell. Biol.* 110:2221-2229, Rockefeller University Press (1990).

Watson, S.R., et al., "Neutrophil influx into an inflammatory site inhibited by a soluble homing receptor-IgG chimaera," *Nature* 349:164-167, Nature Publishing Group (1991).

Wild, C., et al., "A Synthetic peptide inhibitor of human immunodeficiency virus replication: Correlation between solution structure and viral inhibition," *Proc. Natl. Acad. Sci. U.S.A.* 89:10537-10541, National Academy of Science (1992).

Wild, C.T., et al., "Peptides corresponding to a predictive alpha-helical domain of human immunodeficiency virus type 1 gp41 are potent inhibitors of virus infection," *Proc. Natl. Acad. Sci. U.S.A.* 91:9770-9774, National Academy of Science (1994).

Wilken, J. and Kent, S.B., "Chemical Protein Synthesis," *Curr. Opin. Biotechnol.* 9:412-426, Current Biology (1988).

Xu, D., et al., "Mimetic ligand-based affinity purification of immune complexes and immunoconjugates," *J. Chromatogr. B Biomed Sci. Appl.* 706:217-229, Elsevier (1998).

Zatsepin, T.S., et al., "Synthesis of peptide-oligonucleotide conjugates with single and multiple peptides attached to 2'-aldehydes through thiazolidine, oxime, and hydrazine linkages," *Bioconjugate Chem.* 13:822-830, American Chemical Society (2002).

Zettmeissl, G., et al., "Expression and Characterization of Human CD4: Immunoglobulin Fusion Proteins," *DNA Cell Biol. USA* 9:347-353, Mary Ann Liebert (1990).

Zhang, L., et al., "Preparation of functionally active cell-permeable peptides by single-step ligation of two peptide molecules," *Proc. Nat. Acad. Sci. U.S.A.* 95:9184-9189, National Academy of Science (1998).

Zheng, X.X., et al., "Administration of Noncytolytic IL-10/Fc in Murine Models of Lipopolysaccharide-Induced Septic Shock and Allogenic Islet Transplantation," *J. Immunol.* 154:5590-5600, Wiley (1995).

Zon, G., "Oligonucleotide analogues as potential chemotherapeutic agents," *Pharm. Res.* 5:539-549, Kluwer Academic/Plenum Publishers (1988).

Advisory Action for U.S. Appl. No. 10/841,250, Peters, R.T., filed May, 6, 2004, mailed on Apr. 18, 2007.

Advisory Action for U.S. Appl. No. 10/841,250, Peters, R.T., filed May 6, 2004, mailed on Jul. 12, 2007.

Notice of Appeal and Pre-Appeal Brief Request for Review for U.S. Appl. No. 10/841,250, dated Jul. 25, 2007.

Notice of Panel Decision from Pre-Appeal Brief Review for U.S. Appl. No. 10/841,250, mailed on Aug. 28, 2007, United States Patent Office, Alexandria, Virginia.

Office Action for U.S. Appl. No. 10/841,250, Peters, R.T., filed May 6, 2004, mailed on Jul. 26, 2006.

Office Action for U.S. Appl. No. 10/841,250, Peters, R.T., filed May 6, 2004, mailed on Jan. 25, 2007.

Office Action for U.S. Appl. No. 10/841,819, Riviera, D.S., filed May 6, 2004, mailed on Jul. 27, 2007.

Office Action for U.S. Appl. No. 11/029,003, Peters, R.T., filed Jan. 5, 2005, mailed on Nov. 28, 2006.

Office Action for U.S. Appl. No. 11/029,003, Peters, R.T., filed Jan. 5, 2005, mailed on Aug. 8, 2007.

Reply to Office Action for U.S. Appl. No. 11/029,003, Peters, R.T., filed Jan. 5, 2005, dated May 21, 2007.

International Search Report for International Application No. PCT/US04/13939, mailed on Jan. 25, 2005, United States Patent Office, Alexandria, Virginia.

Duga, S. & Salomon, O., "Factor XI deficiency," *Semin. Thromb. Hemost.* 35(4): 416-25, Thieme, United States (Jun. 2009; Epub Jul. 2009).

Growe, G., et al., "Hemophilia and von Willebrand's disease: 2. Management. Association of Hemophilia Clinic Directors of Canada," *Canadian Medical Association Journal* 153(2): 147-157, Canadian Medical Association, Canada (1995).

Menegatti, M. & Peyvandi, F., "Factor X deficiency," *Semin. Thromb. Hemost.* 35(4): 407-15, Thieme, United States (Jun. 2009) (abtract only).

Pipe, S., "Antihemophilic factor (recombinant) plasma/albumin-free method for the management and prevention of bleeding episodes in patients with hemophilia A," *Biologics* 3: 117-25, Dove Medical Press (NZ), New Zealand (Jul. 2009).

Australian Office Action mailed Nov. 24, 2008, for AU Appl. No. 2004239244, inventors Bitonti et al., filed May 6, 2004.

Office Action mailed Apr. 1, 2008, for U.S. Appl. No. 10/841,819, inventors Rivera et al., filed May 6, 2004.

Office Action mailed Jan. 18, 2007, for U.S. Appl. No. 10/842,054, inventors Mezo et al., filed May 6, 2004.

Office Action mailed Jul. 25, 2007, for U.S. Appl. No. 10/842,054, inventors Mezo et al., filed May 6, 2004.

Office Action mailed Mar. 12, 2009, for U.S. Appl. No. 11/588,431, inventors Peters et al., filed Oct. 27, 2006.

Office Action mailed Oct. 15, 2009, for U.S. Appl. No. 11/588,431, inventors Peters et al., filed Oct. 27, 2006.

European Office Action mailed Jun. 20, 2007, for European Application No. 04 775 946.9, applicant Syntonix Pharmaceuticals, Inc., filed May 6, 2004.

European Office Action mailed Apr. 1, 2008, for European Application No. 04 775 946.9, applicant Syntonix Pharmaceuticals, Inc., filed May 6, 2004.

European Office Action mailed Jan. 12, 2009, for European Application No. 04 775 946.9, applicant Syntonix Pharmaceuticals, Inc., filed May 6, 2004.

European Office Action mailed Jan. 19, 2010, for European Application No. 04 775 946.9, applicant Syntonix Pharmaceuticals, Inc., filed May 6, 2004.

European Office Action mailed Jan. 14, 2008, for European Application No. 04 751 356.9, applicant Syntonix Pharmaceuticals, Inc., filed May 6, 2004.

European Office Action mailed Aug. 17, 2009, for European Application No. EP 09 004 646.7,applicant Syntonix Pharmaceuticals, Inc., filed May 6, 2004.

European Office Action mailed Jan. 22, 2008, for European Application No. 04 751 357.7, applicant Syntonix Pharmaceuticals, Inc., filed May 6, 2004.

European Office Action mailed Mar. 20, 2007, for European Application No. 04 751 356.9, applicant Syntonix Pharmaceuticals, Inc., filed May 6, 2004.

European Search Report and Opinion completed May 19, 2009, for European Application No. EP 09 00 4646, filed May 6, 2004, European Patent Office, Munich, Germany.

European Supplementary Search Report completed Jul. 17, 2006, for European Application No. EP 04 75 1356, filed May 6, 2004, European Patent Office, Munich, Germany.

International Preliminary Examination Report completed Jun. 7, 2005, for International Application No. PCT/US04/13939, filed May 6, 2004, United States Patent Office, Alexandria, Virginia.

International Preliminary Report on Patentability, issued Nov. 11, 2005, for International Application No. PCT/US2004/013940, filed May 6, 2004, United States Patent Office, Alexandria, Virginia.

International Preliminary Report on Patentability, issued May 8, 2006 for International Application No. PCT/US2004/014064, filed May 6, 2004, United States Patent Office, Alexandria, Virginia.

International Search Report for International Application No. PCT/US04/13940, mailed on Jul. 29, 2005, United States Patent Office, Alexandria, Virginia.

International Search Report for International Application No. PCT/US04/14064, mailed on Apr. 6, 2006, United States Patent Office, Alexandria, Virginia.

International Search Report for International Application No. PCT/US06/000140, mailed on Jun. 2, 2006, European Patent Office, Rijswijk, Netherlands.

Supplementary European Search Report for European Application No. EP 04 75 1357, completed Apr. 25, 2007, European Patent Office, Munich, Germany.

Supplementary European Search Report for European Application No. EP 04 75 1356.9, completed Aug. 14, 2006, European Patent Office, Munich, Germany.

Supplementary European Search Report for European Application No. EP 04 77 5946, completed Nov. 16, 2006, European Patent Office, Munich, Germany.

Esp@cenet Database, Abstract for EP0464533 A1 (document FP6), (1992).

Fig. 2
CysFc amino acid sequence (hIFNα signal sequence underlined)

```
  1  MALTFALLVA  LLVLSCKSSC  SVGCPPCPAP  ELLGGPSVFL  FPPKPKDTLM
 51  ISRTPEVTCV  VVDVSHEDPE  VKFNWYVDGV  EVHNAKTKPR  EEQYNSTYRV
101  VSVLTVLHQD  WLNGKEYKCK  VSNKALPAPI  EKTISKAKGQ  PREPQVYTLP
151  PSRDELTKNQ  VSLTCLVKGF  YPSDIAVEWE  SNGQPENNYK  TTPPVLDSDG
201  SFFLYSKLTV  DKSRWQQGNV  FSCSVMHEAL  HNHYTQKSLS  LSPGK
```

Fig. 3

CysFc nucleotide sequence (hIFNα signal sequence underlined)

atggccttgacctttgctttactggtggccctcctggtgctcagctgcaagtcaagctgctctg
tgggctgccgccgtgcccagctccggaactgctgggcggaccgtcagtcttcctcttcccccc
aaaacccaaggacaccctcatgatctcccggacccctgaggtcacatgcgtggtggtggacgtg
agccacgaagaccctgaggtcaagttcaactggtacgtggacggcgtggaggtgcataatgcca
agacaaagccgcgggaggagcagtacaacagcacgtaccgtgtggtcagcgtcctcaccgtcct
gcaccaggactggctgaatggcaaggagtacaagtgcaaggtctccaacaaagccctcccagcc
cccatcgagaaaaccatctccaaagccaagggcagccccgagaaccacaggtgtacaccctgc
cccatcccgggatgagctgaccaagaaccaggtcagcctgacctgcctggtcaaaggcttcta
tcccagcgacatcgccgtggagtgggagagcaatgggcagccggagaacaactacaagaccacg
cctcccgtgttggactccgacggctccttcttcctctacagcaagctcaccgtggacaagagca
ggtggcagcaggggaacgtcttctcatgctccgtgatgcatgaggctctgcacaaccactacac
gcagaagagcctctccctgtctccgggtaaatga

Figure 5a

Amino acid sequence of Fc-MESNA (produced in pTWIN1 vector from NEB; when Fc-Intein-CBD is eluted from chitin beads with MESNA, produces the following protein with a C-terminal thioester on the final Phe residue)

```
  1 MGIEGRGAAA VDTSHTCPPC PAPELLGGPS VFLFPPKPKD TLMISRTPEV
 51 TCVVVDVSHE DPEVKFNWYV DGVEVHNAKT KPREEQYNST YRVVSVLTVL
101 HQDWLNGKEY KCKVSNKALP APIEKTISKA KGQPREPQVY TLPPSRDELT
151 KNQVSLTCLV KGFYPSDIAV EWESNGQPEN NYKTTPPVLD SDGSFFLYSK
201 LTVDKSRWQQ GNVFSCSVMH EALHNHYTQK SLSLSPGF
```

Figure 5 b
Nucleotide sequence of Fc CDS in pTWIN1 (the final F residue, ttt, directly abuts the Mxe GyrA intein CDS in pTWIN1)

```
atgggcattgaaggcagaggcgccgctgcggtcgatactagtcacacatgcccaccgtgcccag
cacctgaactcctggggggaccgtcagtcttcctcttccccccaaaacccaaggacaccctcat
gatctcccggacccctgaggtcacatgcgtggtggtggacgtgagccacgaagaccctgaggtc
aagttcaactggtacgtggacggcgtggaggtgcataatgccaagacaaagccgcgggaggag
agtacaacagcacgtaccgtgtggtcagcgtcctcaccgtcctgcaccaggactggctgaatgg
caaggagtacaagtgcaaggtctccaacaaagccctcccagcccccatcgagaaaaccatctcc
aaagccaaagggcagccccgagaaccacaggtgtacaccctgcccccatcccgggatgagctga
ccaagaaccaggtcagcctgacctgcctggtcaaaggcttctatcccagcgacatcgccgtgga
gtgggagagcaatgggcagccggagaacaactacaagaccacgcctcccgtgttggactccgac
ggctccttcttcctctacagcaagctcaccgtggacaagagcaggtggcagcaggggaacgtct
tctcatgctccgtgatgcatgaggctctgcacaaccactacacgcagaagagtctctccctgtc
tccgggtttt
```

Fig. 7

CysFc dimer nucleotide sequence (mouse K$_b$ signal peptide underlined)

<u>atggagacagacacactcctgctatgggtactgctgctctggttccaggttccactggttgcccgccgtgcccagctccgg</u>
aactgctgggcggaccgtcagtcttcctcttccccccaaaacccaaggacaccctcatgatctcccggacccctgaggtc
acatgcgtggtggtggacgtgagccacgaagaccctgaggtcaagttcaactggtacgtggacggcgtggaggtgcata
atgccaagacaaagccgcgggaggagcagtacaacagcacgtaccgtgtggtcagcgtcctcaccgtcctgcaccag
gactggctgaatggcaaggagtacaagtgcaaggtctccaacaaagccctcccagcccccatcgagaaaaccatctcc
aaagccaaagggcagccccgagaaccacaggtgtacaccctgcccccatcccgggatgagctgaccaagaaccag
gtcagcctgacctgcctggtcaaaggcttctatcccagcgacatcgccgtggagtgggagagcaatgggcagccggag
aacaactacaagaccacgcctcccgtgttggactccgacggctccttcttcctctacagcaagctcaccgtggacaagag
caggtggcagcaggggaacgtcttctcatgctccgtgatgcatgaggctctgcacaaccactacacgcagaagagcctct
ccctgtctccgggtaaatga

Fig. 8

CysFc dimer amino acid sequence (mouse K$_b$ signal sequence underlined)

```
  1 METDTLLLWV LLLWVPGSTG CPPCPAPELL GGPSVFLFPP KPKDTLMISR
 51 TPEVTCVVVD VSHEDPEVKF NWYVDGVEVH NAKTKPREEQ YNSTYRVVSV
101 LTVLHQDWLN GKEYKCKVSN KALPAPIEKT ISKAKGQPRE PQVYTLPPSR
151 DELTKNQVSL TCLVKGFYPS DIAVEWESNG QPENNYKTTP PVLDSDGSFF
201 LYSKLTVDKS RWQQGNVFSC SVMHEALHNH YTQKSLSLSP GK
```

Fig. 9

HisXaCysFc nucleotide sequence (mouse K$_b$ signal sequence underlined, His tag in bold, Factor X$_a$ cleavage site in bold underlined)

<u>atggagacagacacactcctgctatgggtactgctgctctggttccaggttccactggtgac</u>catcaccatcaccatcac
ggatctggctctggatctggttcc<u>atcgaaggtcgt</u>tgcccgccgtgcccagctccggaactgctgggcggaccgtcagt
cttcctcttccccccaaaacccaaggacaccctcatgatctcccggacccctgaggtcacatgcgtggtggtggacgtgag
ccacgaagaccctgaggtcaagttcaactggtacgtggacggcgtggaggtgcataatgccaagacaaagccgcggg
aggagcagtacaacagcacgtaccgtgtggtcagcgtcctcaccgtcctgcaccaggactggctgaatggcaaggagt
acaagtgcaaggtctccaacaaagccctcccagcccccatcgagaaaaccatctccaaagccaaagggcagccccg
agaaccacaggtgtacaccctgcccccatcccgggatgagctgaccaagaaccaggtcagcctgacctgcctggtcaa
aggcttctatcccagcgacatcgccgtggagtgggagagcaatgggcagccggagaacaactacaagaccacgcctc
ccgtgttggactccgacggctccttcttcctctacagcaagctcaccgtggacaagagcaggtggcagcaggggaacgtc
ttctcatgctccgtgatgcatgaggctctgcacaaccactacacgcagaagagcctctccctgtctccgggtaaatga

Fig. 10

HisXaCysFc amino acid sequence (mouse K$_b$ signal sequence underlined, His tag in bold, Factor X$_a$ cleavage site in bold underlined)

```
  1  METDTLLLWV LLLWVPGSTG DHHHHHHGSG SGSGSIEGRC PPCPAPELLG
 51  GPSVFLFPPK PKDTLMISRT PEVTCVVVDV SHEDPEVKFN WYVDGVEVHN
101  AKTKPREEQY NSTYRVVSVL TVLHQDWLNG KEYKCKVSNK ALPAPIEKTI
151  SKAKGQPREP QVYTLPPSRD ELTKNQVSLT CLVKGFYPSD IAVEWESNGQ
201  PENNYKTTPP VLDSDGSFFL YSKLTVDKSR WQQGNVFSCS VMHEALHNHY
251  TQKSLSLSPG K
```

METHODS FOR CHEMICALLY SYNTHESIZING IMMUNOGLOBULIN CHIMERIC PROTEINS

DESCRIPTION OF THE INVENTION

This application is a divisional of U.S. patent application Ser. No. 10/842,054 filed May 6, 2004, Now U.S. Pat. No. 7,381,408, which claims priority to United States Provisional Application No. 60/469,600, filed May 6, 2003; United States Provisional Application No. 60/487,964 filed Jul. 17, 2003, and United States Provisional Application No. 60/539,207 filed Jan. 26, 2004, all of which are incorporated by reference in their entirety.

FIELD OF THE INVENTION

The invention relates to the field of chimeric proteins, e.g., proteins comprising at least a portion of an immunoglobulin constant region and a biologically active molecule. In certain specific embodiments, the invention relates to methods of chemically synthesizing chimeric proteins comprising at least a portion of an immunoglobulin constant region and a biologically active molecule.

BACKGROUND OF THE INVENTION

Chimeric proteins, e.g., proteins comprising biologically active molecules and at least a portion of an immunoglobulin constant region, possess a number of desirable attributes. These include stability, which results in longer in vivo halflife, ease of purification and ease of administration to a subject. The expression of chimeric proteins comprised of immunoglobulin constant regions linked to a protein of interest, or fragment thereof, has been described (see e.g. U.S. Pat. Nos. 5,480,981 and 5,808,029; Gascoigne et al. 1987, *Proc. Natl. Acad. Sci. USA* 84:2936; Capon et al. 1989, *Nature* 337:525; Traunecker et al. 1989, *Nature* 339:68; Zettmeissl et al. 1990, *DNA Cell Biol. USA* 9:347; Byrn et al. 1990, *Nature* 344:667; Watson et al. 1990, *J. Cell. Biol.* 110:2221; Watson et al. 1991, *Nature* 349:164; Aruffo et al. 1990, *Cell* 61:1303; Linsley et al. 1991, *J. Exp. Med.* 173:721; Linsley et al. 1991, *J. Exp. Med.* 174:561; Stamenkovic et al., 1991, *Cell* 66:1133; Ashkenazi et al. 1991, *Proc. Natl. Acad. Sci. USA* 88:10535; Lesslauer et al. 1991, *Eur. J. Immunol.* 27:2883; Peppel et al. 1991, *J. Exp. Med.* 174:1483; Bennett et al. 1991, *J. Biol hem.* 266:23060; Kurschner et al. 1992, *J. Biol. Chem.* 267:9354; Chalupny et al. 1992, *Proc. Natl. Acad. Sci. USA* 89:10360; Ridgway and Gorman, 1991, *J. Cell. Biol.* 115, Abstract No. 1448; Zheng et al. 1995, *J. Immun.* 154:5590). These proteins were all produced using recombinant technology (see, e.g., Sambrook et al. *Molecular Cloning: A Laboratory Manual,* 2 ed., Cold Spring Harbor Laboratory Press (1989); Ausubel et al. 1989, *Current Protocols in Molecular Biology,* Greene Publishing Associates and Wiley Interscience, N.Y.).

Recombinant technology provides a fast and relatively inexpensive way to produce large quantities of chimeric proteins, however the technology is not without its limitations. For example large multi-domain proteins can be difficult to express recombinantly. Recombinant expression of chimeric proteins often results in a heterogenous product requiring extensive purification. Some chimeric proteins may be toxic to cells making their expression, difficult, if not impossible. Moreover, recombinantly expressed proteins can only be comprised of the naturally occurring 20 amino acids. Thus, only L-configuration amino acids are possible using recombinant methods. Expressing chimeric proteins comprised of non-naturally occurring amino acids, provides a way to generate analogs useful in studying protein function and inhibiting undesirable metabolic pathways. Alternatively, analogs comprising non-naturally occurring amino acids may be used in some cases to enhance the activity of desirable metabolic pathways. Lastly, chimeric proteins comprising both amino acids and another biologically active molecules, e.g., nucleic acids, small molecules, are impossible to express using recombinant technology alone.

Many of the limitations described above may be overcome using chemical synthesis alone or a combination of recombinant techniques and chemical synthesis. A number of traditional techniques for chemically synthesizing proteins, such as solid phase synthesis are known in the art, see, e.g., Merrifield, 1973, *Chemical Polypeptides,* (Katsoyannis and Panayotis eds.) pp. 335-61; Merrifield 1963, *J. Am. Chem. Soc.* 85:2149; Davis et al. 1985, *Biochem. Intl.* 10:394; Finn et al. 1976, *The Proteins* (3d ed.) 2:105; Erikson et al. 1976, *The Proteins* (3d ed.) 2:257; U.S. Pat. No. 3,941,763.

Recent improvements in the chemical synthesis of proteins include the advent of native chemical ligation. As initially described, native ligation provides for the rapid synthesis of large polypeptides with a natural peptide backbone via the native chemical ligation of two or more unprotected peptide segments. In native ligation none of the reactive functionalities on the peptide segments need to be temporarily masked by a protecting group. Native ligation also allows for the solid phase sequential chemical ligation of peptide segments in an N-terminus to C-terminus direction, with the first solid phase-bound unprotected peptide segment bearing a C-terminal alpha-thioester that reacts with another unprotected peptide segment containing an N-terminal cysteine. Native chemical ligation also permits the solid-phase ligation in the C— to N-terminus direction, with temporary protection of N-terminal cysteine residues on an incoming (second) peptide segment (see, e.g., U.S. Pat. No. 6,326,468; WO 02/18417). Native ligation may also be combined with recombinant technology using intein linked to a chitin binding domain (Muir et al., 1998, *Proc. Natl. Acad. Sci. USA,* 95:6705).

Because chimeric proteins comprised of a biologically active molecule and at least a portion of an immunoglobulin constant region possess the desirable attributes described above, there remains a continual need for methods of synthesizing these chimeric proteins that is rapid and offers greater flexibility in the types of chimeric proteins produced. These needs, at least, are satisfied by certain embodiments of the invention.

SUMMARY OF THE INVENTION

The invention provides a method of chemically synthesizing chimeric proteins comprising combining at least one biologically active molecule and a portion of an immunoglobulin constant region such that a bond forms between the biologically active molecule and the portion of an immunoglobulin constant region where the biologically active molecule comprises a first functional group or moiety and the portion of an immunoglobulin constant region comprises a second functional group or moiety, and where the first and second functional group or moiety are capable of reacting with each other to form a chemical bond. In certain embodiments, the invention provides a method of chemically synthesizing chimeric proteins by performing native ligation (U.S. Pat. No. 6,184,344) such that a bond forms between at least one biologically active molecule and a portion of an immunoglobulin constant region.

In certain embodiments, the invention provides a method of synthesizing chimeric proteins comprising combining at least one biologically active molecule and at least a portion of an immunoglobulin constant region, wherein a) the portion of an immunoglobulin constant region comprises an amino (N) terminus cysteine and b) the biologically active molecule comprises a functional group capable of reacting with an N terminus cysteine to form a bond. In certain embodiments, the functional group is a thioester. In certain embodiments, e.g., where the biologically active molecule is a polypeptide, the thioester may be a carboxy (C) terminus thioester. In other embodiments, the thioester is not a carboxy thioester. In certain embodiments, the functional group is an aldehyde. In certain embodiments, e.g., where the biologically active molecule is a polypeptide, the aldehyde may be a carboxy (C) terminus aldehyde. In other embodiments, the aldehyde is not a C terminus aldehyde.

In certain embodiments, the invention provides a method of synthesizing chimeric proteins comprising the steps of a) recombinantly expressing a fusion protein comprising at least a portion of an immunoglobulin constant region and a splicing protein capable of forming a C terminus thioester on the portion of an immunoglobulin constant region; b) adding a thiol cofactor to the fusion protein of a); c) adding at least one biologically active molecule having an N terminal cysteine, thereby synthesizing the chimeric protein. In some embodiments, the splicing protein is intein or a mutant form of intein, which is defective in completion of the splicing reaction, but is still capable of thioester intermediate formation. In some embodiments, the fusion protein is further comprised of a chitin binding domain.

In certain embodiments, the chemical synthesis is performed in solution. In some embodiments, at least one of the reactants is linked to a solid support. The biologically active molecule may be linked to the solid support. The portion of an immunoglobulin constant region may be linked to a solid support. The fusion protein comprising the portion of an immunoglobulin and the splicing protein may be linked to a solid support.

It is to be understood that both the foregoing general description and the following detailed description are exemplary and explanatory only and are not restrictive of the invention, as claimed.

BRIEF DESCRIPTION OF THE DRAWINGS

FIG. 2 is the amino acid sequence of the chimeric protein Cys-Fc (SEQ ID NO:34). Included in the sequence is the signal peptide (underlined), which is cleaved by the cell resulting in the mature Cys-Fc. When this sequence is produced in CHO cells a percentage of the molecules are incorrectly cleaved by the signal peptidase such that two extra amino acids are left on the N terminus, thus preventing the linkage of a biologically active molecule with a C terminal thioester (e.g., via native ligation). When these improperly cleaved species dimerize with the properly cleaved Cys-Fc and are subsequently reacted with biologically active molecules with C terminal thioesters, monomer-dimer hybrids form.

FIG. 3 is the nucleic acid sequence of the chimeric protein Cys-Fc (SEQ ID NO:35). Included in the sequence is the signal peptide (underlined), which is cleaved by the cell after translation resulting in the mature Cys-Fc.

FIG. 5A shows the amino acid sequence of Fc MESNA (SEQ ID NO:36).

FIG. 5B shows the DNA sequence of Fc MESNA (SEQ ID NO:37).

FIG. 7 shows CysFc dimer nucleotide sequence (SEQ ID NO:38) (mouse $K_b$ signal peptide underlined).

FIG. 8 shows CysFc dimer amino acid sequence (SEQ ID NO:39) (mouse $K_b$ signal sequence underlined).

FIG. 9 shows HisXaCysFc nucleotide sequence (SEQ ID NO:40) (mouse $K_b$ signal sequence underlined, His tag in bold, Factor $X_a$ cleavage site in bold underlined.

FIG. 10 shows HisXaCysFc amino acid sequence (SEQ ID NO:41) (mouse $K_b$ signal sequence underlined, His tag in bold, Factor $X_a$ cleavage site in bold underlined).

DESCRIPTION OF THE EMBODIMENTS

A. Definitions

Figure 1:
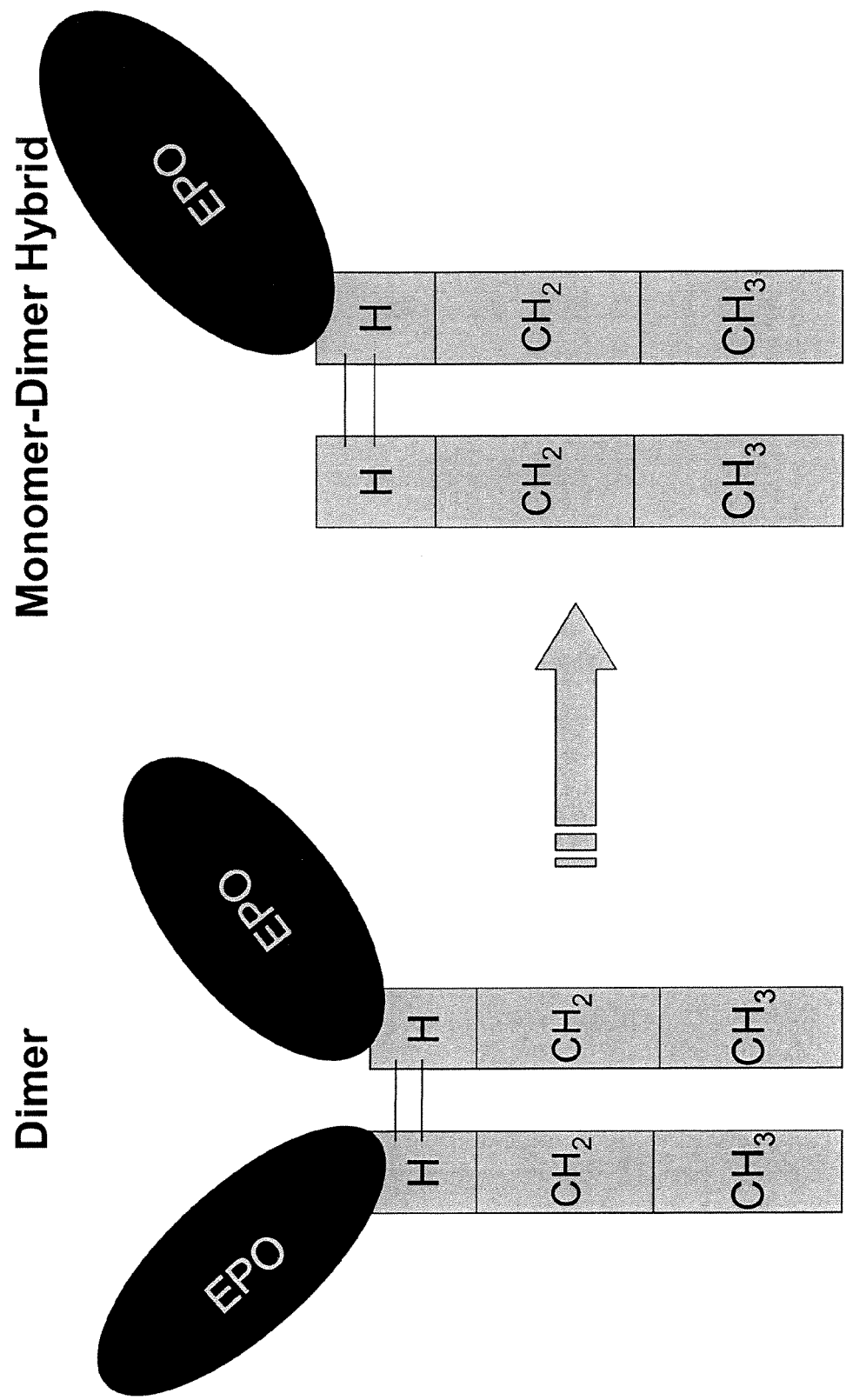
FIG. 1 is a schematic diagram comparing the structure of an EPO-Fc homodimer, or dimer, and the structure of an Epo-FC monomer-dimer hybrid.

Affinity tag, as used herein, means a molecule attached to a second molecule of interest, capable of interacting with a specific binding partner for the purpose of isolating or identifying said second molecule of interest.

Analogs of chimeric proteins of the invention, or proteins or peptides substantially identical to the chimeric proteins of the invention, as used herein, means that a relevant amino acid sequence of a protein or a peptide is at least 70%, 75%, 80%, 85%, 90%, 95%, 97%, 98%, 99%, or 100% identical to a given sequence. By way of example, such sequences may be variants derived from various species, or they may be derived from the given sequence by truncation, deletion, amino acid substitution or addition. Percent identity between two amino acid sequences is determined by standard alignment algorithms such as, for example, Basic Local Alignment Tool (BLAST) described in Altschul et al. 1990, *J. Mol. Biol.*, 215:403-410, the algorithm of Needleman et al. 1970, *J. Mol. Biol.*, 48:444-453; the algorithm of Meyers et al. 1988, *Comput. Appl. Biosci.*, 4:11-17; or Tatusova et al. 1999, *FEMS Microbiol. Lett.*, 174:247-250, etc. Such algorithms are incorporated into the BLASTN, BLASTP and "BLAST 2 Sequences" programs (see www.ncbi.nlm.nih.gov/BLAST). When utilizing such programs, the default parameters can be used. For example, for nucleotide sequences the following settings can be used for "BLAST 2 Sequences": program BLASTN, reward for match 2, penalty for mismatch −2, open gap and extension gap penalties 5 and 2 respectively, gap x_dropoff 50, expect 10, word size 11, filter ON. For amino acid sequences the following settings can be used for "BLAST 2 Sequences": program BLASTP, matrix BLOSUM62, open gap and extension gap penalties 11 and 1 respectively, gap x_dropoff 50, expect 10, word size 3, filter ON.

Bioavailability, as used herein, means the extent and rate at which a substance is absorbed into a living system or is made available at the site of physiological activity.

Biologically active molecule, as used herein, means a non-immunoglobulin molecule or fragment thereof, capable of treating a disease or condition or localizing or targeting a molecule to a site of a disease or condition in the body by performing a function or an action, or stimulating or responding to a function, an action or a reaction, in a biological context (e.g. in an organism, a cell, or an in vitro model thereof). Biologically active molecules may comprise at least one of polypeptides, nucleic acids; small molecules such as small organic or inorganic molecules.

A chimeric protein, as used herein, refers to any protein comprised of a first amino acid sequence derived from a first source, bonded, covalently or non-covalently, to a second amino acid sequence derived from a second source, wherein the first and second source are not the same. A first source and a second source that are not the same can include two different biological entities, or two different proteins from the same biological entity, or a biological entity and a non-biological entity. A chimeric protein can include for example, a protein derived from at least 2 different biological sources. A biological source can include any non-synthetically produced nucleic acid or amino acid sequence (e.g. a genomic or cDNA sequence, a plasmid or viral vector, a native virion or a mutant or analog, as further described herein, of any of the above). A synthetic source can include a protein or nucleic acid sequence produced chemically and not by a biological system (e.g. solid phase synthesis of amino acid sequences). A chimeric protein can also include a protein derived from at least 2 different synthetic sources or a protein derived from at least one biological source and at least one synthetic source. A chimeric protein may also comprise a first amino acid sequence derived from a first source, covalently or non-covalently linked to a nucleic acid, derived from any source or a small organic or inorganic molecule derived from any source. The chimeric protein may comprise a linker molecule between the first and second amino acid sequence or between the first amino acid sequence and the nucleic acid, or between the first amino acid sequence and the small organic or inorganic molecule.

Clotting factor, as used herein, means any molecule, or analog thereof, naturally occurring or recombinantly produced which prevents or decreases the duration of a bleeding episode in a subject with a hemostatic disorder. In other words, it means any molecule having clotting activity.

Clotting activity, as used herein, means the ability to participate in a cascade of biochemical reactions that culminates in the formation of a fibrin clot and/or reduces the severity, duration or frequency of hemorrhage or bleeding episode.

Dimer, as used herein, refers to a chimeric protein comprising a first and second polypeptide chain, wherein the first and second chains both comprise a biologically active molecule, and at least a portion of an immunoglobulin constant region. A homodimer refers to a dimer where both biologically active molecules are the same.

Figure 4:
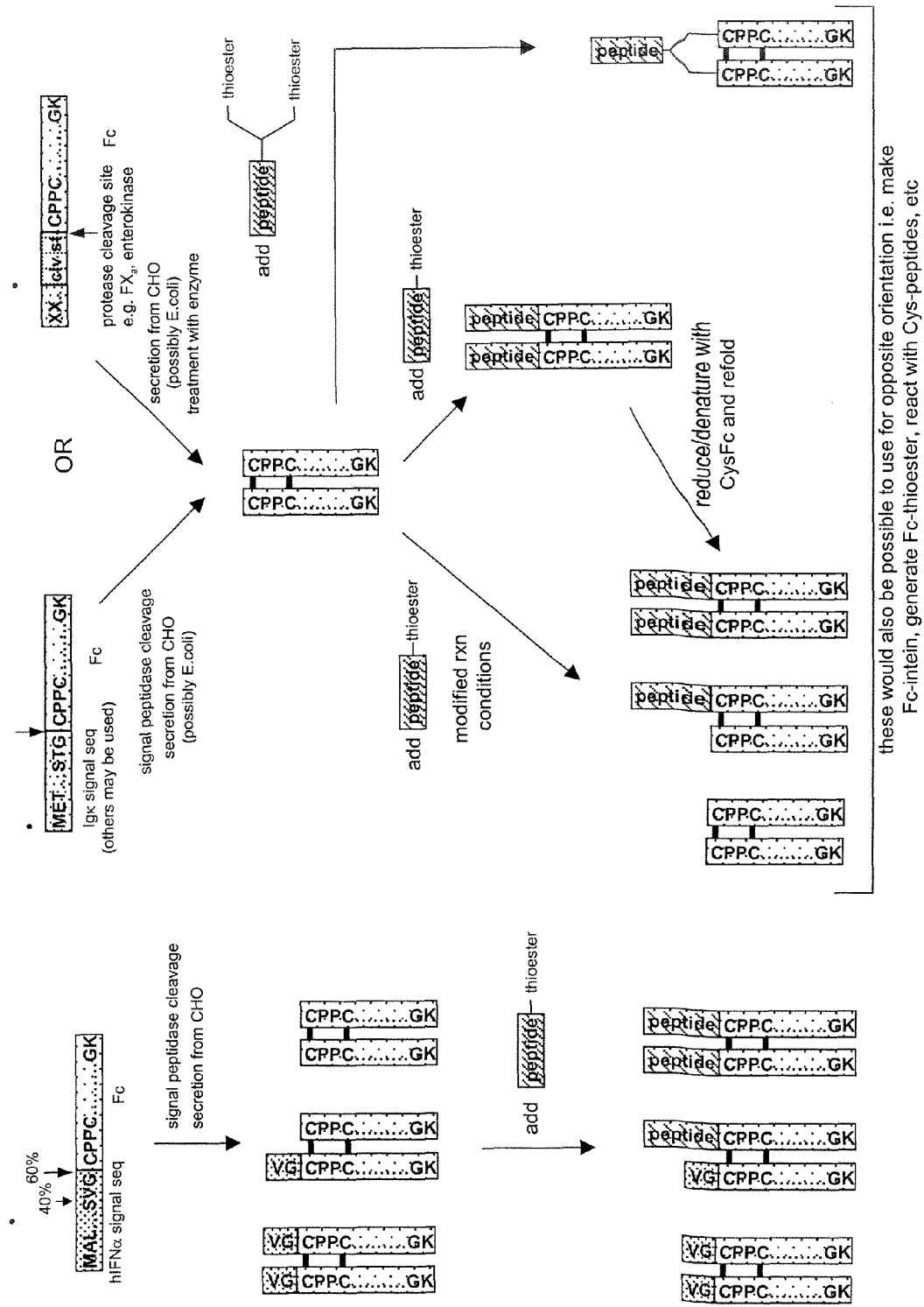
FIG. 4 demonstrates ways to form monomer-dimer hybrids through native ligation.

Dimerically linked monomer-dimer hybrid refers to a chimeric protein comprised of at least a portion of an immunoglobulin constant region, e.g. an Fc fragment of an immunoglobulin, a biologically active molecule and a linker which links the two together such that one biologically active molecule is bound to 2 polypeptide chains, each comprising a portion of an immunoglobulin constant region. FIG. 4 shows an example of a dimerically linked monomer-dimer hybrid.

DNA construct, as used herein, means a DNA molecule, or a clone of such a molecule, either single- or double-stranded that has been modified through human intervention to contain segments of DNA combined in a manner that as a whole would not otherwise exist in nature. DNA constructs contain the information necessary to direct the expression of polypeptides of interest. DNA constructs can include promoters, enhancers and transcription terminators. DNA constructs containing the information necessary to direct the secretion of a polypeptide will also contain at least one secretory signal sequence.

Domain, as used herein, means a region of a polypeptide (including proteins as that term is defined) having some distinctive physical feature or role including for example an independently folded structure composed of one section of a polypeptide chain. A domain may contain the sequence of the distinctive physical feature of the polypeptide or it may contain a fragment of the physical feature which retains its binding characteristics (i.e. it can bind to a second domain). A domain may be associated with another domain. In other words, a first domain may naturally bind to a second domain.

A fragment, as used herein, refers to a peptide or polypeptide comprising an amino acid sequence of at least 2 contiguous amino acid residues, of at least 5 contiguous amino acid residues, of at least 10 contiguous amino acid residues, of at least 15 contiguous amino acid residues, of at least 20 contiguous amino acid residues, of at least 25 contiguous amino acid residues, of at least 40 contiguous amino acid residues, of at least 50 contiguous amino acid residues, of at least 100 contiguous amino acid residues, or of at least 200 contiguous amino acid residues or any deletion or truncation of a protein, peptide, or polypeptide.

Hemostasis, as used herein, means the stoppage of bleeding or hemorrhage; or the stoppage of blood flow through a blood vessel or body part.

Hemostatic disorder, as used herein, means a genetically inherited or acquired condition characterized by a tendency to hemorrhage, either spontaneously or as a result of trauma, due to an impaired ability or inability to form a fibrin clot.

Linked, as used herein, refers to a first nucleic acid sequence covalently joined to a second nucleic acid sequence. The first nucleic acid sequence can be directly joined or juxtaposed to the second nucleic acid sequence or alternatively an intervening sequence can covalently join the first sequence to the second sequence. Linked, as used herein, can also refer to a first amino acid sequence covalently, or non-covalently, joined to a second amino acid sequence. The first amino acid sequence can be directly joined or juxtaposed to the second amino acid sequence or alternatively an intervening sequence can covalently join the first amino acid sequence to the second amino acid sequence. Linked as used herein can also refer to a first amino acid sequence covalently joined to a nucleic acid sequence or a small organic or inorganic molecule.

Native ligation, as used herein, refers to the chemoselective reaction of unprotected or N-terminal cysteine protected peptide segments with another unprotected peptide segment resulting in the formation of a ligated polypeptide with an amide bond at the ligation site. A polypeptide assembled by native ligation may comprise one, two or more native ligation sites.

Operatively linked, as used herein, means a first nucleic acid sequence linked to a second nucleic acid sequence such that both sequences are capable of being expressed as a biologically active protein or peptide.

Polypeptide, as used herein, refers to a polymer of amino acids and does not refer to a specific length of the product; thus, peptides, oligopeptides, and proteins are included within the definition of polypeptide. This term does not exclude post-expression modifications of the polypeptide, for example, glycosylation, acetylation, phosphorylation, pegylation, addition of a lipid moiety, or the addition of any organic or inorganic molecule. Included within the definition, are for example, polypeptides containing one or more analogs of an amino acid (including, for example, unnatural amino acids) and polypeptides with substituted linkages, as well as other modifications known in the art, both naturally occurring and non-naturally occurring.

High stringency, as used herein, includes conditions readily determined by the skilled artisan based on, for example, the length of the DNA. Generally, such conditions are defined in Sambrook et al. *Molecular Cloning: A Laboratory Manual*, 2 ed. Vol. 1, pp. 1.101-104, Cold Spring Harbor Laboratory Press (1989), and include use of a prewashing solution for the nitrocellulose filters 5×SSC, 0.5% SDS, 1.0 mM EDTA (PH 8.0), hybridization conditions of 50% formamide, 6×SSC at 42° C. (or other similar hybridization solution, such as Stark's solution, in 50% formamide at 42° C., and with washing at approximately 68° C., 0.2× SSC, 0.1% SDS. The skilled artisan will recognize that the temperature and wash solution salt concentration can be adjusted as necessary according to factors such as the length of the probe.

Moderate stringency, as used herein, include conditions that can be readily determined by those having ordinary skill in the art based on, for example, the length of the DNA. The basic conditions are set forth by Sambrook et al. *Molecular Cloning: A Laboratory Manual*, 2d ed. Vol. 1, pp. 1.101-104, Cold Spring Harbor Laboratory Press (1989), and include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

A small inorganic molecule, as used herein means a molecule containing no carbon atoms and being no larger than 50 kD.

A small organic molecule, as used herein means a molecule containing at least one carbon atom and being no larger than 50 kD.

Thioester, as use herein, refers to a moiety represented by —COSR. The R group may be any number of groups, including 1-15 C functionalized alkyl, straight or branched, 1-15 C aromatic structures, 1-100 amino acids. Thioester is intended to be interchangeable with the IUPAC term thioloester.

Treat, treatment, treating, as used herein, means any of the following: the reduction in severity of a disease or condition; the reduction in the duration of a disease course; the amelioration of one or more symptoms associated with a disease or condition; the provision of beneficial effects to a subject with a disease or condition, without necessarily curing the disease or condition, the prophylaxis of one or more symptoms associated with a disease or condition.

B. Synthesis of Chimeric Proteins

Chimeric proteins comprising at least a portion of an immunoglobulin constant region and a biologically active molecule can be synthesized using techniques well known in the art. For example, the chimeric proteins of the invention may be synthesized recombinantly in cells (see e.g. Sambrook et al. 1989, *Molecular Cloning A Laboratory Manual*, Cold Spring Harbor Laboratory, N.Y. and Ausubel et al. 1989, *Current Protocols in Molecular Biology*, Greene Publishing Associates and Wiley Interscience, N.Y.). Alternatively, the chimeric proteins of the invention may be synthesized using known synthetic methods such as native ligation (U.S. Pat. No. 6,326,468) or solid phase synthesis (see e.g. Merrifield, 1973, *Chemical Polypeptides*, (Katsoyannis and Panayotis eds.) pp. 335-61; Merrifield 1963, *J. Am. Chem. Soc.* 85:2149; Davis et al. 1985, *Biochem. Intl.* 10:394; Finn et al. 1976, *The Proteins* (3d ed.) 2:105; Erikson et al. 1976, *The Proteins* (3d ed.) 2:257; U.S. Pat. No. 3,941,763. Alternatively, the chimeric proteins of the invention may be synthesized using a combination of recombinant and synthetic methods. In certain applications, it may be beneficial to use either a recombinant method or a combination of recombinant and synthetic methods.

Combining recombinant and chemical synthesis allows for the rapid screening of biologically active molecules and linkers to optimize desired properties of the chimeric protein of the invention, e.g., viral inhibition, hemostasis, production of red blood cells, biological half-life, stability, binding to serum proteins or some other property of the chimeric protein. The method also allows for the incorporation of non-natural amino acids into the chimeric protein of the invention which may be useful for optimizing a desired property of the chimeric protein of the invention.

1. Chemical Synthesis

In certain embodiments, the invention provides a method of synthesizing a chimeric protein of the invention comprising at least one biologically active molecule and at least a portion of an immunoglobulin constant region, or fragment thereof, where one of either the biologically active molecule or the portion of an immunoglobulin constant region may comprise an N terminus cysteine and the other comprises a functional group capable of reacting specifically with the N terminal cysteine. The biologically active molecule may include a polypeptide. The biologically active molecule may include a small organic molecule or a small inorganic molecule. The biologically active molecule include a nucleic acid.

In one embodiment, the N terminal cysteine is on the portion of an immunoglobulin constant region. In one embodiment, the portion of an immunoglobulin constant region is an Fc fragment. The Fc fragment can be recombinantly produced to form cysteine-Fc (Cys-Fc) and reacted with at least one biologically active molecule expressing a thioester to make a chimeric protein of the invention, e.g., monomer-dimer hybrid (FIG. 4). In another embodiment, an Fc-thioester is made and reacted with at least one biologically active molecule expressing an N terminus cysteine.

In one embodiment, the N-terminal cysteine may be on the portion of an immunoglobulin constant region, e.g., an Fc fragment. An Fc fragment can be generated with an N-terminal cysteine by taking advantage of the fact that a native Fc has a cysteine at positions 220, 226 and 229 (see Kabat et al. 1991, *Sequences of Proteins of Immunological Interest*, U.S. Department of Public Health, Bethesda, Md.). Any of these cysteines may be used to generate an Fc fragment for use in the methods described herein. Additionally, recombinant techniques can be used to generate Fc fragments having at least one non-native (i.e. engineered by humans) N terminus cysteine. For example, cysteines can be added on at positions higher than 226, or lower than 220, of the EU numbering system.

In a specific embodiment, an Fc fragment is expressed with the human a interferon signal peptide adjacent to the Cys at position 226. When a construct encoding this polypeptide is expressed in CHO cells, the CHO cells cleave the signal peptide at two distinct positions (at Cys 226 and at Val within the signal peptide 2 amino acids upstream in the N terminus direction). This generates a mixture of two species of Fc fragments (one with an N-terminal Val and one with an N-terminal Cys). This in turn results in a mixture of dimeric species (homodimers with terminal Val, homodimers with terminal Cys and heterodimers where one chain has a terminal Cys and the other chain has a terminal Val) (FIG. 4A). The Fc fragments can be reacted with at least one biologically active molecule having a C terminal thioester and the resulting monomer-dimer hybrid or dimer can be isolated from the mixture (e.g. by size exclusion chromatography). It is contemplated that when other signal peptide sequences are used for expression of Fc fragments in CHO cells a mixture of species of Fc fragments with at least two different N termini will be generated.

Cys-Fc may be recombinantly expressed. In one embodiment, the Fc fragment is expressed in a prokaryotic cell, e.g., *E. coli*. The sequence encoding the Fc portion beginning with Cys 226 (EU numbering) can be placed immediately following a sequence encoding a signal peptide, e.g., OmpA, PhoA, STII. The prokaryotic cell can be osmotically shocked to release the recombinant Fc fragment. In another embodiment, the Fc fragment is produced in a eukaryotic cell, e.g., a CHO cell, a BHK cell. The sequence encoding the Fc portion fragment can be placed directly following a sequence encoding a signal peptide, e.g., mouse Igκ light chain or MHC class I Kb signal sequence, such that when the recombinant chimeric protein is synthesized by a eukaryotic cell, the signal sequence will be cleaved, leaving an N terminal cysteine which can than be isolated and chemically reacted with a molecule bearing a thioester (e.g. a C terminal thioester if the molecule is comprised of amino acids).

The N terminal cysteine on an Fc fragment can also be generated using an enzyme that cleaves its substrate at its N terminus, e.g., Factor $X^a$, enterokinase, and the product isolated and reacted with a molecule with a thioester.

In some embodiments, a recombinantly produced Cys-Fc can form a homodimer. The homodimer may be reacted with peptide that has a branched linker on the C terminus, wherein the branched linker has two C terminal thioesters that can be reacted with the Cys-Fc, thus forming a dimerically linked monomer dimer hybrid (FIG. 4). In another embodiment, the biologically active molecule may have a single non-terminal thioester that can be reacted with Cys-Fc.

In some embodiments, the branched linker can have two C terminal cysteines that can be reacted with an Fc thioester. In another embodiment, the branched linker has two functional groups that can be reacted with the Fc thioester, e.g., 2-mercaptoamine.

Where the portion of the immunoglobulin constant region has an N terminus cysteine, the functional group on the biologically active molecule may be an aldehyde. If necessary, the aldehyde functionality can be chemically synthesized for example by oxidation of an N-terminal serine with periodate (see, e.g., Georghagen et al., 1992, *Bioconjugate Chem.* 3:138). Alternatively, where the biologically active molecule is a DNA molecule, it may labeled with an aldehyde group by first coupling the DNA, during the last round of synthesis, with phosphoramidite thus generating a protected amine. After deprotection, the DNA molecule labeled with a free amine may be generated. The amine could be coupled to succinimidyl 4-formylbenzoate (as shown below) to generate the aldehyde. This could be done on either its 3' or 5' end.

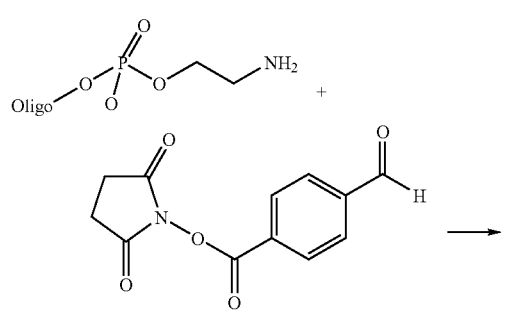

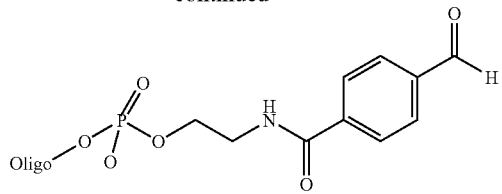

Another way of introducing an aldehyde into an oligonucleotide is described in Zatsepin et al., 2002, *Bioconjugate Chem*, 13:822. A protected 1,2-diol may be incorporated in the 2' position. After the synthesis of the oligo, the protecting groups can be removed to reveal the free 1,2-diol, which can then be oxidized with periodate to give an aldehyde.

Aldehydes are known to react with N-terminal cysteines (in effect, a 1,2-amino thiol moiety) to form thiazolidines. (See Botti, 1996, *J. Am. Chem. Soc.*, 118:10018; Zhang et al., 1998, *Proc. Nat. Acad. Sci. USA*, 95:9184). In one embodiment, the portion of an immunoglobulin constant region is an Fc fragment with an N terminus cysteine (CysFc). CysFc can thus react selectively with any aldehyde to form this linkage site-specifically at the N-terminus.

In another embodiment, where the immunoglobulin constant region has an N terminus cysteine, the functional group on the biologically active molecule may be a thioester. In certain embodiments, the thioester may be a C terminus thioester. When the biologically active molecule comprising the thioester is combined with the portion of an immunoglobulin comprising an N terminus cysteine nucleophilic substitution occurs and yields a thioester-linked intermediate which spontaneously undergoes rearrangement to form a native amide bond at the ligation site.

Nucleic acids, e.g., DNA, RNA may be chemically synthesized to provide one thioester, see McPherson et al. 1999, *Synlett*. S1:978. The nucleic acid can be coupled with a thiophosphate at the 5' end and then reacted with bromo-acetylated thioester to generate a 5' thioester. The 5' thioester could in turn be reacted with a portion of an immunoglobulin constant region comprising an N terminus cysteine, e.g., Cys-Fc.

In certain embodiments, the invention provides a method of synthesizing chimeric proteins that combines chemical synthesis with recombinant synthesis (described below). Thus, the biologically active molecule may be synthesized chemically or recombinantly. Similarly, the portion of the immunoglobulin may be synthesized chemically or recombinantly. Once both individual components are synthesized they may be combined chemically to synthesize the chimeric protein of the invention.

A combination of chemical and recombinant synthesis may be used where it is desirable to link a biologically active molecule to the C terminus of a portion of an immunoglobulin. In this embodiment, the portion of an immunoglobulin constant region, e.g., the Fc region, is expressed as a fusion protein comprising a protein splicer which forms a thioester intermediate, e.g., intein, linked to the C terminus of the portion of an immunoglobulin constant region. Commercially available vectors (PCYB2-IMPACT) (New England Biolabs, Beverly, Mass.) provide a cloning cite adjacent to a mutant form of intein which is upstream of a chitin binding domain. The mutant intein does not splice the fusion protein, but does form the thioester intermediate. In one embodiment, the portion of the immunoglobulin with the intein linked to its C terminus can be expressed in a prokaryotic cell. In another embodiment, the portion of the immunoglobulin with the intein linked to its C terminus can be expressed in a eukaryotic cell. The fusion protein may be isolated using chitin linked to a solid support. Addition of a thiol co-factor, such as thiophenol or MESNA, and a biologically active molecule with a N-terminus cysteine allows for the linkage of a biologically active molecule to the C terminus thioester of the portion of an immunoglobulin. The biologically active molecule and portion of an immunoglobulin may be reacted together such that nucleophilic rearrangement occurs and the biologically active molecule is covalently linked to the portion of an immunoglobulin via an amide bond. (Dawsen et al. 2000, *Annu. Rev. Biochem.* 69:923).

Where the biological molecule of interest is a nucleic acid molecule, e.g., a DNA molecule, phosphoramidite can be used to introduce a terminal cysteine residue to the DNA. The DNA can then be linked to the Fc-thioester generated as described above.

Chemical synthesis may be used to synthesize any of the chimeric proteins of the invention, including monomer-dimer hybrids, dimers and dimerically linked monomer-dimer hybrids. Chemical synthesis may be used to synthesize a chimeric protein of the invention comprising any biologically active molecule including a polypeptide, a nucleic acid, or a small molecule. In some embodiments, chemical synthesis may be used to synthesize a chimeric protein comprising an Fc fragment of an immunoglobulin.

In one embodiment, the portion of an immunoglobulin constant region ligated to the biologically active molecule will form homodimers. The homodimers may be isolated. Alternatively, the homodimers can be disrupted by exposing the homodimers to denaturing and reducing conditions (e.g. beta-mercaptoethanol and 8 M urea) and then subsequently combined with a portion of an immunoglobulin constant region not linked to a biologically active molecule to form monomer-dimer hybrids. The monomer-dimer hybrids are then renatured and refolded by dialyzing into PBS and isolated, e.g., by size exclusion or affinity chromatography.

In another embodiment, the portion of an immunoglobulin constant region will form homodimers before being linked to a biologically active molecule. In this embodiment, reaction conditions for linking the biologically active molecule to the homodimer can be adjusted such that linkage of the biologically active molecule to only one chain of the homodimer is favored (e.g. by adjusting the molar equivalents of each reactant).

The chimeric protein chemically synthesized can optionally include a linker peptide between the portion of an immunoglobulin and the biologically active molecule. Any linker known in the art may be used. The linker may for example be linked to the N terminus of the biologically active molecule, where the biologically active molecule is a polypeptide. Linkers can include peptides and/or organic molecules (e.g. polyethylene glycol and/or short amino acid sequences). The linker may be a branching molecule that facilitates the bonding of multiple copies of the biologically active molecule to the portion of an immunoglobulin constant region. Alternatively, the linker may be a branching molecule that facilitates the bonding of one biologically active molecule to more than one portion of an immunoglobulin constant region.

Any of the chemical synthesis techniques described herein can be performed by linking at least one of the biologically active molecule and the portion of an immunoglobulin constant region to a solid support. As an example an amino-Spherilose™ (Isco, Lincoln, NB) may be derivatized with Boc-aminooxyacetic acid. Other resins which may be used as the solid support include EAH Sepharose (Pharmacia, NY, N.Y.), Amino PEGA (Novabiochem, San Diego, Calif.), CLEAR base resin (Peptides International, Louisville, Ky.), long chain alkylamine controlled pore glass (Sigma, St. Louis, Mo.), HCl.PEG polystyrene (PerSeptive Biosystems, Waltham, Mass.), Lysine Hyper D resin (Biosepra, Freemont, Calif.), ArgoGel Base resin (Argonaut Technologies, Foster City, Calif.). These resins are available in amino-derivatized form or are readily converted to an amino-derivatized form to facilitate coupling.

2. Recombinant Synthesis

Nucleic acids encoding a biologically active molecule can be readily synthesized using recombinant techniques well known in the art. Alternatively, the peptides themselves can be chemically synthesized. Nucleic acids of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. 1988, *Nucl. Acids Res.* 16:3209, methylphosphonate oligonucleotides can be prepared by use of controlled pore glass polymer supports as described in Sarin et al. 1988, *Proc. Natl. Acad. Sci. USA* 85:7448. Additional methods of nucleic acid synthesis are known in the art. (see e.g. U.S. Pat. Nos. 6,015,881; 6,281,331; 6,469,136).

DNA sequences encoding immunoglobulin constant regions, or fragments thereof, may be cloned from a variety of genomic or cDNA libraries known in the art. The techniques for isolating such DNA sequences using probe-based methods are conventional techniques and are well known to those skilled in the art. Probes for isolating such DNA sequences may be based on published DNA sequences (see, e.g., Hieter et al. 1980, *Cell* 22:197-207). The polymerase chain reaction (PCR) method disclosed by Mullis et al. (U.S. Pat. No. 4,683,195) and Mullis (U.S. Pat. No. 4,683,202) may be used. The choice of library and selection of probes for the isolation of such DNA sequences is within the level of ordinary skill in the art. Alternatively, DNA sequences encoding immunoglobulins or fragments thereof can be obtained from vectors known in the art to contain immunoglobulins or fragments thereof.

For recombinant production, a first polynucleotide sequence encoding a portion of the chimeric protein of the invention (e.g. a portion of an immunoglobulin constant region) and a second polynucleotide sequence encoding a portion of the chimeric protein of the invention (e.g. a portion of an immunoglobulin constant region and a biologically active molecule) are inserted into appropriate expression vehicles, i.e. vectors which contains the necessary elements for the transcription and translation of the inserted coding sequence, or in the case of an RNA viral vector, the necessary elements for replication and translation. The nucleic acids encoding the chimeric protein are inserted into the vector in proper reading frame.

The expression vehicles are then transfected or co-transfected into a suitable target cell, which will express the polypeptides. Transfection techniques known in the art include, but are not limited to, calcium phosphate precipitation (Wigler et al. 1978, *Cell* 14:725) and electroporation (Neumann et al. 1982, *EMBO, J.* 1:841), and liposome based reagents. A variety of host-expression vector systems may be utilized to express the chimeric proteins described herein including both prokaryotic or eukaryotic cells. These include, but are not limited to, microorganisms such as bacteria (e.g. *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g. baculovirus) containing an appropriate coding sequence; plant cell systems infected with recombinant virus expression vectors (e.g. cauliflower mosaic virus or tobacco mosaic virus) or transformed with recombinant plasmid expression vectors (e.g. Ti plasmid) containing an appropriate coding sequence; or animal cell systems, including mammalian cells (e.g. CHO, Cos, HeLa cells).

When the chimeric protein of the invention is recombinantly synthesized in a prokaryotic cell it may be desirable to refold the chimeric protein. The chimeric protein produced by this method can be refolded to a biologically active conformation using conditions known in the art, e.g., reducing conditions and then dialyzed slowly into PBS.

Depending on the expression system used, the expressed chimeric protein is then isolated by procedures well-established in the art (e.g. affinity chromatography, size exclusion chromatography, ion exchange chromatography).

The expression vectors can encode for tags that permit for easy purification of the recombinantly produced chimeric protein. Examples include, but are not limited to vector pUR278 (Ruther et al. 1983, *EMBO J.* 2:1791) in which the chimeric protein described herein coding sequences may be ligated into the vector in frame with the lac z coding region so that a hybrid protein is produced; pGEX vectors may be used to express chimeric proteins of the invention with a glutathione S-transferase (GST) tag. These proteins are usually soluble and can easily be purified from cells by adsorption to glutathione-agarose beads followed by elution in the presence of free glutathione. The vectors include cleavage sites (thrombin or Factor $X_a$ protease or PreScission Protease™ (Pharmacia, Peapack, N.J.)) for easy removal of the tag after purification.

To increase efficiency of production, the polynucleotides can be designed to encode multiple units of the chimeric protein of the invention separated by enzymatic cleavage sites. The resulting polypeptide can be cleaved (e.g. by treatment with the appropriate enzyme) in order to recover the polypeptide units. This can increase the yield of polypeptides driven by a single promoter. When used in appropriate viral expression systems, the translation of each polypeptide encoded by the mRNA is directed internally in the transcript; e.g., by an internal ribosome entry site, IRES. Thus, the polycistronic construct directs the transcription of a single, large polycistronic mRNA which, in turn, directs the translation of multiple, individual polypeptides. This approach eliminates the production and enzymatic processing of polypeptides and may significantly increase yield of polypeptide driven by a single promoter.

Vectors used in transformation will usually contain a selectable marker used to identify transformants. In bacterial systems, this can include an antibiotic resistance gene such as ampicillin or kanamycin. Selectable markers for use in cultured mammalian cells include genes that confer resistance to drugs, such as neomycin, hygromycin, and methotrexate. The selectable marker may be an amplifiable selectable marker. One amplifiable selectable marker is the DHFR gene. Another amplifiable marker is the DHFR cDNA (Simonsen and Levinson 1983, *Proc. Natl. Acad. Sci. USA* 80:2495). Selectable markers are reviewed by Thilly (*Mammalian Cell Technology*, Butterworth Publishers, Stoneham, Mass.) and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, U.S. Pat. No. 4,713,339).

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g. heat shock promoters; the promoter for the small subunit of RUBISCO; the promoter for the chlorophyll a/b binding protein) or from plant viruses (e.g. the 35S RNA promoter of CaMV; the coat protein promoter of TMV) may be used; when cloning in mammalian cell systems, promoters derived from the genome of mammalian cells (e.g. metallothionein promoter) or from mammalian viruses (e.g. the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding linear or non-cyclized forms of the chimeric proteins of the invention may be driven by any of a number of promoters. For example, viral promoters such as the 35S RNA and 19S RNA promoters of CaMV (Brisson et al. 1984, *Nature* 310:511-514), or the coat protein promoter of TMV (Takamatsu et al. 1987, *EMBO J.* 6:307-311) may be used; alternatively, plant promoters such as the small subunit of RUBISCO (Coruzzi et al. 1984, *EMBO J.* 3:1671-1680; Broglie et al. 1984, *Science* 224:838-843) or heat shock promoters, e.g., soybean hsp17.5-E or hsp17.3-B (Gurley et al. 1986, *Mol. Cell. Biol.* 6:559-565) may be used. These constructs can be introduced into plant cells using Ti plasmids, Ri plasmids, plant virus vectors, direct DNA transformation, microinjection, electroporation, etc. For reviews of such techniques see e.g. Weissbach & Weissbach 1988, *Methods for Plant Molecular Biology*, Academic Press, NY, Section VIII, pp. 421-463; and Grierson & Corey 1988, *Plant Molecular Biology*, 2d Ed., Blackie, London, Ch. 7-9.

In one insect expression system that may be used to produce the chimeric proteins of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example, the polyhedron gene) of the virus and placed under control of an AcNPV promoter (for example, the polyhedron promoter). Successful insertion of a coding sequence will result in inactivation of the polyhedron gene and production of non-occluded recombinant virus (i.e. virus lacking the proteinaceous coat coded for by the polyhedron gene). These recombinant viruses are then used to infect *Spodoptera frugiperda* cells in which the inserted gene is expressed. (see e.g. Smith et al. 1983, *J. Virol.* 46:584; U.S. Pat. No. 4,215,051). Further examples of this expression system may be found in Ausubel et al., eds. 1989, *Current Protocols in Molecular Biology*, Vol. 2, Greene Publish. Assoc. & Wiley Interscience.

Another system which can be used to express the chimeric proteins of the invention is the glutamine synthetase gene expression system, also referred to as the "GS expression system" (Lonza Biologics PLC, Berkshire UK). This expression system is described in detail in U.S. Pat. No. 5,981,216.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g. region E1 or E3) will result in a recombinant virus that is viable and capable of expressing peptide in infected hosts (see e.g. Logan & Shenk 1984, *Proc. Natl. Acad. Sci. USA* 81:3655). Alternatively, the vaccinia 7.5 K promoter may be used (see e.g. Mackett et al. 1982, *Proc. Natl. Acad. Sci. USA* 79:7415; Mackett et al. 1984, *J. Virol.* 49:857; Panicali et al. 1982, *Proc. Natl. Acad. Sci. USA* 79:4927).

In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g. region E1 or E3) will result in a recombinant virus that is viable and capable of expressing peptide in infected hosts (see e.g. Logan & Shenk 1984, *Proc. Natl. Acad. Sci. USA* 81:3655). Alternatively, the vaccinia 7.5 K promoter may be used (see e.g. Mackett et al. 1982, *Proc. Natl. Acad. Sci. USA* 79:7415; Mackett et al. 1984, *J. Virol.* 49:857; Panicali et al. 1982, *Proc. Natl. Acad. Sci. USA* 79:4927).

Host cells containing DNA constructs of the chimeric protein are grown in an appropriate growth medium. As used herein, the term "appropriate growth medium" means a medium containing nutrients required for the growth of cells. Nutrients required for cell growth may include a carbon source, a nitrogen source, essential amino acids, vitamins, minerals and growth factors. Optionally the media can contain bovine calf serum or fetal calf serum. In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g. MEM, DMEM). Selection of a medium appropriate for the particular cell line used is within the level of ordinary skill in the art.

The recombinantly produced chimeric protein of the invention can be isolated from the culture media. The culture medium from appropriately grown transformed or transfected host cells is separated from the cell material, and the presence of chimeric proteins is demonstrated. One method of detecting the chimeric proteins, for example, is by the binding of the chimeric proteins or portions of the chimeric proteins to a specific antibody recognizing the chimeric protein of the invention. An anti-chimeric protein antibody may be a monoclonal or polyclonal antibody raised against the chimeric protein in question. For example, the chimeric protein contains at least a portion of an immunoglobulin constant region. Antibodies recognizing the constant region of many immunoglobulins are known in the art and are commercially available. An antibody can be used to perform an ELISA or a western blot to detect the presence of the chimeric protein of the invention.

The chimeric protein of the invention can be synthesized in a transgenic animal, such as a rodent, cow, pig, sheep, or goat. The term "transgenic:animals" refers to non-human animals that have incorporated a foreign gene into their genome. Because this gene is present in germline tissues, it is passed from parent to offspring. Exogenous genes are introduced into single-celled embryos (Brinster et al. 1985, *Proc. Natl. Acad. Sci. USA* 82:4438). Methods of producing transgenic animals are known in the art, including transgenics that produce immunoglobulin molecules (Wagner et al. 1981, *Proc. Natl. Acad. Sci. USA* 78:6376; McKnight et al. 1983, *Cell* 34:335; Brinster et al. 1983, *Nature* 306:332; Ritchie et al. 1984, *Nature* 312:517; Baldassarre et al. 2003, *Theriogenology* 59:831; Robi et al. 2003, *Theriogenology* 59:107; Malassagne et al. 2003, *Xenotransplantation* 10(3):267).

D. Improvements Offered by Certain Embodiments of the Invention

Recombinant technology provides a fast and relatively inexpensive way to produce large quantities of chimeric proteins, however the technology is not without its limitations. For example large multi-domain proteins can be difficult to express recombinantly. Recombinant expression of chimeric proteins often results in a heterogenous product requiring extensive purification. Some chimeric proteins may be toxic to cells making their expression, difficult, if not impossible. Moreover, recombinantly expressed proteins can only be comprised of the naturally occurring 20 amino acids. Thus, only L-configuration amino acids are possible using recombinant methods. Expressing chimeric proteins comprised of non-naturally occurring amino acids, provides a way to generate analogs useful in studying protein function and inhibiting undesirable metabolic pathways. Alternatively, analogs comprising non-naturally occurring amino acids may be used in some cases to enhance the activity of desirable metabolic pathways. Lastly, chimeric proteins comprising both amino acids and another biologically active molecules, e.g., nucleic acids, small molecules, are impossible to express using recombinant technology alone.

Many of the limitations described above may be overcome using chemical synthesis alone or a combination of recombinant techniques and chemical synthesis. A number of traditional techniques for chemically synthesizing proteins, such as solid phase synthesis are known in the art, see, e.g., Merrifield, 1973, *Chemical Polypeptides*, (Katsoyannis and Panayotis eds.) pp. 335-61; Merrifield 1963, *J. Am. Chem. Soc.* 85:2149; Davis et al. 1985, *Biochem. Intl.* 10:394; Finn et al. 1976, *The Proteins* (3d ed.) 2:105; Erikson et al. 1976, *The Proteins* (3d ed.) 2:257; U.S. Pat. No. 3,941,763.

Recent improvements in the chemical synthesis of proteins include the advent of native chemical ligation. As initially described, native ligation provides for the rapid synthesis of large polypeptides with a natural peptide backbone via the native chemical ligation of two or more unprotected peptide segments. In native ligation none of the reactive functionalities on the peptide segments need to be temporarily masked by a protecting group. Native ligation also allows for the solid phase sequential chemical ligation of peptide segments in an N-terminus to C-terminus direction, with the first solid phase-bound unprotected peptide segment bearing a C-terminal alpha-thioester that reacts with another unprotected peptide segment containing an N-terminal cysteine. Native chemical ligation also permits the solid-phase ligation in the C— to N-terminus direction, with temporary protection of N-terminal cysteine residues on an incoming (second) peptide segment (see, e.g., U.S. Pat. No. 6,326,468; WO 02/18417).

Native ligation may also be combined with recombinant technology using intein linked to a chitin binding domain (Muir et al., 1998, *Proc. Natl. Acad. Sci. USA*, 95:6705).

The invention provides for chimeric proteins (monomer-dimer hybrids) comprising a first and a second polypeptide chain, wherein said first chain comprises a biologically active molecule and at least a portion of an immunoglobulin constant region, and said second chain comprises at least a portion of an immunoglobulin constant region without any biologically active molecule or variable region of an immunoglobulin. FIG. 1 contrasts traditional fusion protein dimers with one example of the monomer-dimer hybrid of the invention. In this example, the biologically active molecule is EPO and the portion of an immunoglobulin is IgG Fc region.

Like other chimeric proteins comprised of at least a portion of an immunoglobulin constant region, the invention provides for chimeric proteins which afford enhanced stability and increased bioavailability of the chimeric protein compared to the biologically active molecule alone. Additionally, however, because only one of the two chains comprises the biologically active molecule, the chimeric protein has a lower molecular weight than a chimeric protein wherein all chains comprise a biologically active molecule and while not wishing to be bound by any theory, this may result in the chimeric protein being more readily transcytosed across the epithelium barrier, e.g., by binding to the FcRn receptor thereby increasing the half-life of the chimeric protein. In one embodiment, the invention thus provides for an improved non-invasive method (e.g. via any mucosal surface, such as, orally, buccally, sublingually, nasally, rectally, vaginally, or via pulmonary or ocular route) of administering a therapeutic chimeric protein of the invention. The invention thus provides methods of attaining therapeutic levels of the chimeric proteins of the invention using less frequent and lower doses compared to previously described chimeric proteins (e.g. chimeric proteins comprised of at least a portion of an immunoglobulin constant region and a biologically active molecule, wherein all chains of the chimeric protein comprise a biologically active molecule).

In another embodiment, the invention provides an invasive method, e.g., subcutaneously, intravenously, of administering a therapeutic chimeric protein of the invention. Invasive administration of the therapeutic chimeric protein of the invention provides for an increased half life of the therapeutic chimeric protein which results in using less frequent and lower doses compared to previously described chimeric proteins (e.g. chimeric proteins comprised of at least a portion of an immunoglobulin constant region and a biologically active molecule, wherein all chains of the chimeric protein comprise a biologically active molecule).

Yet another advantage of a chimeric protein wherein only one of the chains comprises a biologically active molecule is the enhanced accessibility of the biologically active molecule for its target cell or molecule resulting from decreased steric hindrance, decreased hydrophobic interactions, decreased ionic interactions, or decreased molecular weight compared to a chimeric protein wherein all chains are comprised of a biologically active molecule.

E. Chimeric Proteins

The invention relates to chimeric proteins comprising one biologically active molecule, at least a portion of an immunoglobulin constant region, and optionally at least one linker. The portion of an immunoglobulin will have both an N, or an amino terminus, and a C, or carboxy terminus. The chimeric protein may have the biologically active molecule linked to the N terminus of the portion of an immunoglobulin. Alternatively, the biologically active molecule may be linked to the C terminus of the portion of an immunoglobulin. In one embodiment, the linkage is a covalent bond. In another embodiment, the linkage is a non-covalent bond.

The chimeric protein can optionally comprise at least one linker; thus, the biologically active molecule does not have to be directly linked to the portion of an immunoglobulin constant region. The linker can intervene in between the biologically active molecule and the portion of an immunoglobulin constant region. The linker can be linked to the N terminus of the portion of an immunoglobulin constant region, or the C terminus of the portion of an immunoglobulin constant region. If the biologically active molecule is comprised of at least one amino acid the biologically active molecule will have an N terminus and a C terminus and the linker can be linked to the N terminus of the biologically active molecule, or the C terminus the biologically active molecule.

The invention relates to a chimeric protein of the formula $X-L_a-F:F$ or $F:F-L_a-X$, wherein X is a biologically active molecule, L is an optional linker, F is at least a portion of an immunoglobulin constant region and, a is any integer or zero. The invention also relates to a chimeric protein of the formula $T_a-X-L_a-F:F$ or $T_a-F:F-L_a-X$, wherein X is a biologically active molecule, L is an optional linker, F is at least a portion of an immunoglobulin constant region, a is any integer or zero, T is a second linker or alternatively a tag that can be used to facilitate purification of the chimeric protein, e.g., a FLAG tag, a histidine tag, a GST tag, a maltose binding protein tag and (:) represents a chemical association, e.g. at least one non-peptide bond. In certain embodiments, the chemical association, i.e., (:) is a covalent bond. In other embodiments, the chemical association, i.e., (:) is a non-covalent interaction, e.g., an ionic interaction, a hydrophobic interaction, a hydrophilic interaction, a Van der Waals interaction, a hydrogen bond. It will be understood by the skilled artisan that when a equals zero X will be directly linked to F. Thus, for example, a may be 0, 1, 2, 3, 4, 5, or more than 5.

1. Chimeric Protein Variants

Derivatives of the chimeric proteins of the invention, antibodies against the chimeric proteins of the invention and antibodies against binding partners of the chimeric proteins of the invention are all contemplated, and can be made by altering their amino acids sequences by substitutions, additions, and/or deletions/truncations or by introducing chemical modification that result in functionally equivalent molecules. It will be understood by one of ordinary skill in the art that certain amino acids in a sequence of any protein may be substituted for other amino acids without adversely affecting the activity of the protein.

Various changes may be made in the amino acid sequences of the chimeric proteins of the invention or DNA sequences encoding therefore without appreciable loss of their biological activity, function, or utility. Derivatives, analogs, or mutants resulting from such changes and the use of such derivatives is within the scope of the present invention. In a specific embodiment, the derivative is functionally active, i.e., capable of exhibiting one or more activities associated with the chimeric proteins of the invention, e.g., FcRn binding, viral inhibition, hemostasis, production of red blood cells. Many assays capable of testing the activity of a chimeric protein comprising a biologically active molecule are known in the art. Where the biologically active molecule is an HIV inhibitor, activity can be tested by measuring reverse transcriptase activity using known methods (see e.g. Barre-Sinoussi et al. 1983, *Science* 220:868; Gallo et al. 1984, *Science* 224:500). Alternatively, activity can be measured by measuring fusogenic activity (see e.g. Nussbaum et al. 1994, *J. Virol.* 68(9):5411). Where the biological activity is hemostasis, a StaCLot FVIIa-rTF assay can be performed to assess activity of Factor VIIa derivatives (Johannessen et al. 2000, *Blood Coagulation and Fibrinolysis* 11:S159).

Substitutes for an amino acid within the sequence may be selected from other members of the class to which the amino acid belongs (see Table 1). Furthermore, various amino acids are commonly substituted with neutral amino acids, e.g., alanine, leucine, isoleucine, valine, proline, phenylalanine, tryptophan, and methionine (see e.g. MacLennan et al. 1998, *Acta Physiol. Scand. Suppl.* 643:55-67; Sasaki et al. 1998, *Adv. Biophys.* 35:1-24).

TABLE 1

| Original Residues | Exemplary Substitutions | Typical Substitutions |
|---|---|---|
| Ala (A) | Val, Leu, Ile | Val |
| Arg (R) | Lys, Gln, Asn | Lys |
| Asn (N) | Gln | Gln |
| Asp (D) | Glu | Glu |
| Cys (C) | Ser, Ala | Ser |
| Gln (Q) | Asn | Asn |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, 1,4-Diamino-butyric Acid, Gln, Asn | Arg |
| Met (M) | Leu, Phe, Ile | Leu |
| Phe (F) | Leu, Val, Ile, Ala, Tyr | Leu |
| Pro (P) | Ala | Gly |
| Ser (S) | Thr, Ala, Cys | Thr |
| Thr (T) | Ser | Ser |
| Trp (W) | Tyr, Phe | Tyr |
| Tyr (Y) | Trp, Phe, Thr, Ser | Phe |
| Val (V) | Ile, Met, Leu, Phe, Ala, Norleucine | Leu |

2. Biologically Active Molecules

The invention contemplates the use of any biologically active molecule as the therapeutic molecule of the invention. The biologically active molecule can be a polypeptide. The biologically active molecule can be a single amino acid. The biologically active molecule can include a modified polypeptide.

The biologically active molecule can include a lipid molecule (e.g. a steroid or cholesterol, a fatty acid, a triacylglycerol, glycerophospholipid, or sphingolipid). The biologically active molecule can include a sugar molecule (e.g. glucose, sucrose, mannose). The biologically active molecule can include a nucleic acid molecule (e.g. DNA, RNA). The biologically active molecule can include a small organic molecule or a small inorganic molecule.

a. Cytokines and Growth Factors

In one embodiment, the biologically active molecule is a growth factor, hormone or cytokine or analog or fragment thereof. The biologically active molecule can be any agent capable of inducing cell growth and proliferation. In a specific embodiment, the biologically active molecule is any agent which can induce erythrocytes to proliferate. Thus, one example of a biologically active molecule contemplated by the invention is EPO. The biologically active molecule can also include, but is not limited to, RANTES, MIP1α, MIP1β, IL-2, IL-3, GM-CSF, growth hormone, tumor necrosis factor (e.g. TNFα or β).

The biologically active molecule can include interferon α, whether synthetically or recombinantly produced, including but not limited to, any one of the about twenty-five structurally related subtypes, as for example interferon-α2a, now commercially available for clinical use (ROFERON®, Roche) and interferon-α2b also approved for clinical use (INTRON®, Schering) as well as genetically engineered versions of various subtypes, including, but not limited to, commercially available consensus interferon α (INFERGEN®, Intermune, developed by Amgen) and consensus human leukocyte interferon see, e.g., U.S. Pat. Nos. 4,695,623; 4,897,471, interferon β, epidermal growth factor, gonadotropin releasing hormone (GnRH), leuprolide, follicle stimulating hormone, progesterone, estrogen, or testosterone.

A list of cytokines and growth factors which may be used in the chimeric protein of the invention has been previously described (see e.g. U.S. Pat. Nos. 6,086,875, 6,485,726, 6,030,613; WO 03/077834; US 2003-0235536A1).

b. Antiviral Agents

In one embodiment, the biologically active molecule is an antiviral agent, including fragments and analogs thereof. An antiviral agent can include any molecule that inhibits or prevents viral replication, or inhibits or prevents viral entry into a cell, or inhibits or prevents viral egress from a cell. In one embodiment, the antiviral agent is a fusion inhibitor. In one embodiment, the antiviral agent is a cytokine which inhibits viral replication. In another embodiment, the antiviral agent is interferon α.

The viral fusion inhibitor for use in the chimeric protein can be any molecule which decreases or prevents viral penetration of a cellular membrane of a target cell. The viral fusion inhibitor can be any molecule that decreases or prevents the formation of syncytia between at least two susceptible cells. The viral fusion inhibitor can be any molecule that decreases or prevents the joining of a lipid bilayer membrane of a eukaryotic cell and a lipid bilayer of an enveloped virus. Examples of enveloped virus include, but are not limited to HIV-1, HIV-2, SIV, influenza, parainfluenza, Epstein-Barr virus, CMV, herpes simplex 1, herpes simplex 2 and respiratory syncytia virus.

The viral fusion inhibitor can be any molecule that decreases or prevents viral fusion including, but not limited to, a polypeptide, a small organic molecule or a small inorganic molecule. In one embodiment, the fusion inhibitor is a polypeptide. In one embodiment, the viral fusion inhibitor is a polypeptide of 3-36 amino acids. In another embodiment, the viral fusion inhibitor is a polypeptide of 3-50 amino acids, 10-65 amino acids, 10-75 amino acids. The polypeptide can be comprised of a naturally occurring amino acid sequence (e.g. a fragment of gp41) including analogs and mutants thereof or the polypeptide can be comprised of an amino acid sequence not found in nature, so long as the polypeptide exhibits viral fusion inhibitory activity.

In one embodiment, the viral fusion inhibitor is a polypeptide, identified as being a viral fusion inhibitor using at least one computer algorithm, e.g., ALLMOTI5, 107×178×4 and PLZIP (see e.g. U.S. Pat. Nos. 6,013,263; 6,015,881; 6,017,536; 6,020,459; 6,060,065; 6,068,973; 6,093,799; and 6,228,983).

In one embodiment, the viral fusion inhibitor is an HIV fusion inhibitor. In one embodiment, HIV is HIV-1. In another embodiment, HIV is HIV-2. In one embodiment, the HIV fusion inhibitor is a polypeptide comprised of a fragment of the gp41 envelope protein of HIV-1. The HIV fusion inhibitor can comprise, e.g., T20 or an analog thereof, T21 or an analog thereof, T1249 or an analog thereof, $N_{CCG}gp41$ (Louis et al. 2001, *J. Biol. Chem.* 276:(31)29485) or an analog thereof, or 5 helix (Root et al. 2001, *Science* 291:884) or an analog thereof.

Assays known in the art can be used to test for viral fusion inhibiting activity of a polypeptide, a small organic molecule, or a small inorganic molecule. These assays include a reverse transcriptase assay, a p24 assay, or syncytia formation assay (see e.g. U.S. Pat. No. 5,464,933).

A list of antiviral agents which may be used in the chimeric protein of the invention has been previously described (see e.g. U.S. Pat. Nos. 6,086,875, 6,485,726, 6,030,613; WO 03/077834; US 2003-0235536A1).

c. Hemostatic Agents

In one embodiment, the biologically active molecule is a clotting factor or other agent that promotes hemostasis, including fragments and analogs thereof. The clotting factor can include any molecule that has clotting activity or activates a molecule with clotting activity. The clotting factor can be comprised of a polypeptide. The clotting factor can be, as an example, but not limited to Factor VII, Factor IX, Factor XI, Factor XII, fibrinogen, prothrombin, Factor V, Factor VII, Factor X, Factor XIII or von Willebrand Factor. In one embodiment, the clotting factor is Factor VII or Factor VIIa. The clotting factor can be a factor that participates in the extrinsic pathway. The clotting factor can be a factor that participates in the intrinsic pathway. Alternatively, the clotting factor can be a factor that participates in both the extrinsic and intrinsic pathway.

The clotting factor can be a human clotting factor or a non-human clotting factor, e.g., derived from a non-human primate, a pig or any mammal. The clotting factor can be chimeric clotting factor, e.g., the clotting factor can comprise a portion of a human clotting factor and a portion of a porcine clotting factor or a portion of a first non-human clotting factor and a portion of a second non-human clotting factor.

The clotting factor can be an activated clotting factor. Alternatively, the clotting factor can be an inactive form of a clotting factor, e.g., a zymogen. The inactive clotting factor can undergo activation subsequent to being linked to at least a portion of an immunoglobulin constant region. The inactive clotting factor can be activated subsequent to administration to a subject. Alternatively, the inactive clotting factor can be activated prior to administration.

d. Other Proteinaceous Biologically Active Molecules

In one embodiment, the biologically active molecule is a receptor or a fragment or analog thereof. The receptor can be expressed on a cell surface, or alternatively the receptor can be expressed on the interior of the cell. The receptor can be a viral receptor, e.g., CD4, CCR5, CXCR4, CD21, CD46. The biologically active molecule can be a bacterial receptor. The biologically active molecule can be an extra-cellular matrix protein or fragment or analog thereof, important in bacterial colonization and infection (see e.g. U.S. Pat. Nos. 5,648,240; 5,189,015; 5,175,096) or a bacterial surface protein important in adhesion and infection (see e.g. U.S. Pat. No. 5,648,240). The biologically active molecule can be a growth factor, hormone or cytokine receptor, or a fragment or analog thereof, e.g., TNFα receptor, the erythropoietin receptor, CD25, CD122, or CD132.

A list of other proteinaceous molecules which may be used in the chimeric protein of the invention has been previously described (see e.g. U.S. Pat. Nos. 6,086,875; 6,485,726; 6,030,613; WO 03/077834; US 2003-0235536A1).

e. Nucleic Acids

In one embodiment, the biologically active molecule is a nucleic acid, e.g., DNA, RNA. In one specific embodiment, the biologically active molecule is a nucleic acid that can be used in RNA interference (RNAi). The nucleic acid molecule can be as an example, but not as a limitation, an anti-sense molecule or a ribozyme.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarily, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides or at least 50 nucleotides.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as polypeptides (e.g. for targeting host cell receptors in vivo), or agents facilitating transport across the cell membrane (see e.g. Letsinger et al. 1989, *Proc. Natl. Acad. Sci. USA* 86:6553; Lemaitre et al. 1987, *Proc. Natl. Acad. Sci. USA* 84:648; WO 88/09810,) or the blood-brain barrier (see e.g. WO 89/10134), hybridization-triggered cleavage agents (see e.g. Krol et al. 1988, *BioTechniques* 6:958) or intercalating agents (see e.g. Zon 1988, *Pharm. Res.* 5:539). To this end, the oligonucleotide may be conjugated to another molecule, e.g., a polypeptide, hybridization triggered cross-linking agent, transport agent, or hybridization-triggered cleavage agent.

Ribozyme molecules designed to catalytically cleave target gene mRNA transcripts can also be used to prevent translation of target gene mRNA and, therefore, expression of target gene product. (See e.g. WO 90/11364; Sarver et al. 1990, *Science* 247, 1222-1225).

Ribozymes are enzymatic RNA molecules capable of catalyzing the specific cleavage of RNA. (see Rossi 1994, *Current Biology* 4:469). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246.

In one embodiment, ribozymes that cleave mRNA at site specific recognition sequences can be used to destroy target gene mRNAs. In another embodiment, the use of hammerhead ribozymes is contemplated. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers 1995, *Molecular Biology and Biotechnology: A Comprehensive Desk Reference*, VCH Publishers, New York, and in Haseloff and Gerlach 1988, *Nature,* 334:585.

f. Small Molecules

The invention also contemplates the use of any therapeutic small molecule or drug as the biologically active molecule in the chimeric protein of the invention. A list of small molecules and drugs which may be used in the chimeric protein of the invention has been previously described (see e.g. U.S. Pat. Nos. 6,086,875; 6,485,726; 6,030,613; WO 03/077834; US 2003-0235536A1).

2. Immunoglobulins

The chimeric proteins of the invention comprise at least a portion of an immunoglobulin constant region. Immunoglobulins are comprised of four protein chains that associate covalently—two heavy chains and two light chains. Each chain is further comprised of one variable region and one constant region. Depending upon the immunoglobulin isotype, the heavy chain constant region is comprised of 3 or 4 constant region domains (e.g. CH1, CH2, CH3, CH4). Some isotypes are further comprised of a hinge region.

The portion of an immunoglobulin constant region can be obtained from any mammal. The portion of an immunoglobulin constant region can include a portion of a human immunoglobulin constant region, a non-human primate immunoglobulin constant region, a bovine immunoglobulin constant region, a porcine immunoglobulin constant region, a murine immunoglobulin constant region, an ovine immunoglobulin constant region or a rat immunoglobulin constant region.

The portion of an immunoglobulin constant region can be produced recombinantly or synthetically. The immunoglobulin can be isolated from a cDNA library. The portion of an immunoglobulin constant region can be isolated from a phage library (See e.g. McCafferty et al. 1990, *Nature* 348:552, Kang et al. 1991, *Proc. Natl. Acad. Sci. USA* 88:4363; EP 0 589 877 B1). The portion of an immunoglobulin constant region can be obtained by gene shuffling of known sequences (Mark et al. 1992, *Bio/Technol.* 10:779). The portion of an immunoglobulin constant region can be isolated by in vivo recombination (Waterhouse et al. 1993, *Nucl. Acid Res.* 21.2265). The immunoglobulin can be a humanized immunoglobulin (U.S. Pat. No. 5,585,089, Jones et al. 1986, *Nature* 332:323).

The portion of an immunoglobulin constant region can include a portion of an IgG, an IgA, an IgM, an IgD, or an IgE. In one embodiment, the immunoglobulin is an IgG. In another embodiment, the immunoglobulin is IgG1. In another embodiment, the immunoglobulin is IgG2.

The portion of an immunoglobulin constant region can include the entire heavy chain constant region, or a fragment or analog thereof. In one embodiment, a heavy chain constant region can comprise a CH1 domain, a CH2 domain, a CH3 domain, and/or a hinge region. In another embodiment, a heavy chain constant region can comprise a CH1 domain, a CH2 domain, a CH3 domain, and/or a CH4 domain.

The portion of an immunoglobulin constant region can include an Fc fragment. An Fc fragment can be comprised of the CH2 and CH3 domains of an immunoglobulin and the hinge region of the immunoglobulin. The Fc fragment can be the Fc fragment of an IgG1, an IgG2, an IgG3 or an IgG4. In one specific embodiment, the portion of an immunoglobulin constant region is an Fc fragment of an IgG1. In another embodiment, the portion of an immunoglobulin constant region is an Fc fragment of an IgG2.

In another embodiment, the portion of an immunoglobulin constant region is an Fc neonatal receptor (FcRn) binding partner. An FcRn binding partner is any molecule that can be specifically bound by the FcRn receptor with consequent active transport by the FcRn receptor of the FcRn binding partner. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant $K_A$ is higher than $10^6$ $M^{-1}$, or more preferably higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., may be optimized by a skilled artisan using routine techniques.

The FcRn-receptor has been isolated from several mammalian species including humans. The sequences of the human FcRn, monkey FcRn rat FcRn, and mouse FcRn are known (Story et al. 1994, *J. Exp. Med.* 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US 2003-0235536A1) including lung and intestinal epithelium (Israel et al. 1997, *Immunology* 92:69) renal proximal tubular epithelium (Kobayashi et al. 2002, *Am. J. Physiol. Renal Physiol.* 282:F358). as well as nasal epithelium, vaginal surfaces, and biliary tree surfaces.

FcRn binding partners of the present invention encompass any molecule that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, *Nature* 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, *Sequences of Proteins of Immunological Interest*, U.S. Department of Public Health, Bethesda, Md.

The Fc region of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A; L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A; R416A, Q418A, Q419A, N421A, V422A, S424A, E430A, N434A, T437A, Q438A, K439A, S440A, S444A, and K447A, where for example P238A represents wildtype proline substituted by alanine at position number 238. In addition to alanine other amino acids may be substituted for the wildtype amino acids at the positions specified above. Mutations may be introduced singly into Fc giving rise to more than one hundred FcRn binding partners distinct from native Fc. Additionally, combinations of two, three, or more of these individual mutations may be introduced together, giving rise to hundreds more FcRn binding partners. Moreover, one of the FcRn binding partners may be mutated and the other not, or they both may different mutations.

Certain of the above mutations may confer new functionality upon the FcRn binding partner. For example, one embodiment incorporates N297A, removing a highly conserved N-glycosylation site. The effect of this mutation is to reduce immunogenicity, thereby enhancing circulating half life of the FcRn binding partner, and to render the FcRn binding partner incapable of binding to FcγRI, FcγRIIA, FcγRIIB, and FcγRIIIA, without compromising affinity for FcRn (Routledge et al. 1995, *Transplantation* 60:847; Friend et al. 1999, *Transplantation* 68:1632; Shields et al. 1995, *J. Biol. Chem.* 276:6591). As a further example of new functionality arising from mutations described above affinity for FcRn may be increased beyond that of wild type in some instances. This increased affinity may reflect an increased "on" rate, a decreased "off" rate or both an increased "on" rate and a decreased "off" rate. Mutations believed to impart an increased affinity for FcRn include T256A, T307A, E380A, and N434A (Shields et al. 2001, *J. Biol. Chem.* 276:6591). Any of the described mutations, including N597A, can be used to modify Fc, regardless of the biologically active molecule.

Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" (SEQ ID NO:42) to the corresponding sequence from IgG2 "PVA" (with one amino acid deletion). It has been shown that FcγRI, FcγRII, and FcγRII, which mediate various effector functions will not bind to IgG1 when such mutations have been introduced. Ward and Ghetie 1995, *Therapeutic Immunology* 2:77 and Armour et al. 1999, *Eur. J. Immunol.* 29:2613.

In one embodiment, the FcRn binding partner is a polypeptide including the sequence PKNSSMISNTP (SEQ ID NO:1) and optionally further including a sequence selected from HQSLGTQ (SEQ ID NO:2), HQNLSDGK (SEQ ID NO:3), HQNISDGK (SEQ ID NO:4), or VISSHLGQ (SEQ ID NO:5) (U.S. Pat. No. 5,739,277).

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the chimeric protein can be administered invasively, e.g., subcutaneously, intravenously.

The skilled artisan will understand that portions of an immunoglobulin constant region for use in the chimeric protein of the invention can include mutants or analogs thereof, or can include chemically modified immunoglobulin constant regions (e.g. pegylated), or fragments thereof (see e.g. Aslam and Dent 1998, *Bioconjugation: Protein Coupling Techniques For the Biomedical Sciences Macmilan Reference*, London). In one instance, a mutant can provide for enhanced binding of an FcRn binding partner for the FcRn. Also contemplated for use in the chimeric protein of the invention are peptide mimetics of at least a portion of an immunoglobulin constant region, e.g., a peptide mimetic of an Fc fragment or a peptide mimetic of an FcRn binding partner. In one embodiment, the peptide mimetic is identified using phage display or via chemical library screening (see e.g. McCafferty et al. 1990, *Nature* 348:552, Kang et al. 1991, *Proc. Natl. Acad. Sci. USA* 88:4363; EP 0 589 877 B1).

3. Optional Linkers

The chimeric protein of the invention can optionally comprise at least one linker molecule. The linker can be comprised of any organic molecule. In one embodiment, the linker is polyethylene glycol (PEG). In another embodiment, the linker is comprised of amino acids. The linker can comprise 1-5 amino acids, 1-10 amino acids, 1-20 amino acids, 10-50 amino acids, 50-100 amino acids, 100-200 amino acids. In one embodiment, the linker is the eight amino acid linker EFAGAAAV (SEQ ID NO:6). Any of the linkers including EFAGAAV (SEQ ID NO:7), can be used regardless of the biologically active molecule.

The linker can comprise the sequence $G_n$. The linker can comprise the sequence $(GA)_n$ (SEQ ID NO:8). The linker can comprise the sequence $(GGS)_n$ (SEQ ID NO:9). The linker can comprise the sequence $(GGS)_n(GGGGS)_n$ (SEQ ID NO:10). In these instances, n may be an integer from 1-10, i.e., 1, 2, 3, 4, 5, 6, 7, 8, 9, 10. Examples of linkers include, but are not limited to, GGG, SGGSGGS (SEQ ID NO:11), GGSGGSGGSGGSGGG (SEQ ID NO:12), GGSGGSGGGSGGGGS (SEQ ID NO:13), GGSGGSGGSGGSGGSGGS (SEQ ID NO:14). The linker does not eliminate or diminish the biological activity of the chimeric protein. Optionally, the linker enhances the biological activity of the chimeric protein, e.g., by further diminishing the effects of steric hindrance and making the biologically active molecule more accessible to its target binding site.

In one specific embodiment, the linker for interferon α is 15-25 amino acids long. In another specific embodiment, the linker for interferon α is 15-20 amino acids long. In another specific embodiment, the linker for interferon α is 10-25 amino acids long. In another specific embodiment, the linker for interferon α is 15 amino acids long. In one embodiment, the linker for interferon α is $(GGGGS)_n$ (SEQ ID NO:15) where G represents glycine, S represents serine and n is an integer from 1-10. In a specific embodiment, n is 3.

The linker may also incorporate a moiety capable of being cleaved either chemically (e.g. hydrolysis of an ester bond), enzymatically (i.e. incorporation of a protease cleavage sequence) or photolytically (e.g., a chromophore such as 3-amino-3-(2-nitrophenyl) proprionic acid (ANP)) in order to release the biologically active molecule from the Fc protein.

In certain embodiments, the linker is a branching molecule. A branching molecule can be used to link a plurality of biologically active molecules to a portion of an immunoglobulin constant region, e.g. an Fc fragment. Alternatively, a branching molecule could be used to link more than one portion of an immunoglobulin constant region to a single biologically active molecule, i.e. a dimerically linked monomer dimer hybrid. Branching molecules may be comprised of at least two different functional groups. The first functional group may bind to the portion of the immunoglobulin constant region. The second functional group may bind to the biological molecule of interest. The number of each type of functional group will vary depending on the number of biologically active molecules or portions of an immunoglobulin constant region desired. Thus, in one example, a branching molecule which may be used for a dimerically linked monomer dimer hybrid will have two copies of a first functional group which will bind to the 2 Fc fragments for example, and a single copy of the second functional group which will bind to the biologically active molecule.

The linker attached to the N-terminus of CysFc may also contain both a thioester and a protected hydrazine as shown below.

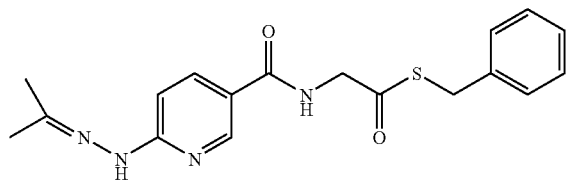

Attachment of the linker to CysFc via the thioester (native ligation), followed by a 4 hour treatment of the protein-linker conjugate at pH 4.6, can reveal the free hydrazine. This effectively generates Fc labeled with a hydrazine specifically at the N-terminus which can then react specifically with aldehydes to form hydrazones. This technique may be advantageous when the synthesis of a thioester on an bioactive molecule is not easily accessible (e.g., a phosphorothioate oligonucleotide thioester).

The skilled artisan will appreciate that a vast number of linkers which are branching molecules are possible. Two examples of linkers which are branching molecules are shown below. The first molecule is 4-aminoglycine-3-methylaminoglycine-benzoic acid. The amines can be converted into thioesters for attachment to the two N-terminal Cys of Fc. The carboxylic acid can be used to attach any biological molecule of interest, including polypeptides and small molecules.

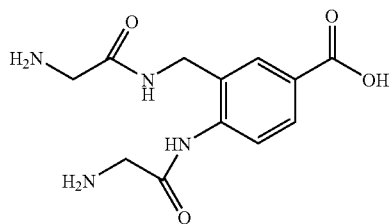

The dipeptide Gly-Glu is shown below. Here the functionalities include two carboxylic acids and one amine. The carboxylic acids may be converted to thioesters and the amine is used to attach a biological molecule of interest.

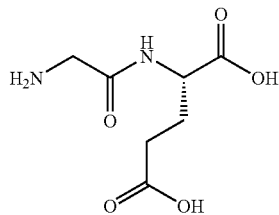

Two more examples of branching molecules which can used as linkers in synthesizing the chimeric proteins of the invention are shown below. Linker 1 is N,N-bis(3-aminopropyl)glycine. Linker 2 is a β-alanine-lysine dipeptide.

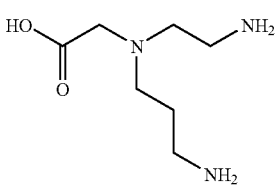

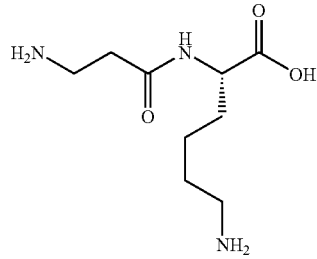

Each molecule has three functionalities for further derivatization where two of the functionalities are the same. In the case of these linkers, the two amino groups ($NH_2$) in each molecule can be derivatized to thioesters for eventual reaction with the two N-terminal cysteines on Cys-Fc. The carboxylic acid group (COOH) group can be functionalized with any sort of molecule. As an example a small molecule derivatized with linker 1 at its carboxylic acid and derivatized with two thioesters at its amino groups could be synthesized.

4. Chimeric Protein Dimerization Using Specific Binding Partners

In one embodiment, the chimeric protein of the invention comprises a first polypeptide chain comprising at least a first domain, said first domain having at least one specific binding partner, and a second polypeptide chain comprising at least a second domain, wherein said second domain, is a specific binding partner of said first domain. The chimeric protein thus comprises a polypeptide capable of dimerizing with another polypeptide due to the interaction of the first domain and the second domain. Methods of dimerizing antibodies using heterologous domains are known in the art (U.S. Pat. Nos. 5,807,706 and 5,910,573; Kostelny et al. 1992, *J. Immunol.* 148(5):1547).

Dimerization can occur by formation of a covalent bond, or alternatively a non-covalent bond, e.g., hydrophobic interaction, Van der Waal's forces, interdigitation of amphiphilic peptides such as, but not limited to, alpha helices, charge-charge interactions of amino acids bearing opposite charges, such as, but not limited to, lysine and aspartic acid, arginine and glutamic acid. In one embodiment, the domain is a helix bundle comprising a helix, a turn and another helix. In another embodiment, the domain is a leucine zipper comprising a peptide having several repeating amino acids in which every seventh amino acid is a leucine residue. In one embodiment, the specific binding partners are fos/jun. (see Branden et al. 1991, *Introduction To Protein Structure*, Garland Publishing, New York).

In another embodiment, binding is mediated by a chemical linkage (see e.g. Brennan et al. 1985, *Science* 229:81). In this embodiment, intact immunoglobulins, or chimeric proteins comprised of at least a portion of an immunoglobulin constant region are cleaved to generate heavy chain fragments. These fragments are reduced in the presence of the dithiol complexing agent sodium arsenite to stabilize vicinal dithiols and prevent intermolecular disulfide formation. The fragments generated are then converted to thionitrobenzoate (TNB) derivatives. One of the TNB derivatives is then reconverted to the heavy chain fragment thiol by reduction with mercaptoethylamine and is then mixed with an equimolar amount of the other TNB derivative to form a chimeric dimer.

E. Nucleic Acids

The invention relates to a first nucleic acid construct and a second nucleic acid construct each comprising a nucleic acid sequence encoding at least a portion of the chimeric protein of the invention. In one embodiment, the first nucleic acid construct comprises a nucleic acid sequence encoding a portion of an immunoglobulin constant region operatively linked to a second DNA sequence encoding a biologically active molecule, and said second DNA construct comprises a DNA sequence encoding an immunoglobulin constant region without the second DNA sequence encoding a biologically active molecule.

The biologically active molecule can include, for example, but not as a limitation, a viral fusion inhibitor, a clotting factor, a growth factor or hormone, or a receptor, or analog, or fragment of any of the preceding. The nucleic acid sequences can also include additional sequences or elements known in the art (e.g., promoters, enhancers, poly A sequences, affinity tags). In one embodiment, the nucleic acid sequence of the second construct can optionally include a nucleic acid sequence encoding a linker placed between the nucleic acid sequence encoding the biologically active molecule and the portion of the immunoglobulin constant region. The nucleic acid sequence of the second DNA construct can optionally include a linker sequence placed before or after the nucleic acid sequence encoding the biologically active molecule and/ or the portion of the immunoglobulin constant region.

In one embodiment, the nucleic acid construct is comprised of DNA. In another embodiment, the nucleic acid construct is comprised of RNA. The nucleic acid construct can be a vector, e.g., a viral vector or a plasmid. Examples of viral vectors include, but are not limited to adeno virus vector, an adeno associated virus vector or a murine leukemia virus vector. Examples of plasmids include but are not limited to pUC, pGEM and pGEX.

Due to the known degeneracy of the genetic code, wherein more than one codon can encode the same amino acid, a DNA sequence can vary from the native sequence and still encode a polypeptide corresponding to the naturally occurring amino acid sequence. Such variant DNA sequences can result from silent mutations (e.g. occurring during PCR amplification), or can be the product of deliberate mutagenesis of a native sequence. Of course, polypeptides encoded by such DNA sequences are encompassed by the invention.

In another embodiment, the nucleic acid molecules comprising a sequence encoding the chimeric protein of the invention can also comprise nucleotide sequences that are at least 80% identical to a native sequence. Also contemplated are embodiments in which a nucleic acid molecules comprising a sequence encoding the chimeric protein of the invention comprises a sequence that is at least 90% identical, at least 95% identical, at least 98% identical, at least 99% identical, or at least 99.9% identical to a native sequence. A native sequence can include any DNA sequence not altered by the human hand. The percent identity may be determined by visual inspection and mathematical calculation. Alternatively, the percent identity of two nucleic acid sequences can be determined by comparing sequence information using the GAP computer program, version 6.0 described by Devereux et al. 1984, *Nucl. Acids Res.* 12:387, and available from the University of Wisconsin Genetics Computer Group (UWGCG). The preferred default parameters for the GAP program include: (1) a unary comparison matrix (containing a value of 1 for identities and 0 for nonidentities) for nucleotides, and the weighted comparison matrix of Gribskov and Burgess 1986, *Nucl. Acids Res.* 14:6745, as described by Schwartz and Dayhoff, eds. 1979, *Atlas of Protein Sequence and Structure*, National Biomedical Research Foundation, pp. 353-358; (2) a penalty of 3.0 for each gap and an additional 0.10 penalty for each symbol in each gap; and (3) no penalty for end gaps. Other programs used by one skilled in the art of sequence comparison may also be used.

F. Methods of Using Chimeric Proteins

The chimeric proteins of the invention have many uses as will be recognized by one skilled in the art, including, but not limited to methods of treating a subject with a disease or condition. The disease or condition can include, but is not limited to, a viral infection, a hemostatic disorder, anemia, cancer, leukemia, an inflammatory condition or an autoimmune disease (e.g. arthritis, psoriasis, lupus erythematosus, multiple sclerosis), or a bacterial infection (see e.g. U.S. Pat. Nos. 6,086,875, 6,030,613, 6,485,726; WO 03/077834; US 2003-0235536A1).

1. Methods of Treating a Subject with a Red Blood Cell Deficiency

The invention relates to a method of treating a subject having a deficiency of red blood cells, e.g., anemia, comprising administering a therapeutically effective amount of at least one chimeric protein, wherein the chimeric protein comprises a first and a second polypeptide chain, wherein the first chain comprises at least a portion of an immunoglobulin constant region and at least one agent capable of inducing proliferation of red blood cells, e.g., EPO, and the second polypeptide chain comprises at least a portion of an immunoglobulin without the agent capable of inducing red blood cell proliferation of the first chain.

2. Methods of Treating a Subject with a Viral Infection

The invention relates to a method of treating a subject having a viral infection or exposed to a virus comprising administering a therapeutically effective amount of at least one chimeric protein, wherein the chimeric protein comprises a first and a second polypeptide chain, wherein the first chain comprises at least a portion of an immunoglobulin constant region and at least one antiviral agent, e.g., a fusion inhibitor or interferon α and the second polypeptide chain comprises at least a portion of an immunoglobulin without the antiviral agent of the first chain. In one embodiment, the subject is infected with a virus which can be treated with IFNα, e.g., hepatitis C virus. In one embodiment, the subject is infected with HIV, such as HIV-1 or HIV-2.

In one embodiment, the chimeric protein of the invention inhibits viral replication. In one embodiment, the chimeric protein of the invention prevents or inhibits viral entry into target cells, thereby stopping, preventing, or limiting the spread of a viral infection in a subject and decreasing the viral burden in an infected subject. By linking a portion of an immunoglobulin to a viral fusion inhibitor the invention provides a chimeric protein with viral fusion inhibitory activity with greater stability and greater bioavailability compared to viral fusion inhibitors alone, e.g., T20, T21, T1249. Thus, in one embodiment, the viral fusion inhibitor decreases or prevents HIV infection of a target cell, e.g., HIV-1.

a. Conditions that May be Treated

The chimeric protein of the invention can be used to inhibit or prevent the infection of a target cell by a hepatitis virus, e.g., hepatitis virus C. The chimeric protein may comprise an anti-viral agent which inhibits viral replication.

In one embodiment, the chimeric protein of the invention comprises a fusion inhibitor. The chimeric protein of the invention can be used to inhibit or prevent the infection of any target cell by any virus (see e.g. U.S. Pat. Nos. 6,086,875, 6,030,613, 6,485,726; WO 03/077834; US 2003-0235536A1). In one embodiment, the virus is an enveloped virus such as, but not limited to HIV, SIV, measles, influenza, Epstein-Barr virus, respiratory syncytia virus, or parainfluenza virus. In another embodiment, the virus is a non-enveloped virus such as rhino virus or polio virus The chimeric protein of the invention can be used to treat a subject already infected with a virus. The subject can be acutely infected with a virus. Alternatively, the subject can be chronically infected with a virus. The chimeric protein of the invention can also be used to prophylactically treat a subject at risk for contracting a viral infection, e.g., a subject known or believed to in close contact with a virus or subject believed to be infected or carrying a virus. The chimeric protein of the invention can be used to treat a subject who may have been exposed to a virus, but who has not yet been positively diagnosed.

In one embodiment, the invention relates to a method of treating a subject infected with HCV comprising administering to the subject a therapeutically effective amount of a chimeric protein, wherein the chimeric protein comprises an Fc fragment of an IgG and a cytokine, e.g., IFNα.

In one embodiment, the invention relates to a method of treating a subject infected with HIV comprising administering to the subject a therapeutically effective amount of a chimeric protein wherein the chimeric protein comprises an Fc fragment of an IgG and the viral fusion inhibitor comprises T20.

3. Methods of Treating a Subject Having a Hemostatic Disorder

The invention relates to a method of treating a subject having a hemostatic disorder comprising administering a therapeutically effective amount of at least one chimeric protein, wherein the chimeric protein comprises a first and a second chain, wherein the first chain comprises at least one clotting factor and at least a portion of an immunoglobulin constant region, and the second chain comprises at least a portion of an immunoglobulin constant region.

The chimeric protein of the invention treats or prevents a hemostatic disorder by promoting the formation of a fibrin clot. The chimeric protein of the invention can activate any member of a coagulation cascade. The clotting factor can be a participant in the extrinsic pathway, the intrinsic pathway or both. In one embodiment, the clotting factor is Factor VII or Factor VIIa. Factor VIIa can activate Factor X which interacts with Factor Va to cleave prothrombin to thrombin, which in turn cleaves fibrinogen to fibrin. In another embodiment, the clotting factor is Factor IX or Factor IXa. In yet another embodiment, the clotting factor is Factor VII or Factor VIIIa. In yet another embodiment, the clotting factor is von Willebrand Factor, Factor XI, Factor XII, Factor V, Factor X or Factor XIII.

a. Conditions That May Be Treated

The chimeric protein of the invention can be used to treat any hemostatic disorder. The hemostatic disorders that may be treated by administration of the chimeric protein of the invention include, but are not limited to, hemophilia A, hemophilia B, von Willebrand's disease, Factor XI deficiency (PTA deficiency), Factor XII deficiency, as well as deficiencies or structural abnormalities in fibrinogen, prothrombin, Factor V, Factor VII, Factor X, or Factor XIII.

In one embodiment, the hemostatic disorder is an inherited disorder. In one embodiment, the subject has hemophilia A, and the chimeric protein comprises Factor VII or Factor VIIIa. In another embodiment, the subject has hemophilia A and the chimeric protein comprises Factor VII or Factor VIIa. In another embodiment, the subject has hemophilia B and the chimeric protein comprises Factor IX or Factor IXa. In another embodiment, the subject has hemophilia B and the chimeric protein comprises Factor VII or Factor VIIa. In another embodiment, the subject has inhibitory antibodies to Factor VIII or Factor VIIIa and the chimeric protein comprises Factor VII or Factor VIIa. In yet another embodiment, the subject has inhibitory antibodies against Factor IX or Factor IXa and the chimeric protein comprises Factor VII or Factor VIIa.

The chimeric protein of the invention can be used to prophylactically treat a subject with a hemostatic disorder. The chimeric protein of the invention can be used to treat an acute bleeding episode in a subject with a hemostatic disorder In one embodiment, the hemostatic disorder is the result of a deficiency in a clotting factor, e.g., Factor IX, Factor VII. In another embodiment, the hemostatic disorder can be the result of a detective clotting factor, e.g., von Willebrand's Factor.

In another embodiment, the hemostatic disorder can be an acquired disorder. The acquired disorder can result from an underlying secondary disease or condition. The unrelated condition can be, as an example, but not as a limitation, cancer, an autoimmune disease, or pregnancy. The acquired disorder can result from old age or from medication to treat an underlying secondary disorder (e.g. cancer chemotherapy).

4. Methods of Treating a Subject in Need of a General Hemostatic Agent

The invention also relates to methods of treating a subject that does not have a hemostatic disorder or a secondary disease or condition resulting in acquisition of a hemostatic disorder. The invention thus relates to a method of treating a subject in need of a general hemostatic agent comprising administering a therapeutically effective amount of at least one chimeric protein, wherein the chimeric protein comprises a first and a second polypeptide chain wherein the first polypeptide chain comprises at least a portion of an immunoglobulin constant region and at least one clotting factor and the second chain comprises at least a portion of an immunoglobulin constant region without the clotting factor of the first polypeptide chain.

a. Conditions that May be Treated

In one embodiment, the subject in need of a general hemostatic agent is undergoing, or is about to undergo, surgery. The chimeric protein of the invention can be administered prior to or after surgery as a prophylactic. The chimeric protein of the invention can be administered during or after surgery to control an acute bleeding episode. The surgery can include, but is not limited to, liver transplantation, liver resection, or stem cell transplantation.

The chimeric protein of the invention can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding.

5. Treatment Modalities

The chimeric protein of the invention can be administered intravenously, subcutaneously, intramuscularly, or via any mucosal surface, e.g., orally, sublingually, buccally, sublingually, nasally, rectally, vaginally or via pulmonary route. The chimeric protein can be implanted within or linked to a biopolymer solid support that allows for the slow release of the chimeric protein to the desired site.

The dose of the chimeric protein of the invention will vary depending on the subject and upon the particular route of administration used. Dosages can range from 0.1 to 100,000 µg/kg body weight. In one embodiment, the dosing range is 0.1-1,000 µg/kg. The protein can be administered continuously or at specific timed intervals. In vitro assays may be employed to determine optimal dose ranges and/or schedules for administration. Many in vitro assays that measure viral infectivity are known in the art. For example, a reverse transcriptase assay, or an rt PCR assay or branched DNA assay can be used to measure HIV concentrations. A StaClot assay can be used to measure clotting activity. Additionally, effective doses may be extrapolated from dose-response curves obtained from animal models.

The invention also relates to a pharmaceutical composition comprising a viral fusion inhibitor, at least a portion of an immunoglobulin and a pharmaceutically acceptable carrier or excipient. Examples of suitable pharmaceutical carriers are described in *Remington's Pharmaceutical Sciences* by E. W. Martin. Examples of excipients can include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g. sorbitol syrup, cellulose derivatives or hydrogenated edible fats), emulsifying agents (lecithin or acacia), non-aqueous vehicles (e.g. almond oil, oily esters, ethyl alcohol, or fractionated vegetable oils), and preservatives (e.g. methyl or propyl-p-hydroxybenzoates or sorbic acid). The preparations can also include flavoring, coloring and sweetening agents. Alternatively, the composition can be presented as a dry product for constitution with water or another suitable vehicle.

For buccal and sublingual administration the composition may take the form of tablets, lozenges or fast dissolving films according to conventional protocols.

For administration by inhalation, the compounds for use according to the present invention are conveniently delivered in the form of an aerosol spray from a pressurized pack or nebulizer (e.g. in PBS), with a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can be formulated for parenteral administration (i.e. intravenous or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

The pharmaceutical composition can also be formulated for rectal administration as a suppository or retention enema, e.g., containing conventional suppository bases such as cocoa butter or other glycerides.

6. Combination Therapy

The chimeric protein of the invention can be used to treat a subject with a disease or condition in combination with at least one other known agent to treat said disease or condition.

In one embodiment, the invention relates to a method of treating a subject infected with HIV comprising administering a therapeutically effective amount of at least one chimeric protein comprising a first and a second chain, wherein the first chain comprises an HIV fusion inhibitor and at least a portion of an immunoglobulin constant region and the second chain comprises at least a portion of an immunoglobulin without an HIV fusion inhibitor of the first chain, in combination with at least one other anti-HIV agent. Said other anti-HIV agent can be any therapeutic with demonstrated anti-HIV activity. Said other anti-HIV agent can include, as an example, but not as a limitation, a protease inhibitor (e.g. Amprenavir®, Crixivan®, Ritonivir®), a reverse transcriptase nucleoside analog (e.g. AZT, DDI, D4T, 3TC, Ziagen®), a nonnucleoside analog reverse transcriptase inhibitor (e.g. Sustiva®), another HIV fusion inhibitor, a neutralizing antibody specific to HIV, an antibody specific to CD4, a CD4 mimic, e.g., CD4-IgG2 fusion protein (U.S. patent application Ser. No. 09/912,824) or an antibody specific to CCR5, or CXCR4, or a specific binding partner of CR5, or CXCR4.

In another embodiment, the invention relates to a method of treating a subject with a hemostatic disorder comprising administering a therapeutically effective amount of at least one chimeric protein comprising a first and a second chain, wherein the first chain comprises at least one clotting factor and at least a portion of an immunoglobulin constant region and the second chain comprises at least a portion of an immunoglobulin constant region without the clotting factor of the first chain, in combination with at least one other clotting factor or agent that promotes hemostasis. Said other clotting factor or agent that promotes hemostasis can be any therapeutic with demonstrated clotting activity. As an example, but not as a limitation, the clotting factor or hemostatic agent can include Factor V, Factor VII, Factor VII, Factor IX, Factor X, Factor XI, Factor XII, Factor XIII, prothrombin, or fibrinogen or activated forms of any of the preceding. The clotting factor of hemostatic agent can also include anti-fibrinolytic drugs, e.g., epsilon-amino-caproic acid, tranexamic acid.

7. Methods of Inhibiting Viral Fusion with a Target Cell

The invention also relates to an in vitro method of inhibiting HIV fusion with a mammalian cell comprising combining the mammalian cell with at least one chimeric protein, wherein the chimeric protein comprises a first and a second chain, wherein the first chain comprises at least a portion of an immunoglobulin constant region and an HIV inhibitor and the second chain comprises at least a portion of an immunoglobulin constant region without the HIV inhibitor of the first chain. The mammalian cell can include any cell or cell line susceptible to infection by HIV including but not limited to primary human CD4+ T cells or macrophages, MOLT-4 cells, CEM cells, AA5 cells or HeLa cells which express CD4 on the cell surface.

G. Methods of Isolating Chimeric Proteins

Typically, when chimeric proteins of the invention are produced they are contained in a mixture of other molecules such as other proteins or protein fragments. The invention thus provides for methods of isolating any of the chimeric proteins described supra from a mixture containing the chimeric proteins. It has been determined that the chimeric proteins of the invention bind to dye ligands under suitable conditions and that altering those conditions subsequent to binding can disrupt the bond between the dye ligand and the chimeric protein, thereby providing a method of isolating the chimeric protein. In some embodiments, the mixture may comprise a monomer-dimer hybrid, a dimer and at least a portion of an immunoglobulin constant region, e.g., an Fc. Thus, in one embodiment, the invention provides a method of isolating a monomer-dimer hybrid. In another embodiment, the invention provides a method of isolating a dimer.

Accordingly, in one embodiment, the invention provides a method of isolating a monomer-dimer hybrid from a mixture, where the mixture comprises a) the monomer-dimer hybrid comprising a first and second polypeptide chain, wherein the first chain comprises a biologically active molecule, and at least a portion of an immunoglobulin constant region and wherein the second chain comprises at least a portion of an immunoglobulin constant region without a biologically active molecule or immunoglobulin variable region;

b) a dimer comprising a first and second polypeptide chain, wherein the first and second chains both comprise a biologically active molecule, and at least a portion of an immunoglobulin constant region; and c) a portion of an immunoglobulin constant region; said method comprising 1) contacting the mixture with a dye ligand linked to a solid support under suitable conditions such that both the monomer-dimer hybrid and the dimer bind to the dye ligand;

2) removing the unbound portion of an immunoglobulin constant region;

3) altering the suitable conditions of 1) such that the binding between the monomer-dimer hybrid and the dye ligand linked to the solid support is disrupted;

4) isolating the monomer-dimer hybrid.

In some embodiments, prior to contacting the mixture with a dye ligand, the mixture may be contacted with a chromatographic substance such as protein A sepharose or the like. The mixture is eluted from the chromatographic substance using an appropriate elution buffer (e.g. a low pH buffer) and the eluate containing the mixture is then contacted with the dye ligand.

Suitable conditions for contacting the mixture with the dye ligand may include a buffer to maintain the mixture at an appropriate pH. An appropriate pH may include a pH of from 3-10, 4-9, 5-8. In one embodiment, the appropriate pH is 8.0. Any buffering agent known in the art may be used so long as it maintains the pH in the appropriate range, e.g., tris, HEPES, PIPES, MOPS. Suitable conditions may also include a wash buffer to elute unbound species from the dye ligand. The wash buffer may be any buffer which does not disrupt binding of a bound species. For example, the wash buffer can be the same buffer used in the contacting step.

Once the chimeric protein is bound to the dye ligand, the chimeric protein is isolated by altering the suitable conditions. Altering the suitable conditions may include the addition of a salt to the buffer. Any salt may be used, e.g., NaCl, KCl. The salt should be added at a concentration that is high enough to disrupt the binding between the dye ligand and the desired species, e.g., a monomer-dimer hybrid.

In some embodiments, where the mixture is comprised of an Fc, a monomer-dimer hybrid, and a dimer, it has been found that the Fc does not bind to the dye ligand and thus elutes with the flow through. The dimer binds more tightly to the dye ligand than the monomer-dimer hybrid. Thus a higher concentration of salt is required to disrupt the bond (e.g. elute) between the dimer and the dye ligand compared to the salt concentration required to disrupt the bond between the dye ligand and the monomer-dimer hybrid.

In some embodiments, NaCl may be used to isolate the monomer-dimer hybrid from the mixture. In some embodiments, the appropriate concentration of salt which disrupts the bond between the dye ligand and the monomer-dimer hybrid is from 200-700 mM, 300-600 mM, 400-500 mM. In one embodiment, the concentration of NaCl required to disrupt the binding between the dye ligand the monomer-dimer hybrid is 400 mM.

NaCl may also be used to isolate the dimer from the mixture. Typically, the monomer-dimer hybrid is isolated from the mixture before the dimer. The dimer is isolated by adding an appropriate concentration of salt to the buffer, thereby disrupting the binding between the dye ligand and the dimer. In some embodiments, the appropriate concentration of salt which disrupts the bond between the dye ligand and the dimer is from 800 mM to 2M, 900 mM to 1.5 M, 950 mM to 1.2 M. In one specific embodiment, 1M NaCl is used to disrupt the binding between the dye ligand and the dimer.

The dye ligand may be a bio-mimetic. A bio-mimetic is a human-made substance, device, or system that imitates nature. Thus, in some embodiments, the dye ligand imitates a molecule's naturally occurring ligand. The dye ligand may be chosen from Mimetic Red 1™, Mimetic Red 2™, Mimetic Orange 1™, Mimetic Orange 2™, Mimetic Orange 3™, Mimetic Yellow 1™, Mimetic Yellow 2™, Mimetic Green 1™, Mimetic Blue 1™, and Mimetic Blue 2™ (Prometic Biosciences (USA) Inc., Wayne, N.J.). In one specific embodiment, the dye ligand is Mimetic Red 2™ (Prometic Biosciences (USA) Inc., Wayne, N.J.). In certain embodiments, the dye ligand is linked to a solid support, e.g., from Mimetic Red 1 A6XL™, Mimetic Red 2 A6XL™, Mimetic Orange 1 A6XL™, Mimetic Orange 2 A6XL™, Mimetic Orange 3 A6XL™, Mimetic Yellow 1 A6XL™, Mimetic Yellow 2 A6XL™, Mimetic Green 1 A6XL™, Mimetic Blue 1 A6XL™, and Mimetic Blue 2 A6XL™ (Prometic Biosciences (USA) Inc., Wayne, N.J.).

The dye ligand may be linked to a solid support. The solid support may be any solid support known in the art (see, e.g., www.seperationsNOW.com). Examples of solid supports may include a bead, a gel, a membrane, a nanoparticle, or a microsphere. The solid support may comprise any material which can be linked to a dye ligand (e.g. agarose, polystyrene, sepharose, sephadex). Solid supports may comprise any synthetic organic polymer such as polyacrylic, vinyl polymers, acrylate, polymethacrylate, and polyacrylamide. Solid supports may also comprise a carbohydrate polymer, e.g., agarose, cellulose, or dextran. Solid supports may comprise inorganic oxides, such as silica, zirconia, titania, ceria, alumina, magnesia (i.e., magnesium oxide), or calcium oxide. Solid supports may also comprise combinations of some of the above-mentioned supports including, but not limited to, dextran-acrylamide.

EXAMPLES

Example 1

Molecular Weight Affects FcRn Mediated Transcytosis

Chimeric proteins comprised of various proteins of interest and IgG Fc were recombinantly produced (Sambrook et al. *Molecular Cloning: A Laboratory Manual*, 2 ed., Cold Spring Harbor Laboratory Press, (1989)) or in the case of contactin-Fc, MAB-β-gal, (a complex of a monoclonal antibody bound to β-gal) (Biodesign International, Saco, Me.) and MAB-GH (a complex of monoclonal antibody and growth hormone) (Research Diagnostics, Inc. Flanders, N.J.) were purchased commercially. Briefly, the genes encoding the protein of interest were cloned by PCR, and then sub-cloned into an Fc fusion expression plasmid. The plasmids were transfected into DG44 CHO cells and stable transfectants were selected and amplified with methotrexate. The chimeric protein homodimers were purified over a protein A column. The proteins tested included interferon α, growth hormone, erythropoietin, follicle stimulating hormone, Factor IX, beta-galactosidase, contactin, and Factor VIII. Linking the proteins to immunoglobulin portions, including the FcRn receptor binding partner, or using commercially available whole antibody (including the FcRn binding region)-antigen complexes permitted the investigation of transcytosis as a function of molecular weight (see U.S. Pat. No. 6,030,613). The chimeric proteins were administered to rats orally and serum levels were measured 2-4 hours post administration using an ELISA for recombinantly produced chimeric proteins and both a western blot and ELISA for commercially obtained antibody complexes and chimeric proteins. Additionally, all of the commercially obtained proteins or complexes as well as Factor VIII-Fc, Factor IX-Fc and Epo-Fc controls were iodinated using IODO beads (Pierce, Pittsburgh, Pa.). The results indicated serum levels of Fc and monoclonal antibody chimeric proteins orally administered to rats are directly related to the size of the protein. The apparent cutoff point for orally administered Fc chimeric proteins is between 200-285 kD. (Table 2).

TABLE 2

| Protein | Size (kD) | Transcytosis |
|---|---|---|
| IFNα-Fc | 92 | ++++ |
| GH-Fc | 96 | +++ |
| Epo-Fc | 120 | +++ |
| FSH-Fc | 170 | +++ |
| MAB:GH | 172-194 | +++ |
| FIX-Fc | 200 | + |
| MAB:βGal | 285-420 | − |
| Contactin-Fc | 300 | − |
| FVIIIΔ-Fc | 380 | − |

Example 2

Protein Expression and Preparation of Fc-MESNA

The coding sequence for Fc (the constant region of human IgG1) was obtained by PCR amplification from an Fc-containing plasmid using standard conditions and reagents, following the manufacturer's recommended procedure to subclone the Fc coding sequence NdeI/SapI. Briefly, the primers 5'-GTGGTCATA TGGGCATTGAAGGCAGAGGCGC-CGCTGCGGTCG-3' (SEQ ID NO:16) and 5'-GGTGGT-TGC TCTTCCGCAAAAAGCCGGAGACAGG-GAGAGACTCTTCTGCG-3' (SEQ ID NO:17) were used to amplify the Fc sequence from 500 ng of the plasmid pED-.dC.Epo-Fc using Expand High Fidelity System (Boehringer Mannheim, Basel Switzerland) in a RapidCylcler thermocycler (Idaho Technology Salt Lake City, Utah), denaturing at 95° C. for 2 minutes followed by 18 cycles of 95° C. for 0 sec, 55° C. for 0 sec, and 72° C. for 1 minute with a slope of 4, followed by 72° C. extension for 10 minutes. The PCR product was subcloned into an intermediate cloning vector and sequenced fully, and then subcloned using the NdeI and SapI sites in the pTWIN1 vector following standard procedures. Sambrook, J., Fritsch, E. F. and Maniatis, T. 1989, *Molecular Cloning: A Laboratory Manual*, 2d ed.; Cold Spring Harbor, N.Y.: Cold Spring Harbor Laboratory Press. This plasmid was then transformed into BL21 (DE3) pLysS cells using standard methods. Id. A 1 liter culture of cells was grown to an absorbance reading of 0.8 AU at 37° C., induced with 1 mM isopropyl beta-D-1-thiogalactopyranoside, and grown overnight at 25° C. Cells were pelleted by centrifugation, lysed in 20 mM Tris 8.8/1% NP40/0.1 mM phenylmethanesulfonyl fluoride/1 μg/ml Benzonase (Novagen Madison, Wis.), and bound to chitin beads (New England Biolabs; Beverly, Mass.) overnight at 4° C. Beads were then washed with several column volumes of 20 mM Tris 8.5/500 mM NaCl/1 mM EDTA, and then stored at −80° C. Purified Fc-MESNA was generated by eluting the protein from the beads in 20 mM Tris 8.5/500 mM NaCl/1 mM EDTA/500 mM 2-mercapto ethane sulfonic acid (MESNA), and the eluate was used directly in the coupling reaction, below (FIG. 5).

Example 3

Synthesis of a Small Molecule Linked to CVs-Fc

A VLA4 anatagonist described in Lin et al., 1999 *J. Med. Chem.*, 42:920 was linked to CysFc.

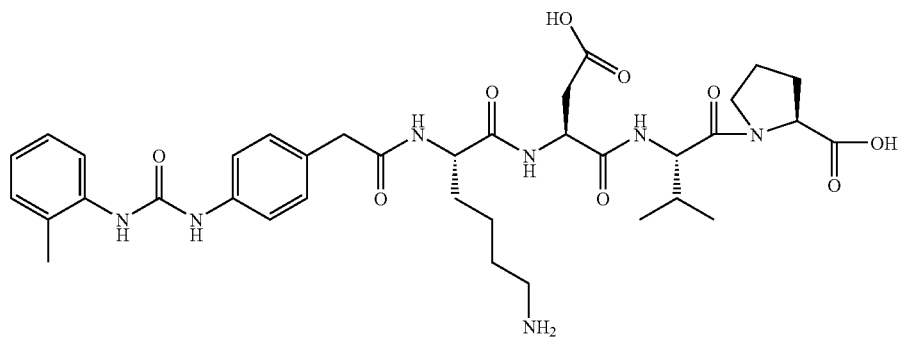

In this case, the carboxy-protected version 1 was used and reacted the free amine with 6-aminoheptanoic acid using standard amide bond coupling conditions.

Figure 6:
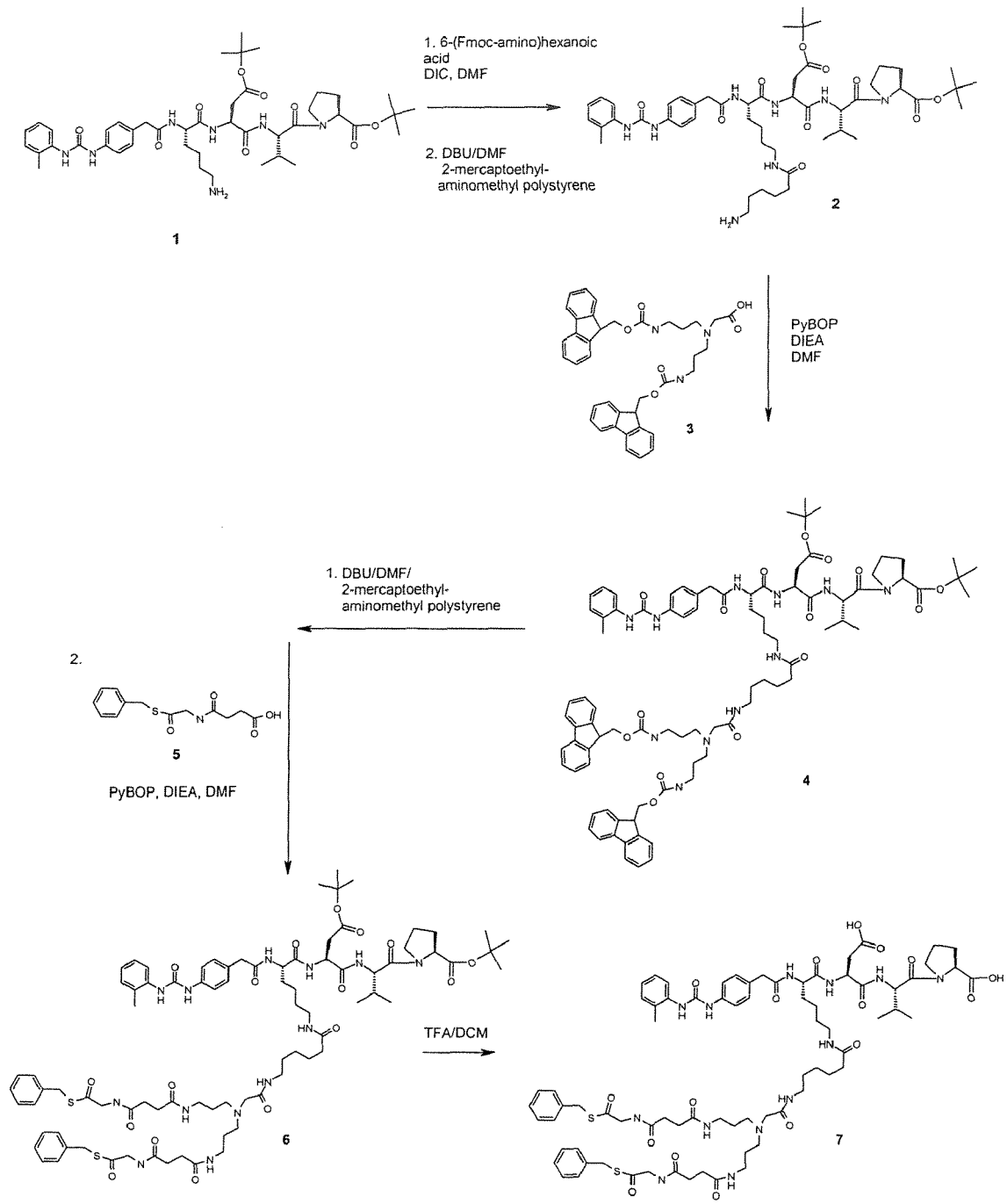
FIG. 6 shows a reaction scheme for linking a VLA antagonist to a linker molecule.

Removal of the Fmoc groups with DBU in DMF with the polystyrene-bound mercaptoethylamine gave compound 2. Coupling of N,N-bis(N-Fmoc-3-amino-propyl) glycine 3 to compound 2 in the presence of PyBOP and DIEA gave compound 4. Deprotection of the Fmoc groups again with DBU in DMF with the polystyrene-bound mercaptoethylamine, followed by coupling of thioester 5 gave compound 6. Removal of the t-butyl protecting groups gave double thioester 7 which included the active small molecule (FIG. 6). The double thioester 7 was coupled to CysFc and was shown to be attached to both N-terminal Cys residues by running a reducing SDS page gel and observing that the Fc was running at the molecular weight of a dimer (even though the disulfides between the Fc halves were reduced, the Fc still ran as a dimer due to the irreversible linkage between the two halves as a result of compound 7).

Example 4

Cloning of CVs-Fc Construct

Monomer-Dimer Mixture

Using PCR and standard molecular biology techniques (Sambrook et al. 1989, *Molecular Cloning: A Laboratory Manual*, 2ed., Cold Spring Harbor Laboratory Press), a mammalian expression construct was generated such that the coding sequence for the human IFNα signal peptide was directly abutted against the coding sequence of Fc beginning at the first cysteine residue (Cys 226, EU Numbering). Upon signal peptidase cleavage and secretion from mammalian cells, an Fc protein with an N-terminal cysteine residue was thus generated. Briefly, the primers IFNa+Sig-F (IFNa+Sig-F: 5'-GCTACTGCAGCCACCATG-GCCTTGACCTTTGCTTTAC-3') (SEQ ID NO:18) and Cys-Fc-R (5'-CAGTTCCGGAGCTGGGCACGGCG-GAGAGCCCACAGAGCAGCTTG-3') (SEQ ID NO:19)

were used in a PCR reaction to create a fragment linking the IFNα signal sequence with the N terminus of Fc, beginning with Cys 226. 500 ng of pED.dC.native hIFNα Δlinker was added to 25 pmol of each primer in a PCR reaction with Expand High Fidelity System (Boehringer Mannheim, Indianapolis, Ind.) according to manufacturer's standard protocol. The reaction was carried out in a MJ Thermocycler using the following cycles: 94° C. 2 minutes; 30 cycles of (94° C. 30 seconds, 50° C. 30 seconds, 72° C. 45 seconds), and finally 72° C. 10 minutes. The expected sized band (~112 bp) was gel purified with a Gel Extraction kit (Qiagen, Valencia Calif.), digested with the PstI and BspEI restriction enzymes, gel purified, and subcloned into the corresponding sites pED.dC. native hIFNα Δlinker to generate pED.dC.hIFNα sig seq-Cys-Fc.

Example 5

Cloning of CysFc Construct

Dimer

Similar to above, standard molecular biology techniques were used to generate a mammalian expression construct such that the coding sequence for the mouse Igκ signal peptide was directly abutted against the coding sequence of Fc beginning at the first cysteine residue (Cys 226, EU Numbering). Briefly, the following primers were used:

```
                                          (SEQ ID NO: 20)
mIgk-F:    5'-CCAACTGCAGCCACCATGGAGACAGACACAC-3'

(SEQ ID NO: 21)
mIgk-R:    5'-GGGCACGGCGGGCAACCAGTGGAACCTGGAAC-3'

(SEQ ID NO: 22)
CysFc-F:   5'-TGCCCGCCGTGCCCGGCA-3'

(SEQ ID NO: 23)
fcclv-R:   5'-ATAGAAGCCTTTGACCAGGC-3'
```

Two 25 μl PCR reactions were carried out with either mIgk-F and mIgk-R or CysFc-F and fcclv-R using Expand High Fidelity System (Boehringer Mannheim, Indianapolis, Ind.) according to manufacturer's standard protocol in a MJ Thermocycler. Both reactions used a template plasmid containing the mouse Igκ signal sequence followed by the Fc coding sequence. The expected sized bands (~88 and 444 bp, respectively) were gel purified with a Gel Extraction kit (Qiagen, Valencia Calif.), then combined in a PCR reaction with mIgk-F and fcclv-R primers and run as before. The expected sized band (~519 bp) was gel purified with a Gel Extraction kit (Qiagen, Valencia Calif.) and cloned into pED-.dC.IFNβ-Fc (vector pED.dC containing the full length human IFNβ sequence followed by the human Fc sequence, amino acids 221-447, EU numbering) using the PstI/RsrII sites to generate pED.dC.Igκ sig seq-CysFc (FIGS. 7 and 8)

Example 6

Cloning of HisXaCysFc Construct

Similar to above, standard molecular biology techniques were used to generate a mammalian expression construct such that the coding sequence for the mouse Igκ signal peptide is followed by a 6 His tag (SEQ ID NO:24), an 8 amino acid Gly-Ser linker, and a Factor Xa cleavage site (IEGR) directly abutted against the coding sequence of Fc beginning at the first cysteine residue (Cys 226, EU Numbering). In addition to mIgk-F and fcclv-R, the following primers were used:

```
SP-His-GS8-R:
                                          (SEQ ID NO: 25)
5' GGAACCAGATCCAGAGCCAGATCCGTGATGGTGATGGTGA

TGGTCACCAGTGGAACCTGGAAC-3'

GS8-Xa-Fc-F:
                                          (SEQ ID NO: 26)
5' GGATCTGGCTCTGGATCTGGTTCCATCGAAGGTCGTTG

CCCGCCGTGCCCAGCTCCGG-3'
```

Two 25 μl PCR reactions were carried out with either mIgk-F and SP-His-GS8-R or GS8-Xa-Fc-F and fcclv-R using Expand High Fidelity System (Boehringer Mannheim, Indianapolis, Ind.) according to manufacturer's standard protocol in a MJ Thermocycler. Both reactions used a template plasmid containing the mouse Igκ signal sequence followed by the Fc coding sequence. The expected sized bands (~120 and 480 bp, respectively) were gel purified with a Gel Extraction kit (Qiagen, Valencia Calif.), then combined in a PCR reaction with mIgk-F and fcclv-R primers and run as before. The expected sized band (~576 bp) was gel purified with a Gel Extraction kit (Qiagen, Valencia Calif.) and cloned into pED-.dC.IFNβ-Fc (vector pED.dC containing the full length human IFNβ sequence followed by the human Fc sequence, amino acids 221-447, EU numbering; IFNβ sequence removed in the digest) using the PstI/RsrII sites to generate pED.dC.HisXaCysFc (FIGS. 9 and 10).

Example 7

CVs-Fc Expression and Purification

CHO DG-44 cells expressing Cys-Fc were established. The pED.dC.Cys-Fc expression plasmids, and the pED-.dC.HisXaCysFc expression plasmid, which all contain the mouse dihydrofolate reductase (dhfr) gene, were transfected into CHO DG44 (dhfr deficient) cells using Superfect reagent (Qiagen; Valencia, Calif.) according to manufacturer's protocol, followed by selection for stable transfectants in αMEM (without nucleosides) tissue culture media supplemented with 5% dialyzed FBS and penicillin/streptomycin antibiotics (Invitrogen; Carlsbad, Calif.) for 10 days. The resulting pools of stably transfected cells were then amplified with various levels of methotrexate (i.e. 25 nM-100 nM) to increase expression, and the highest expressing pools were identified. Approximately $2\times10^7$ cells were used to inoculate 300 ml of growth medium in a 1700 $cm^2$ roller bottle (Corning, Corning, N.Y.). The roller bottles were incubated in a 5% $CO_2$ at 37° C. for approximately 72 hours. The growth medium was exchanged with 300 ml serum-free production medium (DMEM/F12 with 5 µg/ml bovine insulin and 10 µg/ml Gentamicin). The production medium (conditioned medium) was collected every day for 10 days and stored at 4° C. Fresh production medium was added to the roller bottles after each collection and the bottles were returned to the incubator. Prior to chromatography, the medium was clarified using a Supor Cap-100 (0.8/0.2 µm) filter from Pall Gelman Sciences (Ann Arbor, Mich.). All of the following steps were performed at 4° C. The clarified medium was applied to Protein A Sepharose, washed with 5 column volumes of 1×PBS (10 mM phosphate, pH 7.4, 2.7 mM KCl, and 137 mM NaCl), eluted with 0.1 M glycine, pH 2.7, and then neutralized with ¹⁄₁₀ volume of 1 M Tris-HCl, pH 9.0. Protein was dialyzed into PBS and used directly in conjugation reactions for the CysFc proteins, while the HisXaCysFc protein was processed further.

Example 8

Processing of HisXaCysFc Protein

In order for the Factor $X_a$ enzyme to cleave its recognition site in this protein, it was found that the interchain disulfide bonds must first be reduced, presumably because the intact disulfide adjacent to the recognition site prevented the enzyme from binding. The Factor $X_a$ activity, however, is sensitive to reducing agents, and therefore after breaking the disulfide bond of the HisXaCysFc protein, all reducing agent must be removed before adding the enzyme. One efficient way to accomplish this goal was to first bind the HisXaCysFc to a solid support, which allows one to quickly and efficiently wash in and out the desired buffers and enzymes.

HisXaCysFc protein (5 mg) in PBS was loaded on a 1 ml protein A HiTrap column (Pharmacia), washed with 10 column volumes of 1×PBS/DTT solution (10 mM phosphate, pH 7.4, 2.7 mM KCl, 137 mM NaCl, and 25 mM DTT), then the column was allowed to incubate in this solution for 1 hour at room temperature. The column was then washed with 10 column volumes of Factor $X_a$ digestion buffer (50 mM Tris pH 8.0, 100 mM NaCl, 5 mM $CaCl_2$, degassed extensively with bubbled $N_2$ while stirring), followed by 1.1 column volumes of $FX_a$ digestion buffer supplemented with $FX_a$ enzyme (80 U for 5 mg), and the column was incubated at 37° C. for 18 hrs. The column was washed with 10 column volumes of 1×PBS (10 mM phosphate, pH 7.4, 2.7 mM KCl, and 137 mM NaCl), eluted with 0.1 M glycine, pH 2.7, and then neutralized with ¹⁄₁₀ volume of 1 M Tris-HCl, pH 8.0, and analyzed by reducing SDS-PAGE to determine the efficiency of the cleavage, as can be seen by a decrease in the size of the protein band. If the protein was fully processed, the sample was dialyzed into 1×PBS and used directly in conjugation reactions.

If the protein was not fully cleaved, the fully processed HisXaCysFc was separated from the uncut protein on a Nickel column. Five column volumes of a Nickel sulfate solution (100 mM) was loaded on to a HiTrap Chelating HP column, washed with 10 column volumes of water, then equilibrated with 10 column volumes of wash buffer (20 mM phosphate pH 6.5, 500 mM NaCl). The sample containing a mixture of processed and unprocessed HisXaCysFc protein was loaded on to the column washed with 5 column volumes of wash buffer, then eluted with a gradient of 0 mM to 500 mM imidazole over 10 column volumes. Fractions were analyzed by reducing SDS-PAGE, and the fractions containing the processed HisXaCysFc protein were pooled, dialyzed into 1×PBS, and used directly in conjugation reactions.

Example 9

Coupling of T20-Thioesters to Monomer-dimer Hybrids of Cys-Fc for T20 Monomer-dimer Hybrids Cys-Fc (from hIFNα sig seq-CysFc; 4 mg, 3.2 mg/ml final concentration) and either T20-thioester or T20-PEG-thioester (2 mg, approximately 5 molar equivalents) were incubated for 16 hours at room temperature in 0.1 M Tris 8/10 mM MESNA. Analysis by SDS-PAGE (Tris-Gly gel) using reducing sample buffer indicated the presence of a new band approximately 5 kDa larger than the Fc control (>40-50% conversion to the conjugate). Previous N-terminal sequencing of Cys-Fc and unreacted Cys-Fc indicated that the signal peptide is incorrectly processed in a fraction of the molecules, leaving a mixture of (Cys)-Fc, which will react through native ligation with peptide-thioesters, and (Val)-Gly)-(Cys)-Fc, which will not. As the reaction conditions are insufficient to disrupt the dimerization of the Cys-Fc molecules, this reaction generated a mixture of T20-Cys-Fc:T20-Cys-Fc homodimers, T20-Cys-Fc: Fc monomer-dimer hybrids, and Cys-Fc:Cys-Fc homodimers. This protein was purified using size exclusion chromatography as indicated above and was able to separate the three species, which was confirmed by SDS-PAGE analysis under nonreducing conditions.

Example 10

Coupling of T20-Thioesters to Cys-Fc for Dimers

Alternatively, this same reaction indicated above was carried out with CysFc from Igκ sig seq-CysFc or processed HisXaCysFc with other peptide-thioesters, and produced a homogenous population of peptide-CysFc dimers.

Example 11

Coupling of Peptide-thioesters to Cys-Fc for Monomer-dimer Generation

In order to produce monomer-dimer hybrids by native ligation with dimeric CysFc (produced from either IgK signal sequence CysFc or processed HisXaCysFc), the reaction conditions of native ligation could be adjusted. One way would be to incubate only one equivalent of peptide-thioester with one equivalent of dimeric CysFc protein, such that only half of the total free Cys residues could react, thereby generating a mixture of peptide-CysFc dimers, peptide CysFc/Fc monomer-dimer hybrids, and unreacted CysFc dimers. Alternatively, an excess of peptide-thioester could be added with varying amounts of DTT or other reducing agent, which could compete for reacting with the available N-terminal Cys residues, and produce the same mixture. Note that some peptide-thioesters react more or less efficiently than others, and may need to be determined empirically what levels are required for the optimum amount of monomer-dimer hybrids. In all cases, peptide-thioesters could be substituted with small molecule thioesters for native ligation reactions, and other active groups could be used to react with the N-terminal Cys residues to generate other types of bonds.

Example 12

Generation of Monomer-dimer Hybrids Through Complete Reactions and Refolding with Unreacted CysFc An alternative method to generate monomer-dimer hybrids is to first use homogeneous CysFc (from IgK sig seq-CysFc or processed HisXaCysFc) to produce pure, dimeric peptide-Fc, then denature and refold with equivalent amounts of unreacted CysFc. Equal amounts of these proteins could be added together in 1×PBS, and supplemented with 8 M urea and 100 mM DTT to completely denature and reduce the proteins, in a total volume of 25-50 ml. The protein mixture could then be dialyzed into 2 liters of denaturing buffer consisting of 8 M urea, 50 mM Tris pH 8, 1 mM EDTA, 5 mM reduced glutathione (GSH) for 2 hours. The sample could then be changed into fresh denaturing buffer (2 liters) and dialyzed for 16 hours. The sample could then changed one more time into fresh denaturing buffer (2 liters) and oxidized gluathione (GSSG) added to the dialysis denaturing buffer for a final concentration of 2.5 mM GSSG. The protein could then be slowly refolded following modified literature procedures. Maeda et al. 1996, *Protein Eng.* 9:95; Ueda et al. 1997, *Cell Mol. Life Sci.* 53:929. With the protein still suspended in dialysis tubing in 1 liter of redox denaturing dialysis buffer, a new buffer of 50 mM Tris pH 8, 1 mM EDTA, 5 mM GSH and 2.5 mM GSSG could be prepared (4 liters) and pumped into the 1 liter denaturing buffer at a rate of 1 mL/min for 16 hours using a peristaltic pump. Excess buffer could be displaced such that the volume of denaturing buffer remained 1 liter. After 16 hours, the rate of addition could be increased to 3 mL/min until all of the 4 liters of renaturation buffer were consumed. The protein could then be placed into 2 liters of 50 mM Tris pH 8, 5 mM GSH, 2.5 mM GSSG, 1 mM EDTA for 2 hours and replaced with fresh identical buffer and dialyzed for 2 hours. The protein could then be dialyzed into 4 liters of PBS for 2 hours, and then into 4 liters of fresh PBS for 16 hours at 4° C. This procedure would generate a refolded mixture of peptide-Fc dimers, peptide-Fc/CysFc monomer-dimer hybrids, and CysFc dimers.

This mixture could then be purified by size exclusion chromatography using a Superdex 200 column in PBS as indicated previously.

Example 13

Cloning of the Fc Coding Sequence and Introducing the N297A Mutation

The coding sequence for the constant region of IgG1 (EU #221-447; the Fc region) was obtained by PCR amplification from a leukocyte cDNA library (Clontech, Calif.) using the following primers:

```
rcFc-F
                                       (SEQ ID NO: 27)
5'-GCTGCGGTCGACAAAACTCACACATGCCCACCGTGCCCAGCTCC

GGAACTCCTGGGCGGACCGTCAGTC-3' rcFc-R
                                       (SEQ ID NO: 28)
5'-ATTGGAATTCTCATTTACCCGGAGACAGGGAGAGGC-3'
```

The forward primer adds a SalI cloning site before the beginning of the Fc region, as well as incorporates a BspEI restriction site at amino acids 231-233 and an RsrII restriction site at amino acids 236-238 using the degeneracy of the genetic code to preserve the correct amino acid sequence (EU numbering). The reverse primer adds an EcoRI cloning site after the stop codon of the Fc. A 25 µl PCR reaction was carried out with 25 pmol of each primer using Expand High Fidelity System (Boehringer Mannheim, Indianapolis, Ind.) according to manufacturer's standard protocol in a MJ Thermocycler using the following cycles: 94° C. 2 minutes; 30 cycles of (94° C. 30 seconds, 58° C. 30 seconds, 72° C. 45 seconds), 72° C. 10 minutes. The expected sized band (~696 bp) was gel purified with a Gel Extraction kit (Qiagen, Valencia Calif.), and cloned into pGEM T-Easy (Promega, Madison, Wis.) to produce an intermediate plasmid pSYN-Fc-001 (pGEM T-Easy/Fc).

In order to mutate Asn 297 (EU numbering) of the Fc to an Ala residue, the following primers were used:

```
N297A-F
5'-GAGCAGTACGCTAGCACGTACCG-3'      (SEQ ID NO: 29)

N297A-R
5'-GGTACGTGCTAGCGTACTGCTCC-3'      (SEQ ID NO: 30)
```

Two PCR reactions were carried out with 25 pmol of either rcFc-F and N297A-R or N297A-F and rcFc-R using Expand High Fidelity System (Boehringer Mannheim, Indianapolis, Ind.) according to manufacturer's standard protocol in a MJ Thermocycler. Both reactions were carried out using 500 ng of pSYN-Fc-001 as a template using the following cycles: 94° C. 2 minutes; 16 cycles of (94° C. 30 seconds, 48° C. 30 seconds, 72° C. 45 seconds), 72° C. 10 minutes. The expected sized bands were gel purified with a Gel Extraction kit (Qiagen, Valencia Calif.), then combined in a PCR reaction with 25 µmol of rcFc-F and rcFc-R primers and run as before, annealing at 58° C. and continuing for 16 cycles. The expected sized band was gel purified with a Gel Extraction kit (Qiagen, Valencia Calif.) and cloned into pGEM T-Easy (Promega, Madison, Wis.) to produce an intermediate plasmid pSYN-Fc-002 (pGEM T Easy/Fc N297A). The N297A mutation could then be added to any Fc-containing plasmid by subcloning the BspEI/XmaI or RsrII/XmaI fragment from pSYN-Fc-002 into the corresponding sites in the plasmid of interest.

Example 14

Introducing the Mouse Igk Signal Sequence into an Fc-containing Plasmid

The mouse Igk signal sequence was added to the Fc CDS using the following primers:

```
rc-lgk sig seq-F:
                                        (SEQ ID NO: 31)
5'-TTTAAGCTTGCCGCCACCATGGAGACAGACACACTCC

TGCTATGGGTACTGCTGCTCTGGGTTCCAGGTTCCACTGGTGACAAAAC

T CACACATGCCCACCG-3'

Fc-noXma-GS-R:
                                        (SEQ ID NO: 32)
5'-GGTCAGCTCATCGCGGGATGGG-3'

Fc-noXma-GS-F:
                                        (SEQ ID NO: 33)
5'-CCCATCCCGCGATGAGCTGACC-3'
```

The rc-Igk sig seq-F primer adds a HindIII restriction site to the 5' end of the molecule, followed by a Kozak sequence (GCCGCCACC) (nucleotides 10-18 of SEQ ID NO:31) followed by the signal sequence from the mouse Igk light chain, directly abutted to the beginning of the Fc sequence (EU# 221). The Fc-noXma-GS-F and —R primers remove the internal XmaI site from the Fc coding sequence, using the degeneracy of the genetic code to preserve the correct amino acid sequence. Two 25 µl PCR reactions were carried out with 25 pmol of either rc-Igk sig seq-F and Fc-noXma-GS-R or Fc-noXma-GS-F and rcFc-R using Expand High Fidelity System (Boehringer Mannheim, Indianapolis, Ind.) according to manufacturer's standard protocol in a MJ Thermocycler. The first reaction was carried out with 500 ng of leukocyte cDNA library (BD Biosciences Clontech, Palo Alto, Calif.) as a template using the following cycles: 94° C. 2 minutes; 30 cycles of (94° C. 30 seconds, 55° C. 30 seconds, 72° C. 45 seconds), 72° C. 10 minutes. The second reaction was carried out with 500 ng of pSYN-Fc-001 as a template (above) using the following cycles: 94° C. 2 minutes; 16 cycles of (94° C. 30 seconds, 58° C. 30 seconds, 72° C. 45 seconds), 72° C. 10 minutes. The expected sized bands (~495 and 299 bp, respectively) were gel purified with a Gel Extraction kit (Qiagen, Valencia Calif.), then combined in a PCR reaction with 25 pmol of rc-Igk sig seq-F and rcFc-R primers and run as before, annealing at 58° C. and continuing for 16 cycles. The expected sized band (~772 bp) was gel purified with a Gel Extraction kit (Qiagen, Valencia Calif.) and cloned into pGEM T-Easy (Promega, Madison, Wis.) to produce the plasmid pSYN-Fc-007 (pGEM T-Easy/Igκ sig seq-Fc).

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supercede and/or take precedence over any such contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method of synthesizing a chimeric monomer-dimer hybrid comprising
   a) recombinantly expressing a fusion protein comprising a portion of an immunoglobulin containing an Fc neonatal receptor (FcRn) binding site and a splicing protein capable of forming a thioester intermediate on the C terminus of the portion containing the FcRn binding site;
   b) adding a thiol cofactor to the fusion protein of a);
   c) adding at least one biologically active molecule having an N terminal cysteine, thereby linking the biologically active molecule with the C terminus of the portion containing the FcRn binding site; and
   d) adding a second polypeptide containing an FcRn binding site, thereby forming a chimeric monomer-dimer hybrid;
   wherein the biologically active molecular is a polypeptide or a nucleic acid molecule.

2. The method of claim 1, wherein the splicing protein is intein.

3. The method of claim 1, wherein the thiol cofactor is 2-mercaptoethanesulfonic acid.

4. The method of claim 1, wherein the monomer-dimer hybrid is a dimerically linked monomer-dimer hybrid.

5. The method of claim 1, wherein the biologically active molecule is a polypeptide.

6. The method of claim 1, wherein the biologically active molecule is a nucleic acid molecule.

7. The method of claim 1, wherein both the biologically active molecule and the fusion protein are produced recombinantly.

8. The method of claim 1, wherein at least one of the biologically active molecule and the fusion protein is produced by chemical synthesis.

9. The method of claim 1, wherein the chimeric protein further comprises a linker.

10. The method of claim 1, wherein the reaction is performed in solution.

11. The method of claim 1, wherein the reaction is performed on a solid support.

12. The method of claim 11, wherein the solid support is a chitin bead.

13. The method of claim 1, wherein the biologically active molecule is selected from the group consisting of erythropoietin (EPO), interferon, a viral fusion inhibitor, and a clotting factor.

14. The method of claim 1, wherein the biologically active molecule is EPO.

15. The method of claim 1, wherein the biologically active molecule is interferon α.

16. The method of claim 1, wherein the biologically active molecule is interferon β.

* * * * *

SEQUENCE LISTING

```
<160> NUMBER OF SEQ ID NOS: 42

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Lys Asn Ser Ser Met Ile Ser Asn Thr Pro
1               5                   10

<210> SEQ ID NO 2
<211> LENGTH: 7
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 2

His Gln Ser Leu Gly Thr Gln
 1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Gln Asn Leu Ser Asp Gly Lys
 1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Gln Asn Ile Ser Asp Gly Lys
 1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Val Ile Ser Ser His Leu Gly Gln
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Phe Ala Gly Ala Ala Ala Val
 1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Phe Ala Gly Ala Ala Val
 1               5

```
<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      linker
<220> FEATURE:
<223> OTHER INFORMATION: This sequence may encompass 1-10 GA repeat
      motifs

<400> SEQUENCE: 8

Gly Ala Gly Ala Gly Ala Gly Ala Gly Ala Gly Ala Gly Ala Gly Ala
 1               5                  10                  15

Gly Ala Gly Ala
            20

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic
      linker
<220> FEATURE:
<223> OTHER INFORMATION: This sequence may encompass 1-10 GGS repeat
      motifs

<400> SEQUENCE: 9

Gly Gly Ser Gly Gly Ser Gly Gly Ser Gly Gly Ser Gly Gly Ser Gly
 1               5                  10                  15

Gly Ser Gly Gly Ser Gly Gly Ser Gly Gly Ser Gly Gly Ser
            20                  25                  30

<210> SEQ ID NO 10
<211> LENGTH: 80
<212> TYPE: PRT
<213> ORGANISM: Artificial Sequence
<220> FEATURE:
<223> OTHER INFORMATION: Description of Artificial Sequence: Synthetic
      linker
<220> FEATURE:
<221> NAME/KEY: REPEAT
<222> LOCATION: (1)..(30)
<223> OTHER INFORMATION: This region may encompass 1-10 GGS repeat
      motifs
<220> FEATURE:
<221> NAME/KEY: REPEAT
<222> LOCATION: (31)..(80)
<223> OTHER INFORMATION: This region may encompass 1-10 GGGGS repeat
      motifs

<400> SEQUENCE: 10

Gly Gly Ser Gly Gly Ser Gly Gly Ser Gly Gly Ser Gly Gly Ser Gly
 1               5                  10                  15

Gly Ser Gly Gly Ser Gly Gly Ser Gly Gly Ser Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
 65                  70                  75                  80

<210> SEQ ID NO 11
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      linker

<400> SEQUENCE: 11

Ser Gly Gly Ser Gly Gly Ser
1               5

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 12

Gly Gly Ser Gly Gly Ser Gly Gly Ser Gly Gly Ser Gly Gly Gly
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 13

Gly Gly Ser Gly Gly Ser Gly Gly Gly Gly Ser Gly Gly Gly Gly Ser
1               5                   10                  15

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 14

Gly Gly Ser Gly Gly Ser Gly Gly Ser Gly Gly Ser Gly Gly Ser Gly
1               5                   10                  15

Gly Ser

<210> SEQ ID NO 15
<211> LENGTH: 50
<212> TYPE: PRT
<213> ORGANISM: Artificial Sequence
<220> FEATURE:
<223> OTHER INFORMATION: Description of Artificial Sequence: Synthetic
      linker
<220> FEATURE:
<223> OTHER INFORMATION: This sequence may encompass 1-10 GGGGS repeat
      motifs

<400> SEQUENCE: 15

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser
    50
```

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtggtcatat gggcattgaa ggcagaggcg ccgctgcggt cg                          42

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggtggttgct cttccgcaaa aacccggaga cagggagaga ctcttctgcg                  50

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gctactgcag ccaccatggc cttgaccttt gctttac                                37

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cagttccgga gctgggcacg gcggagagcc cacagagcag cttg                        44

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccaactgcag ccaccatgga gacagacaca c                                      31

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gggcacggcg ggcaaccagt ggaacctgga ac                                     32

```
<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgcccgccgt gcccggca                                                       18

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atagaagcct ttgaccaggc                                                     20

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 24

His His His His His His
 1               5

<210> SEQ ID NO 25
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggaaccagat ccagagccag atccgtgatg gtgatggtga tggtcaccag tggaacctgg         60
aac                                                                       63

<210> SEQ ID NO 26
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggatctggct ctggatctgg ttccatcgaa ggtcgttgcc cgccgtgccc agctccgg          58

<210> SEQ ID NO 27
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
```

```
gctgcggtcg acaaaactca cacatgccca ccgtgcccag ctccggaact cctgggcgga    60
ccgtcagtc                                                            69
```

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
attggaattc tcatttaccc ggagacaggg agaggc                              36
```

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
gagcagtacg ctagcacgta ccg                                            23
```

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
ggtacgtgct agcgtactgc tcc                                            23
```

<210> SEQ ID NO 31
<211> LENGTH: 102
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
tttaagcttg ccgccaccat ggagacagac acactcctgc tatgggtact gctgctctgg    60
gttccaggtt ccactggtga caaaactcac acatgcccac cg                      102
```

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
ggtcagctca tcgcgggatg gg                                             22
```

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cccatcccgc gatgagctga cc    22

<210> SEQ ID NO 34
<211> LENGTH: 245
<212> TYPE: PRT
<213> ORGANISM: Artificial Sequence
<220> FEATURE:
<223> OTHER INFORMATION: Description of Artificial Sequence: Synthetic
      CysFc amino acid sequence

<400> SEQUENCE: 34

```
Met Ala Leu Thr Phe Ala Leu Leu Val Ala Leu Leu Val Leu Ser Cys
 1               5                  10                  15

Lys Ser Ser Cys Ser Val Gly Cys Pro Cys Pro Ala Pro Glu Leu
            20                  25                  30

Leu Gly Gly Pro Ser Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser His Glu Asp Pro Glu Val Lys Phe Asn Trp Tyr Val Asp Gly Val
65                  70                  75                  80

Glu Val His Asn Ala Lys Thr Lys Pro Arg Glu Glu Gln Tyr Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Ala Leu Pro Ala
        115                 120                 125

Pro Ile Glu Lys Thr Ile Ser Lys Ala Lys Gly Gln Pro Arg Glu Pro
    130                 135                 140

Gln Val Tyr Thr Leu Pro Pro Ser Arg Asp Glu Leu Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Lys Leu
        195                 200                 205

Thr Val Asp Lys Ser Arg Trp Gln Gln Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Pro Gly Lys
                245
```

<210> SEQ ID NO 35
<211> LENGTH: 738
<212> TYPE: DNA
<213> ORGANISM: Artificial Sequence
<220> FEATURE:
<223> OTHER INFORMATION: Description of Artificial Sequence: Synthetic
      CysFc nucleotide sequence

<400> SEQUENCE: 35
atggccttga cctttgcttt actggtggcc ctcctggtgc tcagctgcaa gtcaagctgc    60
tctgtgggct gcccgccgtg cccagctccg gaactgctgg gcggaccgtc agtcttcctc   120

-continued

```
ttcccccccaa aacccaagga caccctcatg atctcccgga ccctgaggt cacatgcgtg    180
gtggtggacg tgagccacga agaccctgag gtcaagttca actggtacgt ggacggcgtg    240
gaggtgcata atgccaagac aaagccgcgg gaggagcagt acaacagcac gtaccgtgtg    300
gtcagcgtcc tcaccgtcct gcaccaggac tggctgaatg gcaaggagta caagtgcaag    360
gtctccaaca aagccctccc agcccccatc gagaaaacca tctccaaagc caaagggcag    420
ccccgagaac acaggtgta cacctgccc ccatcccggg atgagctgac caagaaccag     480
gtcagcctga cctgcctggt caaaggcttc tatcccagcg acatcgccgt ggagtgggag    540
agcaatgggc agccggagaa caactacaag accacgcctc ccgtgttgga ctccgacggc    600
tccttcttcc tctacagcaa gctcaccgtg gacaagagca ggtggcagca ggggaacgtc    660
ttctcatgct ccgtgatgca tgaggctctg cacaaccact acacgcagaa gagcctctcc    720
ctgtctccgg gtaaatga                                                  738
```

<210> SEQ ID NO 36
<211> LENGTH: 238
<212> TYPE: PRT
<213> ORGANISM: Artificial Sequence
<220> FEATURE:
<223> OTHER INFORMATION: Description of Artificial Sequence: Synthetic Fc-MESNA amino acid sequence

<400> SEQUENCE: 36

```
Met Gly Ile Glu Gly Arg Gly Ala Ala Ala Val Asp Thr Ser His Thr
  1               5                  10                  15

Cys Pro Pro Cys Pro Ala Pro Glu Leu Leu Gly Gly Pro Ser Val Phe
             20                  25                  30

Leu Phe Pro Pro Lys Pro Lys Asp Thr Leu Met Ile Ser Arg Thr Pro
         35                  40                  45

Glu Val Thr Cys Val Val Val Asp Val Ser His Glu Asp Pro Glu Val
     50                  55                  60

Lys Phe Asn Trp Tyr Val Asp Gly Val Glu Val His Asn Ala Lys Thr
 65                  70                  75                  80

Lys Pro Arg Glu Glu Gln Tyr Asn Ser Thr Tyr Arg Val Val Ser Val
                 85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Phe
225                 230                 235
```

<210> SEQ ID NO 37
<211> LENGTH: 714
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 37

| atgggcattg | aaggcagagg | cgccgctgcg | gtcgatacta | gtcacacatg | cccaccgtgc | 60 |
| ccagcacctg | aactcctggg | gggaccgtca | gtcttcctct | tccccccaaa | acccaaggac | 120 |
| accctcatga | tctcccggac | ccctgaggtc | acatgcgtgg | tggtggacgt | gagccacgaa | 180 |
| gaccctgagg | tcaagttcaa | ctggtacgtg | gacggcgtgg | aggtgcataa | tgccaagaca | 240 |
| aagccgcggg | aggagcagta | caacagcacg | taccgtgtgg | tcagcgtcct | caccgtcctg | 300 |
| caccaggact | ggctgaatgg | caaggagtac | aagtgcaagg | tctccaacaa | agccctccca | 360 |
| gcccccatcg | agaaaaccat | ctccaaagcc | aagggcagc | cccgagaacc | acaggtgtac | 420 |
| accctgcccc | catcccggga | tgagctgacc | aagaaccagg | tcagcctgac | ctgcctggtc | 480 |
| aaaggcttct | atcccagcga | catcgccgtg | gagtgggaga | gcaatgggca | gccggagaac | 540 |
| aactacaaga | ccacgcctcc | cgtgttggac | tccgacggct | ccttcttcct | ctacagcaag | 600 |
| ctcaccgtgg | acaagagcag | gtggcagcag | gggaacgtct | tctcatgctc | cgtgatgcat | 660 |
| gaggctctgc | acaaccacta | cacgcagaag | agtctctccc | tgtctccggg | tttt | 714 |

<210> SEQ ID NO 38
<211> LENGTH: 729
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 38

| atggagacag | acacactcct | gctatgggta | ctgctgctct | gggttccagg | ttccactggt | 60 |
| tgcccgccgt | gcccagctcc | ggaactgctg | ggcggaccgt | cagtcttcct | cttcccccca | 120 |
| aaacccaagg | acaccctcat | gatctcccgg | accctgagg | tcacatgcgt | ggtggtggac | 180 |
| gtgagccacg | aagaccctga | ggtcaagttc | aactggtacg | tggacggcgt | ggaggtgcat | 240 |
| aatgccaaga | caaagccgcg | ggaggagcag | tacaacagca | cgtaccgtgt | ggtcagcgtc | 300 |
| ctcaccgtcc | tgcaccagga | ctggctgaat | ggcaaggagt | acaagtgcaa | ggtctccaac | 360 |
| aaagccctcc | cagcccccat | cgagaaaacc | atctccaaag | ccaaagggca | gccccgagaa | 420 |
| ccacaggtgt | acaccctgcc | cccatcccgg | gatgagctga | ccaagaacca | ggtcagcctg | 480 |
| acctgcctgg | tcaaaggctt | ctatcccagc | gacatcgccg | tggagtggga | gagcaatggg | 540 |
| cagccggaga | acaactacaa | gaccacgcct | cccgtgttgg | actccgacgg | ctccttcttc | 600 |
| ctctacagca | agctcaccgt | ggacaagagc | aggtggcagc | aggggaacgt | cttctcatgc | 660 |
| tccgtgatgc | atgaggctct | gcacaaccac | tacacgcaga | gagcctctc | cctgtctccg | 720 |
| ggtaaatga | | | | | | 729 |

<210> SEQ ID NO 39
<211> LENGTH: 242
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 39

| | | | | | | | | | | | | | | | |
|---|---|---|---|---|---|---|---|---|---|---|---|---|---|---|---|
|Met|Glu|Thr|Asp|Thr|Leu|Leu|Leu|Trp|Val|Leu|Leu|Leu|Trp|Val|Pro|
|1| | | |5| | | | |10| | | | |15| |

Gly Ser Thr Gly Cys Pro Pro Cys Pro Ala Pro Glu Leu Leu Gly Gly
            20                25                30

Pro Ser Val Phe Leu Phe Pro Pro Lys Pro Lys Asp Thr Leu Met Ile
        35                40                45

Ser Arg Thr Pro Glu Val Thr Cys Val Val Val Asp Val Ser His Glu
   50                 55                60

Asp Pro Glu Val Lys Phe Asn Trp Tyr Val Asp Gly Val Glu Val His
65              70                75              80

Asn Ala Lys Thr Lys Pro Arg Glu Glu Gln Tyr Asn Ser Thr Tyr Arg
        85                90              95

Val Val Ser Val Leu Thr Val Leu His Gln Asp Trp Leu Asn Gly Lys
        100              105           110

Glu Tyr Lys Cys Lys Val Ser Asn Lys Ala Leu Pro Ala Pro Ile Glu
       115             120             125

Lys Thr Ile Ser Lys Ala Lys Gly Gln Pro Arg Glu Pro Gln Val Tyr
   130               135              140

Thr Leu Pro Pro Ser Arg Asp Glu Leu Thr Lys Asn Gln Val Ser Leu
145              150                155             160

Thr Cys Leu Val Lys Gly Phe Tyr Pro Ser Asp Ile Ala Val Glu Trp
        165              170           175

Glu Ser Asn Gly Gln Pro Glu Asn Asn Tyr Lys Thr Thr Pro Pro Val
       180             185             190

Leu Asp Ser Asp Gly Ser Phe Phe Leu Tyr Ser Lys Leu Thr Val Asp
   195               200              205

Lys Ser Arg Trp Gln Gln Gly Asn Val Phe Ser Cys Ser Val Met His
       210             215            220

Glu Ala Leu His Asn His Tyr Thr Gln Lys Ser Leu Ser Leu Ser Pro
225              230                235             240

Gly Lys

<210> SEQ ID NO 40
<211> LENGTH: 786
<212> TYPE: DNA
<213> ORGANISM: Artificial Sequence
<220> FEATURE:
<223> OTHER INFORMATION: Description of Artificial Sequence: Synthetic
    nucleotide sequence

<400> SEQUENCE: 40

| | |
|---|---|
|atggagacag acacactcct gctatgggta ctgctgctct gggttccagg ttccactggt|60|
|gaccatcacc atcaccatca cggatctggc tctggatctg gttccatcga aggtcgttgc|120|
|cgccgtgcc cagctccgga actgctgggc ggaccgtcag tcttcctctt cccccccaaaa|180|
|cccaaggaca ccctcatgat ctcccggacc cctgaggtca catgcgtggt ggtggacgtg|240|
|agccacgaag accctgaggt caagttcaac tggtacgtgg acggcgtgga ggtgcataat|300|
|gccaagacaa agccgcggga ggagcagtac aacagcacgt accgtgtggt cagcgtcctc|360|
|accgtcctgc accaggactg gctgaatggc aaggagtaca agtgcaaggt ctccaacaaa|420|
|gccctcccag cccccatcga aaaaccatc tccaaagcca agggcagccc cgagaaccca|480|
|caggtgtaca ccctgccccc atcccgggat gagctgacca gaaccaggt cagcctgacc|540|

-continued

```
tgcctggtca aaggcttcta tcccagcgac atcgccgtgg agtgggagag caatgggcag    600
ccggagaaca actacaagac cacgcctccc gtgttggact ccgacggctc cttcttcctc    660
tacagcaagc tcaccgtgga caagagcagg tggcagcagg ggaacgtctt ctcatgctcc    720
gtgatgcatg aggctctgca caaccactac acgcagaaga gcctctccct gtctccgggt    780
aaatga                                                              786
```

```
<210> SEQ ID NO 41
<211> LENGTH: 261
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 41

Met Glu Thr Asp Thr Leu Leu Leu Trp Val Leu Leu Leu Trp Val Pro
1               5                   10                  15

Gly Ser Thr Gly Asp His His His His His His Gly Ser Gly Ser Gly
            20                  25                  30

Ser Gly Ser Ile Glu Gly Arg Cys Pro Pro Cys Pro Ala Pro Glu Leu
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
        195                 200                 205

Pro Pro Val Leu Asp Ser Asp Gly Ser Phe Phe Leu Tyr Ser Lys Leu
    210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260
```

```
<210> SEQ ID NO 42
<211> LENGTH: 4
<212> TYPE: PRT
<213> ORGANISM: Homo sapiens
```

```
<400> SEQUENCE: 42

Glu Leu Leu Gly
1
```